(12) United States Patent
Feller et al.

(10) Patent No.: US 11,021,691 B2
(45) Date of Patent: *Jun. 1, 2021

(54) SUCROSE PHOSPHORYLASE

(71) Applicants: C-Lecta GmbH, Leipzig (DE); New Matterhorn, LLC, Wilmington, DE (US)

(72) Inventors: Claudia Feller, Leipzig (DE); Birgit Brucher, Leipzig (DE); Andreas Vogel, Leipzig (DE)

(73) Assignees: New Matterhorn, LLC, Wilmington, DE (US); c-LEcta GmBH, Leipzig (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/761,700

(22) PCT Filed: Nov. 28, 2018

(86) PCT No.: PCT/EP2018/082854
§ 371 (c)(1),
(2) Date: May 5, 2020

(87) PCT Pub. No.: WO2019/106018
PCT Pub. Date: Jun. 6, 2019

(65) Prior Publication Data
US 2020/0377867 A1    Dec. 3, 2020

(30) Foreign Application Priority Data
Nov. 28, 2017 (EP) .................................. 17204146

(51) Int. Cl.
*C12N 9/10* (2006.01)

(52) U.S. Cl.
CPC .... *C12N 9/1066* (2013.01); *C12Y 204/01007* (2013.01)

(58) Field of Classification Search
CPC ...................... C12N 9/1066; C12Y 204/01007
See application file for complete search history.

(56) References Cited

FOREIGN PATENT DOCUMENTS

WO    WO-2011124538 A1    10/2011
WO    WO-2017153420 A1    9/2017

OTHER PUBLICATIONS

Broun et al., Catalytic plasticity of fatty acid modification enzymes underlying chemical diversity of plant lipids. Science, 1998, vol. 282: 1315-1317. (Year: 1998).*
Chica et al., Semi-rational approaches to engineering enzyme activity: combining the benefits of directed evolution and rational design. Curr. Opi. Biotechnol., 2005, vol. 16: 378-384. (Year: 2005).*
Devos et al., Practical limits of function prediction. Proteins: Structure, Function, and Genetics. 2000, vol. 41: 98-107. (Year: 2000).*
Seffernick et al., Melamine deaminase and Atrazine chlorohydrolase: 98 percent identical but functionally different. J. Bacteriol., 2001, vol. 183 (8): 2405-2410. (Year: 2001).*
Sen et al., Developments in directed evolution for enzyme functions. Appl. Biochem. Biotechnol., 2007, vol. 143: 212-223. (Year: 2007).*
Whisstock et al., Prediction of protein function from protein sequence. Q. Rev. Biophysics., 2003, vol. 36 (3): 307-340. (Year: 2003).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*
Brown, et al., Database UniProt [Online] Apr. 12, 2017 (Apr. 12, 2017), SubName: Full=Sucrose phosphorylase {ECO:0000313:EMBL:OKY88424.1}; XP002779088, retrieved from EBI accession No. UNIPROT:A0A1Q6EP51 Database accession No. A0A1Q6EP51.
Cerdobbel, et al., Increasing the thermostability of sucrose phosphorylase by a combination of sequence- and structure-based mutagenesis, Protein Engineering Design and Selection, vol. 24, No. 11, Sep. 6, 2011 (Sep. 6, 2011), pp. 829-834, XP055166150, ISSN: 1741-0126, DOI: 10.1093/protein/gzr042.
Jans, et al., Database UniProt [Online] May 29, 2013 (May 29, 2013), SubName: Full=Sucrose phosphorylase {ECO:0000313:EMBL:AGH40383.1}; XP002779090, retrieved from EBI accession No. UNIPROT:M4RCY8 Database accession No. M4RCY8.
Kim, et al., Database UniProt [Online] Mar. 3, 2009 (Mar. 3, 2009), SubName: Full=Sucrose phosphorylase {ECO:0000313 1EMBL:ACL28432.1}; EC=2.4.1.7 {ECO:0000313 1EMBL:ACL28432.1}; XP002779089, retrieved from EBI accession No. UNIPROT:B8DVD1 Database accession No. B8DVD1.
Ventura, et al., Database UniProt [Online] Oct. 29, 2014 (Oct. 29, 2014), SubName: Full=Sucrose phosphorylase {ECO:0000313 EMBL:KFI68116.1}; EC=2.4.1.7 {ECO:0000313 1EMBL:KFI68116.1}; XP002779087, retrieved from EBI accession No. UNIPROT:A0A087BAR6 Database accession No. A0A087BAR6.
International Search Report issued in PCT/EP2018/082854 dated Jan. 15, 2019.
Fujii et al (Journal of Applied Glycoscience, vol. 53 (2006) No. 2, 91-97).

(Continued)

*Primary Examiner* — Ganapathirama Raghu
(74) *Attorney, Agent, or Firm* — Blank Rome LLP

(57) ABSTRACT

The present invention relates to a sucrose phosphorylase variant comprising or consisting of an amino acid sequence with at least 75% homologous and/or identical to an amino acid sequence of wild type sucrose phosphorylase, preferably wherein the sucrose phosphorylase is characterized by different structural and functional features. The invention also relates to method for preparing aG1P and a co-product, wherein the method comprises reacting a sucrose phosphorylase with a glucoside substrate, wherein the sucrose phosphorylase is a sucrose phosphorylase as defined in the context of the present invention.

17 Claims, No Drawings
Specification includes a Sequence Listing.

(56) References Cited

OTHER PUBLICATIONS

Aerts et al (Biotechnology and Bioengineering, vol. 110, No. 10, 2013, 2563-2572).
Silverstein et al. (The Journal of Biological Chemistry, vol. 242, No. 6, 1967, 1338-1346).

* cited by examiner

SEQUENCE LISTING

```
<160> NUMBER OF SEQ ID NOS: 18

<210> SEQ ID NO 1
<211> LENGTH: 504
<212> TYPE: PRT
<213> ORGANISM: Bifidobacterium magnum
<220> FEATURE:
<223> OTHER INFORMATION: wild-type

<400> SEQUENCE: 1

Met Lys Asn Lys Val Gln Met Ile Thr Tyr Ala Asn Arg Leu Gly Asp
1               5                   10                  15

Gly Asn Leu Ala Ser Leu Thr Glu Ile Leu Arg Thr Arg Phe Asn Gly
            20                  25                  30

Ala Tyr Glu Gly Val His Ile Leu Pro Phe Phe Thr Pro Phe Asp Gly
        35                  40                  45

Ala Asp Ala Gly Phe Asp Pro Ile Asp His Thr Lys Val Asp Pro Arg
    50                  55                  60

Leu Gly Asp Trp Asn Asp Ile Ala Glu Leu Ser Lys Thr His Asp Ile
65                  70                  75                  80

Met Val Asp Ala Ile Val Asn His Met Ser Trp Glu Ser Ala Gln Phe
                85                  90                  95

Gln Asp Val Met Lys Asn Gly Glu Glu Ser Glu Tyr Pro Met Phe
                100                 105                 110

Leu Thr Met Ser Ser Val Phe Pro Leu Gly Ala Ser Glu Glu Asp Leu
            115                 120                 125

Ala Gly Ile Tyr Arg Pro Arg Pro Gly Leu Pro Phe Thr Pro Tyr Arg
        130                 135                 140

Phe Gly Asn Ala Asn Arg Leu Val Trp Thr Thr Phe Thr Pro Gln Gln
```

```
            145                 150                 155                 160
Val Asp Ile Asp Thr Asp Ser Asp Lys Gly Trp Glu Tyr Leu Met Ser
                165                 170                 175
Ile Phe Asp Gln Met Ser Lys Ser His Val Ser Gln Ile Arg Leu Asp
                180                 185                 190
Ala Val Gly Tyr Gly Ala Lys Glu Ala Gly Thr Ser Cys Phe Met Thr
                195                 200                 205
Pro Lys Thr Phe Arg Leu Ile Ser Arg Leu Arg Glu Glu Gly Ala Lys
            210                 215                 220
Arg Cys Leu Glu Ile Leu Ile Glu Val His Ser Tyr Tyr Lys Lys Gln
225                 230                 235                 240
Ile Glu Ile Ala Ser Lys Val Asp Arg Val Tyr Asp Phe Ala Leu Pro
                245                 250                 255
Pro Leu Leu Leu His Ser Leu Phe Thr Gly Asp Val Asp Ala Leu Ser
                260                 265                 270
His Trp Ile Asp Ile Arg Pro Asn Asn Ala Val Thr Val Leu Asp Thr
                275                 280                 285
His Asp Gly Ile Gly Val Ile Asp Ile Gly Ser Asp Gln Gln Asp Arg
            290                 295                 300
Ser Leu Lys Gly Leu Val Ser Asp Glu Ala Val Asp Ala Leu Val Glu
305                 310                 315                 320
Lys Ile Ala Glu Asn Ser His Gly Glu Ser Lys Ala Ala Thr Gly Ala
                325                 330                 335
Ala Ala Ser Asn Leu Asp Leu Tyr Gln Val Asn Cys Thr Tyr Tyr Ser
                340                 345                 350
Ala Leu Gly Cys Asn Asp Gln Gln Tyr Leu Ala Ala Arg Ala Val Gln
                355                 360                 365
Phe Phe Leu Pro Gly Val Pro Gln Val Tyr Tyr Val Gly Ala Leu Ala
                370                 375                 380
Gly Arg Asn Asp Met Thr Leu Leu Lys Glu Thr Gly Val Gly Arg Asp
385                 390                 395                 400
Ile Asn Arg His Tyr Tyr Ser Val Ala Glu Ile Asp Glu Asp Leu Lys
                405                 410                 415
Arg Pro Val Val Arg Ala Leu Asn Asp Leu Ala Lys Phe Arg Asn Asp
                420                 425                 430
Cys Pro Ala Phe Asp Gly Glu Phe Thr Trp Glu Arg Asp Gly Gln Asp
                435                 440                 445
Ser Val Thr Leu Thr Trp Thr Asn Gly Asp Ser His Thr Ser Leu Thr
            450                 455                 460
Phe Gln Pro Asn Leu Gly Thr Gln Asp Ala Gly Ala Pro Val Ala Thr
465                 470                 475                 480
Leu Thr Trp Asn Asp Ala Asp Gly Glu His Thr Ser Ala Asp Leu Leu
                485                 490                 495
Thr Asn Pro Pro Val Tyr Arg Lys
            500

<210> SEQ ID NO 2
<211> LENGTH: 504
<212> TYPE: PRT
<213> ORGANISM: Bifidobacterium longum
<220> FEATURE:
<223> OTHER INFORMATION: wild-type

<400> SEQUENCE: 2

Met Lys Asn Lys Val Gln Leu Ile Thr Tyr Ala Asp Arg Leu Gly Asp
```

-continued

```
  1               5                   10                  15
Gly Thr Leu Ser Ser Met Thr Asp Ile Leu Arg Thr Arg Phe Asp Gly
              20                  25                  30

Val Tyr Asp Gly Val His Ile Leu Pro Phe Phe Thr Pro Phe Asp Gly
              35                  40                  45

Ala Asp Ala Gly Phe Asp Pro Ile Asp His Thr Lys Val Asp Pro Arg
              50                  55                  60

Leu Gly Gly Trp Asp Asp Val Ala Glu Leu Ser Lys Thr His Gly Ile
 65                  70                  75                  80

Met Val Asp Ala Ile Val Asn His Met Ser Trp Glu Ser Lys Gln Phe
                  85                  90                  95

Gln Asp Val Leu Glu Lys Gly Glu Glu Ser Glu Tyr Tyr Pro Met Phe
              100                 105                 110

Leu Thr Met Ser Ser Val Phe Pro Asn Gly Ala Thr Glu Glu Asp Leu
              115                 120                 125

Ala Gly Ile Tyr Arg Pro Arg Pro Gly Leu Pro Phe Thr His Tyr Lys
              130                 135                 140

Phe Ala Gly Lys Thr Arg Leu Val Trp Val Ser Phe Thr Pro Gln Gln
145                 150                 155                 160

Val Asp Ile Asp Thr Asp Ser Asp Lys Gly Trp Glu Tyr Leu Met Ser
                  165                 170                 175

Ile Phe Asp Gln Met Ala Ala Ser His Val Ser Tyr Ile Arg Leu Asp
                  180                 185                 190

Ala Val Gly Tyr Gly Ala Lys Glu Ala Gly Thr Ser Cys Phe Met Thr
              195                 200                 205

Pro Lys Thr Phe Lys Leu Ile Ser Arg Leu Arg Glu Glu Gly Val Lys
              210                 215                 220

Arg Gly Leu Glu Ile Leu Glu Val His Ser Tyr Tyr Lys Lys Gln
225                 230                 235                 240

Val Glu Ile Ala Ser Lys Val Asp Arg Val Tyr Asp Phe Ala Leu Pro
                  245                 250                 255

Pro Leu Leu Leu His Ser Leu Asn Thr Gly His Val Glu Pro Val Ala
              260                 265                 270

His Trp Thr Asp Ile Arg Pro Asn Asn Ala Val Thr Val Leu Asp Thr
              275                 280                 285

His Asp Gly Ile Gly Val Ile Asp Ile Gly Ser Asp Gln Leu Asp Arg
              290                 295                 300

Ser Leu Lys Gly Leu Val Pro Asp Glu Asp Val Asp Asn Leu Val Asn
305                 310                 315                 320

Ala Ile His Ala Asn Thr His Gly Glu Ser Gln Ala Ala Thr Gly Ala
                  325                 330                 335

Ala Ala Ser Asn Leu Asp Leu Tyr Gln Val Asn Ser Thr Tyr Tyr Ser
              340                 345                 350

Ala Leu Gly Cys Asn Asp Gln His Tyr Ile Ala Ala Arg Ala Val Gln
              355                 360                 365

Phe Phe Leu Pro Gly Val Pro Gln Val Tyr Tyr Val Gly Ala Leu Ala
              370                 375                 380

Gly Lys Asn Asp Met Glu Leu Leu Arg Lys Thr Asn Asn Gly Arg Asp
385                 390                 395                 400

Ile Asn Arg His Tyr Tyr Ser Thr Ala Glu Ile Asp Glu Asn Leu Gln
                  405                 410                 415

Arg Pro Val Val Lys Ala Leu Asn Ala Leu Ala Lys Phe Arg Asn Glu
              420                 425                 430
```

```
Leu Asp Ala Phe Asp Gly Thr Phe Ser Tyr Ser Ala Asp Gly Asp Thr
        435                 440                 445

Ser Ile Ser Phe Thr Trp Glu Gly Thr Thr Thr Gln Ala Thr Leu Thr
    450                 455                 460

Phe Glu Pro Gly Arg Gly Leu Gly Val Glu Asn Thr Ala Ser Val Ala
465                 470                 475                 480

Thr Leu Glu Trp Arg Asp Ala Ala Gly Glu His Arg Thr Asp Asp Leu
                485                 490                 495

Ile Ala Asn Pro Pro Val Val Ala
            500

<210> SEQ ID NO 3
<211> LENGTH: 506
<212> TYPE: PRT
<213> ORGANISM: Bifidobacterium animalis
<220> FEATURE:
<223> OTHER INFORMATION: wild-type

<400> SEQUENCE: 3

Met Lys Asn Lys Val Gln Leu Ile Thr Tyr Ala Asp Arg Leu Gly Asp
1               5                   10                  15

Gly Asn Leu Ala Ser Met Thr Asp Ile Leu Arg Thr Arg Phe Asp Gly
            20                  25                  30

Val Tyr Glu Gly Val His Ile Leu Pro Phe Phe Thr Pro Phe Asp Gly
        35                  40                  45

Ala Asp Ala Gly Phe Asp Pro Ile Asp His Thr Lys Val Asp Ala Arg
    50                  55                  60

Leu Gly Asp Trp Asp Asp Ile Ala Glu Leu Ala Lys Thr His Asp Ile
65                  70                  75                  80

Met Val Asp Ala Ile Val Asn His Met Ser Trp Gln Ser Lys Gln Phe
                85                  90                  95

Gln Asp Val Leu Ala Asn Gly Glu Asp Ser Glu Tyr Tyr Pro Met Phe
            100                 105                 110

Leu Thr Met Ser Ser Val Phe Pro Asp Gly Ala Thr Glu Glu Glu Leu
        115                 120                 125

Ala Gly Ile Tyr Arg Pro Arg Pro Gly Leu Pro Phe Thr His Tyr Ser
    130                 135                 140

Phe Ala Gly Lys Thr Arg Leu Val Trp Val Thr Phe Thr Pro Gln Gln
145                 150                 155                 160

Val Asp Ile Asp Thr Asp Ser Ala Lys Gly Trp Glu Tyr Leu Met Ser
                165                 170                 175

Ile Phe Asp Gln Met Ser Lys Ser His Val Lys Tyr Ile Arg Leu Asp
            180                 185                 190

Ala Val Gly Tyr Gly Ala Lys Glu Ala Gly Thr Ser Cys Phe Met Thr
        195                 200                 205

Pro Lys Thr Phe Glu Leu Ile Ser Arg Leu Arg Glu Glu Gly Ala Lys
    210                 215                 220

Arg Gly Leu Glu Ile Leu Ile Glu Val His Ser Tyr Tyr Lys Lys Gln
225                 230                 235                 240

Val Glu Ile Ala Ala Lys Val Asp Arg Val Tyr Asp Phe Ala Leu Pro
                245                 250                 255

Pro Leu Leu Leu His Ser Leu Phe Thr Gly Lys Val Asp Ala Leu Ala
            260                 265                 270

His Trp Thr Glu Ile Arg Pro Asn Asn Ala Val Thr Val Leu Asp Thr
        275                 280                 285
```

```
His Asp Gly Ile Gly Val Ile Asp Ile Gly Ser Asp Gln Leu Asp Arg
    290                 295                 300

Ser Leu Lys Gly Leu Val Pro Asp Ala Asp Val Asp Asn Met Val Glu
305                 310                 315                 320

Thr Ile Ala Lys Asn Thr His Gly Glu Ser Lys Ala Ala Thr Gly Ala
                325                 330                 335

Ala Ala Ser Asn Leu Asp Leu Tyr Gln Val Asn Ser Thr Tyr Tyr Ser
            340                 345                 350

Ala Leu Gly Cys Asn Asp Gln His Tyr Ile Ala Ala Arg Ala Val Gln
        355                 360                 365

Phe Phe Leu Pro Gly Val Pro Gln Val Tyr Tyr Val Gly Ala Leu Ala
    370                 375                 380

Gly Glu Asn Asp Met Glu Leu Leu Lys Arg Thr Asn Val Gly Arg Asp
385                 390                 395                 400

Ile Asn Arg His Tyr Tyr Thr Thr Ser Glu Ile Asp Lys Asn Leu Glu
                405                 410                 415

Arg Pro Val Val Lys Ala Leu Asn Ala Leu Ala Arg Phe Arg Asn Glu
            420                 425                 430

Leu Pro Ala Phe Asp Gly Asp Phe Ser Tyr Ser Val Gly Asp Asp Glu
        435                 440                 445

Ser Ile Ala Phe Ser Trp Asn Gly Phe Gly Ser Ser Ala Thr Leu Thr
    450                 455                 460

Phe Thr Pro Ser Lys Gly Met Gly Val Glu Asn Pro Gln Ser Val Ala
465                 470                 475                 480

Thr Leu Val Trp Thr Asp Ser Thr Gly Glu His Arg Thr Asp Asp Leu
                485                 490                 495

Ile Ala Asn Pro Pro Val Met Gln Ala Ser
            500                 505

<210> SEQ ID NO 4
<211> LENGTH: 503
<212> TYPE: PRT
<213> ORGANISM: Bifidobacterium thermophilum
<220> FEATURE:
<223> OTHER INFORMATION: wild-type

<400> SEQUENCE: 4

Met Lys Asn Lys Val Gln Leu Ile Thr Tyr Ala Asn Arg Leu Gly Glu
1               5                   10                  15

Gly Thr Ile Lys Ser Leu Thr Asp Val Leu Arg Thr Arg Phe Asp Gly
            20                  25                  30

Val Tyr Glu Gly Val His Ile Leu Pro Phe Phe Thr Pro Phe Asp Gly
        35                  40                  45

Ala Asp Ala Gly Phe Asp Pro Val Asp His Thr Lys Val Asp Pro Arg
    50                  55                  60

Leu Gly Thr Trp Asp Asp Ile Ala Glu Leu Ser Lys Thr His Asp Ile
65                  70                  75                  80

Met Val Asp Thr Ile Val Asn His Met Ser Trp Glu Ser Lys Gln Phe
                85                  90                  95

Gln Asp Val Met Lys Arg Gly Glu Asp Ser Pro Tyr Tyr Pro Met Phe
            100                 105                 110

Leu Thr Met Ser Ser Val Phe Pro Asp Gly Ala Thr Glu Glu Asp Leu
        115                 120                 125

Ala Gly Ile Tyr Arg Pro Arg Pro Gly Leu Pro Phe Thr His Tyr Thr
    130                 135                 140
```

Trp Gly Gly Lys Thr Arg Leu Val Trp Thr Thr Phe Thr Pro Gln Gln
145                 150                 155                 160

Val Asp Ile Asp Thr Asp Ser Lys Glu Gly Trp Asp Tyr Leu Leu Ser
                165                 170                 175

Ile Leu Asp Gln Leu Ser Arg Ser His Val Ser Tyr Ile Arg Leu Asp
            180                 185                 190

Ala Val Gly Tyr Gly Ala Lys Gln Ala Lys Thr Ser Cys Phe Met Thr
        195                 200                 205

Pro Lys Thr Phe Asp Leu Ile Gly Arg Ile Lys Ala Glu Ala Glu Ser
    210                 215                 220

Arg Gly Leu Glu Thr Leu Ile Glu Val His Ser Tyr Tyr Lys Lys Gln
225                 230                 235                 240

Val Ala Ile Ala Asn Lys Val Asp Arg Val Tyr Asp Phe Ala Ile Pro
                245                 250                 255

Gly Leu Leu His Ala Leu Thr Thr Gly Lys Thr Glu Pro Ile Ala
            260                 265                 270

Lys Trp Val Glu Val Arg Pro Asn Asn Ala Val Thr Val Leu Asp Thr
        275                 280                 285

His Asp Gly Ile Gly Val Ile Asp Ile Gly Ser Asp Gln Leu Asp Arg
    290                 295                 300

Ser Leu Lys Gly Leu Val Pro Asp Glu Val Asp Gln Leu Val Glu
305                 310                 315                 320

Thr Ile His Glu Asn Thr His Gly Glu Ser Arg Ala Ala Thr Gly Ala
                325                 330                 335

Ala Ala Ser Asn Leu Asp Leu Tyr Gln Val Asn Ser Thr Tyr Tyr Ser
            340                 345                 350

Ala Leu Gly Cys Asn Asp Gln His Tyr Leu Ala Ala Arg Ala Val Gln
        355                 360                 365

Phe Phe Leu Pro Gly Val Pro Gln Val Tyr Tyr Val Gly Ala Leu Ala
    370                 375                 380

Gly Ala Asn Asp Met Glu Leu Leu His Arg Thr Asn Val Gly Arg Asp
385                 390                 395                 400

Ile Asn Arg His Tyr Tyr Ser Val Glu Glu Ile Asp Arg Asn Leu Glu
                405                 410                 415

Arg Pro Val Val Lys Ala Leu Asn Ala Leu Cys Arg Met Arg Asn Gln
            420                 425                 430

Leu Asp Ala Phe Asp Gly Glu Phe Thr Phe Ser His Glu Gly Asp Thr
        435                 440                 445

Leu Thr Phe Asp Trp Lys Gly Glu Thr Thr Ser Ala Thr Leu Thr Phe
    450                 455                 460

Glu Pro Lys Arg Gly Leu Gly Val Asp Asn Gln Ala Ser Val Cys Thr
465                 470                 475                 480

Leu Arg Trp Ser Asp Ala Ala Gly Glu His Glu Thr Asp Asp Leu Leu
                485                 490                 495

Ala Ala Pro Pro Thr Val Ala
            500

<210> SEQ ID NO 5
<211> LENGTH: 504
<212> TYPE: PRT
<213> ORGANISM: Bifidobacterium adolescentis
<220> FEATURE:
<223> OTHER INFORMATION: wild-type

<400> SEQUENCE: 5

-continued

Met Lys Asn Lys Val Gln Leu Ile Thr Tyr Ala Asp Arg Leu Gly Asp
1               5                   10                  15

Gly Thr Ile Lys Ser Met Thr Asp Ile Leu Arg Thr Arg Phe Asp Gly
            20                  25                  30

Val Tyr Asp Gly Val His Ile Leu Pro Phe Phe Thr Pro Phe Asp Gly
        35                  40                  45

Ala Asp Ala Gly Phe Asp Pro Ile Asp His Thr Lys Val Asp Glu Arg
    50                  55                  60

Leu Gly Ser Trp Asp Asp Val Ala Glu Leu Ser Lys Thr His Asn Ile
65              70                  75                  80

Met Val Asp Ala Ile Val Asn His Met Ser Trp Glu Ser Lys Gln Phe
                85                  90                  95

Gln Asp Val Leu Ala Lys Gly Glu Ser Glu Tyr Tyr Pro Met Phe
            100                 105                 110

Leu Thr Met Ser Ser Val Phe Pro Asn Gly Ala Thr Glu Glu Asp Leu
        115                 120                 125

Ala Gly Ile Tyr Arg Pro Arg Pro Gly Leu Pro Phe Thr His Tyr Lys
    130                 135                 140

Phe Ala Gly Lys Thr Arg Leu Val Trp Val Ser Phe Thr Pro Gln Gln
145                 150                 155                 160

Val Asp Ile Asp Thr Asp Ser Asp Lys Gly Trp Glu Tyr Leu Met Ser
                165                 170                 175

Ile Phe Asp Gln Met Ala Ala Ser His Val Ser Tyr Ile Arg Leu Asp
                180                 185                 190

Ala Val Gly Tyr Gly Ala Lys Glu Ala Gly Thr Ser Cys Phe Met Thr
            195                 200                 205

Pro Lys Thr Phe Lys Leu Ile Ser Arg Leu Arg Glu Glu Gly Val Lys
    210                 215                 220

Arg Gly Leu Glu Ile Leu Ile Glu Val His Ser Tyr Tyr Lys Lys Gln
225                 230                 235                 240

Val Glu Ile Ala Ser Lys Val Asp Arg Val Tyr Asp Phe Ala Leu Pro
                245                 250                 255

Pro Leu Leu Leu His Ala Leu Ser Thr Gly His Val Glu Pro Val Ala
            260                 265                 270

His Trp Thr Asp Ile Arg Pro Asn Asn Ala Val Thr Val Leu Asp Thr
            275                 280                 285

His Asp Gly Ile Gly Val Ile Asp Ile Gly Ser Asp Gln Leu Asp Arg
    290                 295                 300

Ser Leu Lys Gly Leu Val Pro Asp Glu Asp Val Asp Asn Leu Val Asn
305                 310                 315                 320

Thr Ile His Ala Asn Thr His Gly Glu Ser Gln Ala Ala Thr Gly Ala
                325                 330                 335

Ala Ala Ser Asn Leu Asp Leu Tyr Gln Val Asn Ser Thr Tyr Tyr Ser
            340                 345                 350

Ala Leu Gly Cys Asn Asp Gln His Tyr Ile Ala Ala Arg Ala Val Gln
        355                 360                 365

Phe Phe Leu Pro Gly Val Pro Gln Val Tyr Tyr Val Gly Ala Leu Ala
370                 375                 380

Gly Lys Asn Asp Met Glu Leu Leu Arg Lys Thr Asn Gly Arg Asp
385                 390                 395                 400

Ile Asn Arg His Tyr Tyr Ser Thr Ala Glu Ile Asp Glu Asn Leu Lys
                405                 410                 415

-continued

Arg Pro Val Val Lys Ala Leu Asn Ala Leu Ala Lys Phe Arg Asn Glu
            420                 425                 430

Leu Asp Ala Phe Asp Gly Thr Phe Ser Tyr Thr Thr Asp Asp Thr
            435                 440                 445

Ser Ile Ser Phe Thr Trp Arg Gly Glu Thr Ser Gln Ala Thr Leu Thr
450                 455                 460

Phe Glu Pro Lys Arg Gly Leu Gly Val Asp Asn Thr Thr Pro Val Ala
465                 470                 475                 480

Met Leu Glu Trp Glu Asp Ser Ala Gly Asp His Arg Ser Asp Asp Leu
            485                 490                 495

Ile Ala Asn Pro Pro Val Val Ala
            500

<210> SEQ ID NO 6
<211> LENGTH: 504
<212> TYPE: PRT
<213> ORGANISM: Artificial Sequence
<220> FEATURE:
<223> OTHER INFORMATION: >E92L

<400> SEQUENCE: 6

Met Lys Asn Lys Val Gln Met Ile Thr Tyr Ala Asn Arg Leu Gly Asp
1               5                   10                  15

Gly Asn Leu Ala Ser Leu Thr Glu Ile Leu Arg Thr Arg Phe Asn Gly
            20                  25                  30

Ala Tyr Glu Gly Val His Ile Leu Pro Phe Phe Thr Pro Phe Asp Gly
            35                  40                  45

Ala Asp Ala Gly Phe Asp Pro Ile Asp His Thr Lys Val Asp Pro Arg
50                  55                  60

Leu Gly Asp Trp Asn Asp Ile Ala Glu Leu Ser Lys Thr His Asp Ile
65                  70                  75                  80

Met Val Asp Ala Ile Val Asn His Met Ser Trp Leu Ser Ala Gln Phe
            85                  90                  95

Gln Asp Val Met Lys Asn Gly Glu Glu Ser Glu Tyr Tyr Pro Met Phe
            100                 105                 110

Leu Thr Met Ser Ser Val Phe Pro Leu Gly Ala Ser Glu Glu Asp Leu
            115                 120                 125

Ala Gly Ile Tyr Arg Pro Arg Pro Gly Leu Pro Phe Thr Pro Tyr Arg
130                 135                 140

Phe Gly Asn Ala Asn Arg Leu Val Trp Thr Thr Phe Thr Pro Gln Gln
145                 150                 155                 160

Val Asp Ile Asp Thr Asp Ser Asp Lys Gly Trp Glu Tyr Leu Met Ser
            165                 170                 175

Ile Phe Asp Gln Met Ser Lys Ser His Val Ser Gln Ile Arg Leu Asp
            180                 185                 190

Ala Val Gly Tyr Gly Ala Lys Glu Ala Gly Thr Ser Cys Phe Met Thr
            195                 200                 205

Pro Lys Thr Phe Arg Leu Ile Ser Arg Leu Arg Glu Glu Gly Ala Lys
            210                 215                 220

Arg Cys Leu Glu Ile Leu Ile Glu Val His Ser Tyr Tyr Lys Lys Gln
225                 230                 235                 240

Ile Glu Ile Ala Ser Lys Val Asp Arg Val Tyr Asp Phe Ala Leu Pro
            245                 250                 255

Pro Leu Leu Leu His Ser Leu Phe Thr Gly Asp Val Asp Ala Leu Ser
            260                 265                 270

-continued

```
His Trp Ile Asp Ile Arg Pro Asn Asn Ala Val Thr Val Leu Asp Thr
            275                 280                 285

His Asp Gly Ile Gly Val Ile Asp Ile Gly Ser Asp Gln Gln Asp Arg
290                 295                 300

Ser Leu Lys Gly Leu Val Ser Asp Glu Ala Val Asp Ala Leu Val Glu
305                 310                 315                 320

Lys Ile Ala Glu Asn Ser His Gly Glu Ser Lys Ala Ala Thr Gly Ala
                325                 330                 335

Ala Ala Ser Asn Leu Asp Leu Tyr Gln Val Asn Cys Thr Tyr Tyr Ser
                340                 345                 350

Ala Leu Gly Cys Asn Asp Gln Gln Tyr Leu Ala Ala Arg Ala Val Gln
                355                 360                 365

Phe Phe Leu Pro Gly Val Pro Gln Val Tyr Tyr Val Gly Ala Leu Ala
        370                 375                 380

Gly Arg Asn Asp Met Thr Leu Leu Lys Glu Thr Gly Val Gly Arg Asp
385                 390                 395                 400

Ile Asn Arg His Tyr Tyr Ser Val Ala Glu Ile Asp Glu Asp Leu Lys
                405                 410                 415

Arg Pro Val Val Arg Ala Leu Asn Asp Leu Ala Lys Phe Arg Asn Asp
            420                 425                 430

Cys Pro Ala Phe Asp Gly Glu Phe Thr Trp Glu Arg Asp Gly Gln Asp
        435                 440                 445

Ser Val Thr Leu Thr Trp Thr Asn Gly Asp Ser His Thr Ser Leu Thr
    450                 455                 460

Phe Gln Pro Asn Leu Gly Thr Gln Asp Ala Gly Ala Pro Val Ala Thr
465                 470                 475                 480

Leu Thr Trp Asn Asp Ala Asp Gly Glu His Thr Ser Ala Asp Leu Leu
                485                 490                 495

Thr Asn Pro Pro Val Tyr Arg Lys
                500

<210> SEQ ID NO 7
<211> LENGTH: 504
<212> TYPE: PRT
<213> ORGANISM: Artificial Sequence
<220> FEATURE:
<223> OTHER INFORMATION: >S124Q

<400> SEQUENCE: 7

Met Lys Asn Lys Val Gln Met Ile Thr Tyr Ala Asn Arg Leu Gly Asp
1               5                   10                  15

Gly Asn Leu Ala Ser Leu Thr Glu Ile Leu Arg Thr Arg Phe Asn Gly
                20                  25                  30

Ala Tyr Glu Gly Val His Ile Leu Pro Phe Phe Thr Pro Phe Asp Gly
            35                  40                  45

Ala Asp Ala Gly Phe Asp Pro Ile Asp His Thr Lys Val Asp Pro Arg
    50                  55                  60

Leu Gly Asp Trp Asn Asp Ile Ala Glu Leu Ser Lys Thr His Asp Ile
65                  70                  75                  80

Met Val Asp Ala Ile Val Asn His Met Ser Trp Glu Ser Ala Gln Phe
                85                  90                  95

Gln Asp Val Met Lys Asn Gly Glu Glu Ser Glu Tyr Tyr Pro Met Phe
                100                 105                 110

Leu Thr Met Ser Ser Val Phe Pro Leu Gly Ala Gln Glu Glu Asp Leu
            115                 120                 125
```

```
Ala Gly Ile Tyr Arg Pro Arg Pro Gly Leu Pro Phe Thr Pro Tyr Arg
        130                 135                 140

Phe Gly Asn Ala Asn Arg Leu Val Trp Thr Thr Phe Thr Pro Gln Gln
145                 150                 155                 160

Val Asp Ile Asp Thr Asp Ser Asp Lys Gly Trp Glu Tyr Leu Met Ser
                165                 170                 175

Ile Phe Asp Gln Met Ser Lys Ser His Val Ser Gln Ile Arg Leu Asp
                180                 185                 190

Ala Val Gly Tyr Gly Ala Lys Glu Ala Gly Thr Ser Cys Phe Met Thr
            195                 200                 205

Pro Lys Thr Phe Arg Leu Ile Ser Arg Leu Arg Glu Glu Gly Ala Lys
210                 215                 220

Arg Cys Leu Glu Ile Leu Ile Glu Val His Ser Tyr Lys Lys Gln
225                 230                 235                 240

Ile Glu Ile Ala Ser Lys Val Asp Arg Val Tyr Asp Phe Ala Leu Pro
                245                 250                 255

Pro Leu Leu Leu His Ser Leu Phe Thr Gly Asp Val Asp Ala Leu Ser
            260                 265                 270

His Trp Ile Asp Ile Arg Pro Asn Asn Ala Val Thr Val Leu Asp Thr
    275                 280                 285

His Asp Gly Ile Gly Val Ile Asp Ile Gly Ser Asp Gln Gln Asp Arg
    290                 295                 300

Ser Leu Lys Gly Leu Val Ser Asp Glu Ala Val Asp Ala Leu Val Glu
305                 310                 315                 320

Lys Ile Ala Glu Asn Ser His Gly Glu Ser Lys Ala Ala Thr Gly Ala
                325                 330                 335

Ala Ala Ser Asn Leu Asp Leu Tyr Gln Val Asn Cys Thr Tyr Tyr Ser
            340                 345                 350

Ala Leu Gly Cys Asn Asp Gln Gln Tyr Leu Ala Ala Arg Ala Val Gln
        355                 360                 365

Phe Phe Leu Pro Gly Val Pro Gln Val Tyr Tyr Val Gly Ala Leu Ala
    370                 375                 380

Gly Arg Asn Asp Met Thr Leu Leu Lys Glu Thr Gly Val Gly Arg Asp
385                 390                 395                 400

Ile Asn Arg His Tyr Tyr Ser Val Ala Glu Ile Asp Glu Asp Leu Lys
                405                 410                 415

Arg Pro Val Val Arg Ala Leu Asn Asp Leu Ala Lys Phe Arg Asn Asp
            420                 425                 430

Cys Pro Ala Phe Asp Gly Glu Phe Thr Trp Glu Arg Asp Gly Gln Asp
        435                 440                 445

Ser Val Thr Leu Thr Trp Thr Asn Gly Asp Ser His Thr Ser Leu Thr
450                 455                 460

Phe Gln Pro Asn Leu Gly Thr Gln Asp Ala Gly Ala Pro Val Ala Thr
465                 470                 475                 480

Leu Thr Trp Asn Asp Ala Asp Gly Glu His Thr Ser Ala Asp Leu Leu
                485                 490                 495

Thr Asn Pro Pro Val Tyr Arg Lys
            500

<210> SEQ ID NO 8
<211> LENGTH: 504
<212> TYPE: PRT
<213> ORGANISM: Artificial Sequence
<220> FEATURE:
<223> OTHER INFORMATION: >S124K
```

<400> SEQUENCE: 8

```
Met Lys Asn Lys Val Gln Met Ile Thr Tyr Ala Asn Arg Leu Gly Asp
1               5                   10                  15
Gly Asn Leu Ala Ser Leu Thr Glu Ile Leu Arg Thr Arg Phe Asn Gly
            20                  25                  30
Ala Tyr Glu Gly Val His Ile Leu Pro Phe Phe Thr Pro Phe Asp Gly
        35                  40                  45
Ala Asp Ala Gly Phe Asp Pro Ile Asp His Thr Lys Val Asp Pro Arg
    50                  55                  60
Leu Gly Asp Trp Asn Asp Ile Ala Glu Leu Ser Lys Thr His Asp Ile
65                  70                  75                  80
Met Val Asp Ala Ile Val Asn His Met Ser Trp Glu Ser Ala Gln Phe
                85                  90                  95
Gln Asp Val Met Lys Asn Gly Glu Glu Ser Glu Tyr Tyr Pro Met Phe
            100                 105                 110
Leu Thr Met Ser Ser Val Phe Pro Leu Gly Ala Lys Glu Glu Asp Leu
        115                 120                 125
Ala Gly Ile Tyr Arg Pro Arg Pro Gly Leu Pro Phe Thr Pro Tyr Arg
    130                 135                 140
Phe Gly Asn Ala Asn Arg Leu Val Trp Thr Thr Phe Thr Pro Gln Gln
145                 150                 155                 160
Val Asp Ile Asp Thr Asp Ser Asp Lys Gly Trp Glu Tyr Leu Met Ser
                165                 170                 175
Ile Phe Asp Gln Met Ser Lys Ser His Val Ser Gln Ile Arg Leu Asp
            180                 185                 190
Ala Val Gly Tyr Gly Ala Lys Glu Ala Gly Thr Ser Cys Phe Met Thr
        195                 200                 205
Pro Lys Thr Phe Arg Leu Ile Ser Arg Leu Arg Glu Glu Gly Ala Lys
    210                 215                 220
Arg Cys Leu Glu Ile Leu Ile Glu Val His Ser Tyr Tyr Lys Lys Gln
225                 230                 235                 240
Ile Glu Ile Ala Ser Lys Val Asp Arg Val Tyr Asp Phe Ala Leu Pro
                245                 250                 255
Pro Leu Leu His Ser Leu Phe Thr Gly Asp Val Asp Ala Leu Ser
            260                 265                 270
His Trp Ile Asp Ile Arg Pro Asn Asn Ala Val Thr Val Leu Asp Thr
        275                 280                 285
His Asp Gly Ile Gly Val Ile Asp Ile Gly Ser Asp Gln Gln Asp Arg
    290                 295                 300
Ser Leu Lys Gly Leu Val Ser Asp Glu Ala Val Asp Ala Leu Val Glu
305                 310                 315                 320
Lys Ile Ala Glu Asn Ser His Gly Glu Ser Lys Ala Ala Thr Gly Ala
                325                 330                 335
Ala Ala Ser Asn Leu Asp Leu Tyr Gln Val Asn Cys Thr Tyr Tyr Ser
            340                 345                 350
Ala Leu Gly Cys Asn Asp Gln Gln Tyr Leu Ala Ala Arg Ala Val Gln
        355                 360                 365
Phe Phe Leu Pro Gly Val Pro Gln Val Tyr Tyr Val Gly Ala Leu Ala
    370                 375                 380
Gly Arg Asn Asp Met Thr Leu Leu Lys Glu Thr Gly Val Gly Arg Asp
385                 390                 395                 400
Ile Asn Arg His Tyr Tyr Ser Val Ala Glu Ile Asp Glu Asp Leu Lys
```

-continued

```
                405                 410                 415
        Arg Pro Val Val Arg Ala Leu Asn Asp Leu Ala Lys Phe Arg Asn Asp
                420                 425                 430

Cys Pro Ala Phe Asp Gly Glu Phe Thr Trp Glu Arg Asp Gly Gln Asp
                435                 440                 445

Ser Val Thr Leu Thr Trp Thr Asn Gly Asp Ser His Thr Ser Leu Thr
        450                 455                 460

Phe Gln Pro Asn Leu Gly Thr Gln Asp Ala Gly Ala Pro Val Ala Thr
        465                 470                 475                 480

Leu Thr Trp Asn Asp Ala Asp Gly Glu His Thr Ser Ala Asp Leu Leu
                485                 490                 495

Thr Asn Pro Pro Val Tyr Arg Lys
                500

<210> SEQ ID NO 9
<211> LENGTH: 504
<212> TYPE: PRT
<213> ORGANISM: Artificial Sequence
<220> FEATURE:
<223> OTHER INFORMATION: >S124T

<400> SEQUENCE: 9

Met Lys Asn Lys Val Gln Met Ile Thr Tyr Ala Asn Arg Leu Gly Asp
1               5                   10                  15

Gly Asn Leu Ala Ser Leu Thr Glu Ile Leu Arg Thr Arg Phe Asn Gly
                20                  25                  30

Ala Tyr Glu Gly Val His Ile Leu Pro Phe Phe Thr Pro Phe Asp Gly
            35                  40                  45

Ala Asp Ala Gly Phe Asp Pro Ile Asp His Thr Lys Val Asp Pro Arg
        50                  55                  60

Leu Gly Asp Trp Asn Asp Ile Ala Glu Leu Ser Lys Thr His Asp Ile
65                  70                  75                  80

Met Val Asp Ala Ile Val Asn His Met Ser Trp Glu Ser Ala Gln Phe
                85                  90                  95

Gln Asp Val Met Lys Asn Gly Glu Glu Ser Glu Tyr Tyr Pro Met Phe
            100                 105                 110

Leu Thr Met Ser Ser Val Phe Pro Leu Gly Ala Thr Glu Glu Asp Leu
        115                 120                 125

Ala Gly Ile Tyr Arg Pro Arg Pro Gly Leu Pro Phe Thr Pro Tyr Arg
    130                 135                 140

Phe Gly Asn Ala Asn Arg Leu Val Trp Thr Thr Phe Thr Pro Gln Gln
145                 150                 155                 160

Val Asp Ile Asp Thr Asp Ser Asp Lys Gly Trp Glu Tyr Leu Met Ser
                165                 170                 175

Ile Phe Asp Gln Met Ser Lys Ser His Val Ser Gln Ile Arg Leu Asp
            180                 185                 190

Ala Val Gly Tyr Gly Ala Lys Glu Ala Gly Thr Ser Cys Phe Met Thr
        195                 200                 205

Pro Lys Thr Phe Arg Leu Ile Ser Arg Leu Arg Glu Glu Gly Ala Lys
    210                 215                 220

Arg Cys Leu Glu Ile Leu Ile Glu Val His Ser Tyr Tyr Lys Lys Gln
225                 230                 235                 240

Ile Glu Ile Ala Ser Lys Val Asp Arg Val Tyr Asp Phe Ala Leu Pro
                245                 250                 255

Pro Leu Leu Leu His Ser Leu Phe Thr Gly Asp Val Asp Ala Leu Ser
```

```
                260                 265                 270
His Trp Ile Asp Ile Arg Pro Asn Asn Ala Val Thr Val Leu Asp Thr
        275                 280                 285

His Asp Gly Ile Gly Val Ile Asp Ile Gly Ser Asp Gln Gln Asp Arg
        290                 295                 300

Ser Leu Lys Gly Leu Val Ser Asp Glu Ala Val Asp Ala Leu Val Glu
305                 310                 315                 320

Lys Ile Ala Glu Asn Ser His Gly Glu Ser Lys Ala Ala Thr Gly Ala
                325                 330                 335

Ala Ala Ser Asn Leu Asp Leu Tyr Gln Val Asn Cys Thr Tyr Tyr Ser
            340                 345                 350

Ala Leu Gly Cys Asn Asp Gln Gln Tyr Leu Ala Ala Arg Ala Val Gln
        355                 360                 365

Phe Phe Leu Pro Gly Val Pro Gln Val Tyr Tyr Val Gly Ala Leu Ala
        370                 375                 380

Gly Arg Asn Asp Met Thr Leu Leu Lys Glu Thr Gly Val Gly Arg Asp
385                 390                 395                 400

Ile Asn Arg His Tyr Tyr Ser Val Ala Glu Ile Asp Glu Asp Leu Lys
                405                 410                 415

Arg Pro Val Val Arg Ala Leu Asn Asp Leu Ala Lys Phe Arg Asn Asp
            420                 425                 430

Cys Pro Ala Phe Asp Gly Glu Phe Thr Trp Glu Arg Asp Gly Gln Asp
        435                 440                 445

Ser Val Thr Leu Thr Trp Thr Asn Gly Asp Ser His Thr Ser Leu Thr
        450                 455                 460

Phe Gln Pro Asn Leu Gly Thr Gln Asp Ala Gly Ala Pro Val Ala Thr
465                 470                 475                 480

Leu Thr Trp Asn Asp Ala Asp Gly Glu His Thr Ser Ala Asp Leu Leu
                485                 490                 495

Thr Asn Pro Pro Val Tyr Arg Lys
            500

<210> SEQ ID NO 10
<211> LENGTH: 504
<212> TYPE: PRT
<213> ORGANISM: Artificial Sequence
<220> FEATURE:
<223> OTHER INFORMATION: >A148R

<400> SEQUENCE: 10

Met Lys Asn Lys Val Gln Met Ile Thr Tyr Ala Asn Arg Leu Gly Asp
1               5                   10                  15

Gly Asn Leu Ala Ser Leu Thr Glu Ile Leu Arg Thr Arg Phe Asn Gly
            20                  25                  30

Ala Tyr Glu Gly Val His Ile Leu Pro Phe Phe Thr Pro Phe Asp Gly
        35                  40                  45

Ala Asp Ala Gly Phe Asp Pro Ile Asp His Thr Lys Val Asp Pro Arg
    50                  55                  60

Leu Gly Asp Trp Asn Asp Ile Ala Glu Leu Ser Lys Thr His Asp Ile
65                  70                  75                  80

Met Val Asp Ala Ile Val Asn His Met Ser Trp Glu Ser Ala Gln Phe
                85                  90                  95

Gln Asp Val Met Lys Asn Gly Glu Glu Ser Glu Tyr Tyr Pro Met Phe
            100                 105                 110

Leu Thr Met Ser Ser Val Phe Pro Leu Gly Ala Ser Glu Glu Asp Leu
```

```
                115                 120                 125
Ala Gly Ile Tyr Arg Pro Arg Pro Gly Leu Pro Phe Thr Pro Tyr Arg
130                 135                 140

Phe Gly Asn Arg Asn Arg Leu Val Trp Thr Thr Phe Thr Pro Gln Gln
145                 150                 155                 160

Val Asp Ile Asp Thr Asp Ser Asp Lys Gly Trp Glu Tyr Leu Met Ser
                165                 170                 175

Ile Phe Asp Gln Met Ser Lys Ser His Val Ser Gln Ile Arg Leu Asp
                180                 185                 190

Ala Val Gly Tyr Gly Ala Lys Glu Ala Gly Thr Ser Cys Phe Met Thr
            195                 200                 205

Pro Lys Thr Phe Arg Leu Ile Ser Arg Leu Arg Glu Glu Gly Ala Lys
210                 215                 220

Arg Cys Leu Glu Ile Leu Ile Glu Val His Ser Tyr Tyr Lys Lys Gln
225                 230                 235                 240

Ile Glu Ile Ala Ser Lys Val Asp Arg Val Tyr Asp Phe Ala Leu Pro
                245                 250                 255

Pro Leu Leu Leu His Ser Leu Phe Thr Gly Asp Val Asp Ala Leu Ser
            260                 265                 270

His Trp Ile Asp Ile Arg Pro Asn Asn Ala Val Thr Val Leu Asp Thr
        275                 280                 285

His Asp Gly Ile Gly Val Ile Asp Ile Gly Ser Asp Gln Gln Asp Arg
290                 295                 300

Ser Leu Lys Gly Leu Val Ser Asp Glu Ala Val Asp Ala Leu Val Glu
305                 310                 315                 320

Lys Ile Ala Glu Asn Ser His Gly Glu Ser Lys Ala Ala Thr Gly Ala
                325                 330                 335

Ala Ala Ser Asn Leu Asp Leu Tyr Gln Val Asn Cys Thr Tyr Tyr Ser
            340                 345                 350

Ala Leu Gly Cys Asn Asp Gln Gln Tyr Leu Ala Ala Arg Ala Val Gln
        355                 360                 365

Phe Phe Leu Pro Gly Val Pro Gln Val Tyr Tyr Val Gly Ala Leu Ala
370                 375                 380

Gly Arg Asn Asp Met Thr Leu Leu Lys Glu Thr Gly Val Gly Arg Asp
385                 390                 395                 400

Ile Asn Arg His Tyr Tyr Ser Val Ala Glu Ile Asp Glu Asp Leu Lys
                405                 410                 415

Arg Pro Val Val Arg Ala Leu Asn Asp Leu Ala Lys Phe Arg Asn Asp
            420                 425                 430

Cys Pro Ala Phe Asp Gly Glu Phe Thr Trp Glu Arg Asp Gly Gln Asp
        435                 440                 445

Ser Val Thr Leu Thr Trp Thr Asn Gly Asp Ser His Thr Ser Leu Thr
    450                 455                 460

Phe Gln Pro Asn Leu Gly Thr Gln Asp Ala Gly Ala Pro Val Ala Thr
465                 470                 475                 480

Leu Thr Trp Asn Asp Ala Asp Gly Glu His Thr Ser Ala Asp Leu Leu
                485                 490                 495

Thr Asn Pro Pro Val Tyr Arg Lys
            500

<210> SEQ ID NO 11
<211> LENGTH: 504
<212> TYPE: PRT
<213> ORGANISM: Artificial Sequence
```

<220> FEATURE:
<223> OTHER INFORMATION: >A148K

<400> SEQUENCE: 11

```
Met Lys Asn Lys Val Gln Met Ile Thr Tyr Ala Asn Arg Leu Gly Asp
1               5                   10                  15
Gly Asn Leu Ala Ser Leu Thr Glu Ile Leu Arg Thr Arg Phe Asn Gly
            20                  25                  30
Ala Tyr Glu Gly Val His Ile Leu Pro Phe Phe Thr Pro Phe Asp Gly
        35                  40                  45
Ala Asp Ala Gly Phe Asp Pro Ile Asp His Thr Lys Val Asp Pro Arg
    50                  55                  60
Leu Gly Asp Trp Asn Asp Ile Ala Glu Leu Ser Lys Thr His Asp Ile
65                  70                  75                  80
Met Val Asp Ala Ile Val Asn His Met Ser Trp Glu Ser Ala Gln Phe
                85                  90                  95
Gln Asp Val Met Lys Asn Gly Glu Glu Ser Glu Tyr Tyr Pro Met Phe
            100                 105                 110
Leu Thr Met Ser Ser Val Phe Pro Leu Gly Ala Ser Glu Glu Asp Leu
        115                 120                 125
Ala Gly Ile Tyr Arg Pro Arg Pro Gly Leu Pro Phe Thr Pro Tyr Arg
    130                 135                 140
Phe Gly Asn Lys Asn Arg Leu Val Trp Thr Thr Phe Thr Pro Gln Gln
145                 150                 155                 160
Val Asp Ile Asp Thr Asp Ser Asp Lys Gly Trp Glu Tyr Leu Met Ser
                165                 170                 175
Ile Phe Asp Gln Met Ser Lys Ser His Val Ser Gln Ile Arg Leu Asp
            180                 185                 190
Ala Val Gly Tyr Gly Ala Lys Glu Ala Gly Thr Ser Cys Phe Met Thr
        195                 200                 205
Pro Lys Thr Phe Arg Leu Ile Ser Arg Leu Arg Glu Glu Gly Ala Lys
    210                 215                 220
Arg Cys Leu Glu Ile Leu Ile Glu Val His Ser Tyr Tyr Lys Lys Gln
225                 230                 235                 240
Ile Glu Ile Ala Ser Lys Val Asp Arg Val Tyr Asp Phe Ala Leu Pro
                245                 250                 255
Pro Leu Leu Leu His Ser Leu Phe Thr Gly Asp Val Ala Leu Ser
    260                 265                 270
His Trp Ile Asp Ile Arg Pro Asn Asn Ala Val Thr Val Leu Asp Thr
275                 280                 285
His Asp Gly Ile Gly Val Ile Asp Ile Gly Ser Asp Gln Gln Asp Arg
                290                 295                 300
Ser Leu Lys Gly Leu Val Ser Asp Glu Ala Val Asp Ala Leu Val Glu
305                 310                 315                 320
Lys Ile Ala Glu Asn Ser His Gly Glu Ser Lys Ala Ala Thr Gly Ala
                325                 330                 335
Ala Ala Ser Asn Leu Asp Leu Tyr Gln Val Asn Cys Thr Tyr Tyr Ser
            340                 345                 350
Ala Leu Gly Cys Asn Asp Gln Gln Tyr Leu Ala Ala Arg Ala Val Gln
        355                 360                 365
Phe Phe Leu Pro Gly Val Pro Gln Val Tyr Tyr Val Gly Ala Leu Ala
    370                 375                 380
Gly Arg Asn Asp Met Thr Leu Leu Lys Glu Thr Gly Val Gly Arg Asp
385                 390                 395                 400
```

-continued

```
Ile Asn Arg His Tyr Tyr Ser Val Ala Glu Ile Asp Glu Asp Leu Lys
            405                 410                 415

Arg Pro Val Val Arg Ala Leu Asn Asp Leu Ala Lys Phe Arg Asn Asp
        420                 425                 430

Cys Pro Ala Phe Asp Gly Glu Phe Thr Trp Glu Arg Asp Gly Gln Asp
            435                 440                 445

Ser Val Thr Leu Thr Trp Thr Asn Gly Asp Ser His Thr Ser Leu Thr
450                 455                 460

Phe Gln Pro Asn Leu Gly Thr Gln Asp Ala Gly Ala Pro Val Ala Thr
465                 470                 475                 480

Leu Thr Trp Asn Asp Ala Asp Gly Glu His Thr Ser Ala Asp Leu Leu
                485                 490                 495

Thr Asn Pro Pro Val Tyr Arg Lys
            500

<210> SEQ ID NO 12
<211> LENGTH: 504
<212> TYPE: PRT
<213> ORGANISM: Artificial Sequence
<220> FEATURE:
<223> OTHER INFORMATION: >T157D

<400> SEQUENCE: 12

Met Lys Asn Lys Val Gln Met Ile Thr Tyr Ala Asn Arg Leu Gly Asp
1               5                   10                  15

Gly Asn Leu Ala Ser Leu Thr Glu Ile Leu Arg Thr Arg Phe Asn Gly
            20                  25                  30

Ala Tyr Glu Gly Val His Ile Leu Pro Phe Phe Thr Pro Phe Asp Gly
        35                  40                  45

Ala Asp Ala Gly Phe Asp Pro Ile Asp His Thr Lys Val Asp Pro Arg
    50                  55                  60

Leu Gly Asp Trp Asn Asp Ile Ala Glu Leu Ser Lys Thr His Asp Ile
65                  70                  75                  80

Met Val Asp Ala Ile Val Asn His Met Ser Trp Glu Ser Ala Gln Phe
                85                  90                  95

Gln Asp Val Met Lys Asn Gly Glu Glu Ser Glu Tyr Tyr Pro Met Phe
            100                 105                 110

Leu Thr Met Ser Ser Val Phe Pro Leu Gly Ala Ser Glu Glu Asp Leu
        115                 120                 125

Ala Gly Ile Tyr Arg Pro Arg Pro Gly Leu Pro Phe Thr Pro Tyr Arg
    130                 135                 140

Phe Gly Asn Ala Asn Arg Leu Val Trp Thr Thr Phe Asp Pro Gln Gln
145                 150                 155                 160

Val Asp Ile Asp Thr Asp Ser Asp Lys Gly Trp Glu Tyr Leu Met Ser
                165                 170                 175

Ile Phe Asp Gln Met Ser Lys Ser His Val Ser Gln Ile Arg Leu Asp
            180                 185                 190

Ala Val Gly Tyr Gly Ala Lys Glu Ala Gly Thr Ser Cys Phe Met Thr
        195                 200                 205

Pro Lys Thr Phe Arg Leu Ile Ser Arg Leu Arg Glu Glu Gly Ala Lys
    210                 215                 220

Arg Cys Leu Glu Ile Leu Ile Glu Val His Ser Tyr Tyr Lys Lys Gln
225                 230                 235                 240

Ile Glu Ile Ala Ser Lys Val Asp Arg Val Tyr Asp Phe Ala Leu Pro
                245                 250                 255
```

Pro Leu Leu Leu His Ser Leu Phe Thr Gly Asp Val Asp Ala Leu Ser
                260                 265                 270

His Trp Ile Asp Ile Arg Pro Asn Asn Ala Val Thr Val Leu Asp Thr
            275                 280                 285

His Asp Gly Ile Gly Val Ile Asp Ile Gly Ser Asp Gln Gln Asp Arg
        290                 295                 300

Ser Leu Lys Gly Leu Val Ser Asp Glu Ala Val Asp Ala Leu Val Glu
305                 310                 315                 320

Lys Ile Ala Glu Asn Ser His Gly Glu Ser Lys Ala Ala Thr Gly Ala
                325                 330                 335

Ala Ala Ser Asn Leu Asp Leu Tyr Gln Val Asn Cys Thr Tyr Tyr Ser
            340                 345                 350

Ala Leu Gly Cys Asn Asp Gln Gln Tyr Leu Ala Ala Arg Ala Val Gln
        355                 360                 365

Phe Phe Leu Pro Gly Val Pro Gln Val Tyr Val Gly Ala Leu Ala
        370                 375                 380

Gly Arg Asn Asp Met Thr Leu Leu Lys Glu Thr Gly Val Gly Arg Asp
385                 390                 395                 400

Ile Asn Arg His Tyr Tyr Ser Val Ala Glu Ile Asp Glu Asp Leu Lys
                405                 410                 415

Arg Pro Val Val Arg Ala Leu Asn Asp Leu Ala Lys Phe Arg Asn Asp
            420                 425                 430

Cys Pro Ala Phe Asp Gly Glu Phe Thr Trp Glu Arg Asp Gly Gln Asp
        435                 440                 445

Ser Val Thr Leu Thr Trp Thr Asn Gly Asp Ser His Thr Ser Leu Thr
450                 455                 460

Phe Gln Pro Asn Leu Gly Thr Gln Asp Ala Gly Ala Pro Val Ala Thr
465                 470                 475                 480

Leu Thr Trp Asn Asp Ala Asp Gly Glu His Thr Ser Ala Asp Leu Leu
                485                 490                 495

Thr Asn Pro Pro Val Tyr Arg Lys
            500

```
<210> SEQ ID NO 13
<211> LENGTH: 504
<212> TYPE: PRT
<213> ORGANISM: Artificial Sequence
<220> FEATURE:
<223> OTHER INFORMATION: >Q188Y

<400> SEQUENCE: 13
```

Met Lys Asn Lys Val Gln Met Ile Thr Tyr Ala Asn Arg Leu Gly Asp
1               5                   10                  15

Gly Asn Leu Ala Ser Leu Thr Glu Ile Leu Arg Thr Arg Phe Asn Gly
            20                  25                  30

Ala Tyr Glu Gly Val His Ile Leu Pro Phe Phe Thr Pro Phe Asp Gly
        35                  40                  45

Ala Asp Ala Gly Phe Asp Pro Ile Asp His Thr Lys Val Asp Pro Arg
    50                  55                  60

Leu Gly Asp Trp Asn Asp Ile Ala Glu Leu Ser Lys Thr His Asp Ile
65                  70                  75                  80

Met Val Asp Ala Ile Val Asn His Met Ser Trp Glu Ser Ala Gln Phe
                85                  90                  95

Gln Asp Val Met Lys Asn Gly Glu Glu Ser Glu Tyr Tyr Pro Met Phe
            100                 105                 110

Leu Thr Met Ser Ser Val Phe Pro Leu Gly Ala Ser Glu Glu Asp Leu
            115                 120                 125

Ala Gly Ile Tyr Arg Pro Arg Pro Gly Leu Pro Phe Thr Pro Tyr Arg
130                 135                 140

Phe Gly Asn Ala Asn Arg Leu Val Trp Thr Thr Phe Thr Pro Gln Gln
145                 150                 155                 160

Val Asp Ile Asp Thr Asp Ser Asp Lys Gly Trp Glu Tyr Leu Met Ser
            165                 170                 175

Ile Phe Asp Gln Met Ser Lys Ser His Val Ser Tyr Ile Arg Leu Asp
            180                 185                 190

Ala Val Gly Tyr Gly Ala Lys Glu Ala Gly Thr Ser Cys Phe Met Thr
            195                 200                 205

Pro Lys Thr Phe Arg Leu Ile Ser Arg Leu Arg Glu Glu Gly Ala Lys
            210                 215                 220

Arg Cys Leu Glu Ile Leu Ile Glu Val His Ser Tyr Tyr Lys Lys Gln
225                 230                 235                 240

Ile Glu Ile Ala Ser Lys Val Asp Arg Val Tyr Asp Phe Ala Leu Pro
            245                 250                 255

Pro Leu Leu Leu His Ser Leu Phe Thr Gly Asp Val Asp Ala Leu Ser
            260                 265                 270

His Trp Ile Asp Ile Arg Pro Asn Asn Ala Val Thr Val Leu Asp Thr
            275                 280                 285

His Asp Gly Ile Gly Val Ile Asp Ile Gly Ser Asp Gln Gln Asp Arg
            290                 295                 300

Ser Leu Lys Gly Leu Val Ser Asp Glu Ala Val Asp Ala Leu Val Glu
305                 310                 315                 320

Lys Ile Ala Glu Asn Ser His Gly Glu Ser Lys Ala Ala Thr Gly Ala
            325                 330                 335

Ala Ala Ser Asn Leu Asp Leu Tyr Gln Val Asn Cys Thr Tyr Tyr Ser
            340                 345                 350

Ala Leu Gly Cys Asn Asp Gln Gln Tyr Leu Ala Ala Arg Ala Val Gln
            355                 360                 365

Phe Phe Leu Pro Gly Val Pro Gln Val Tyr Tyr Val Gly Ala Leu Ala
            370                 375                 380

Gly Arg Asn Asp Met Thr Leu Leu Lys Glu Thr Gly Val Gly Arg Asp
385                 390                 395                 400

Ile Asn Arg His Tyr Tyr Ser Val Ala Glu Ile Asp Glu Asp Leu Lys
            405                 410                 415

Arg Pro Val Val Arg Ala Leu Asn Asp Leu Ala Lys Phe Arg Asn Asp
            420                 425                 430

Cys Pro Ala Phe Asp Gly Glu Phe Thr Trp Glu Arg Asp Gly Gln Asp
            435                 440                 445

Ser Val Thr Leu Thr Trp Thr Asn Gly Asp Ser His Thr Ser Leu Thr
450                 455                 460

Phe Gln Pro Asn Leu Gly Thr Gln Asp Ala Gly Ala Pro Val Ala Thr
465                 470                 475                 480

Leu Thr Trp Asn Asp Ala Asp Gly Glu His Thr Ser Ala Asp Leu Leu
            485                 490                 495

Thr Asn Pro Pro Val Tyr Arg Lys
            500

<210> SEQ ID NO 14
<211> LENGTH: 504

<212> TYPE: PRT
<213> ORGANISM: Artificial Sequence
<220> FEATURE:
<223> OTHER INFORMATION: >I231V

<400> SEQUENCE: 14

```
Met Lys Asn Lys Val Gln Met Ile Thr Tyr Ala Asn Arg Leu Gly Asp
1               5                   10                  15

Gly Asn Leu Ala Ser Leu Thr Glu Ile Leu Arg Thr Arg Phe Asn Gly
                20                  25                  30

Ala Tyr Glu Gly Val His Ile Leu Pro Phe Phe Thr Pro Phe Asp Gly
            35                  40                  45

Ala Asp Ala Gly Phe Asp Pro Ile Asp His Thr Lys Val Asp Pro Arg
    50                  55                  60

Leu Gly Asp Trp Asn Asp Ile Ala Glu Leu Ser Lys Thr His Asp Ile
65                  70                  75                  80

Met Val Asp Ala Ile Val Asn His Met Ser Trp Glu Ser Ala Gln Phe
                85                  90                  95

Gln Asp Val Met Lys Asn Gly Glu Glu Ser Glu Tyr Tyr Pro Met Phe
                100                 105                 110

Leu Thr Met Ser Ser Val Phe Pro Leu Gly Ala Ser Glu Glu Asp Leu
            115                 120                 125

Ala Gly Ile Tyr Arg Pro Arg Pro Gly Leu Pro Phe Thr Pro Tyr Arg
        130                 135                 140

Phe Gly Asn Ala Asn Arg Leu Val Trp Thr Thr Phe Thr Pro Gln Gln
145                 150                 155                 160

Val Asp Ile Asp Thr Asp Ser Asp Lys Gly Trp Glu Tyr Leu Met Ser
                165                 170                 175

Ile Phe Asp Gln Met Ser Lys Ser His Val Ser Gln Ile Arg Leu Asp
                180                 185                 190

Ala Val Gly Tyr Gly Ala Lys Glu Ala Gly Thr Ser Cys Phe Met Thr
            195                 200                 205

Pro Lys Thr Phe Arg Leu Ile Ser Arg Leu Arg Glu Glu Gly Ala Lys
        210                 215                 220

Arg Cys Leu Glu Ile Leu Val Glu Val His Ser Tyr Tyr Lys Lys Gln
225                 230                 235                 240

Ile Glu Ile Ala Ser Lys Val Asp Arg Val Tyr Asp Phe Ala Leu Pro
                245                 250                 255

Pro Leu Leu Leu His Ser Leu Phe Thr Gly Asp Val Asp Ala Leu Ser
                260                 265                 270

His Trp Ile Asp Ile Arg Pro Asn Asn Ala Val Thr Val Leu Asp Thr
            275                 280                 285

His Asp Gly Ile Gly Val Ile Asp Ile Gly Ser Asp Gln Gln Asp Arg
        290                 295                 300

Ser Leu Lys Gly Leu Val Ser Asp Glu Ala Val Asp Ala Leu Val Glu
305                 310                 315                 320

Lys Ile Ala Glu Asn Ser His Gly Glu Ser Lys Ala Ala Thr Gly Ala
                325                 330                 335

Ala Ala Ser Asn Leu Asp Leu Tyr Gln Val Asn Cys Thr Tyr Tyr Ser
            340                 345                 350

Ala Leu Gly Cys Asn Asp Gln Gln Tyr Leu Ala Ala Arg Ala Val Gln
        355                 360                 365

Phe Phe Leu Pro Gly Val Pro Gln Val Tyr Tyr Val Gly Ala Leu Ala
    370                 375                 380
```

-continued

Gly Arg Asn Asp Met Thr Leu Leu Lys Glu Thr Gly Val Gly Arg Asp
385                 390                 395                 400

Ile Asn Arg His Tyr Tyr Ser Val Ala Glu Ile Asp Glu Asp Leu Lys
            405                 410                 415

Arg Pro Val Val Arg Ala Leu Asn Asp Leu Ala Lys Phe Arg Asn Asp
        420                 425                 430

Cys Pro Ala Phe Asp Gly Glu Phe Thr Trp Glu Arg Asp Gly Gln Asp
    435                 440                 445

Ser Val Thr Leu Thr Trp Thr Asn Gly Asp Ser His Thr Ser Leu Thr
450                 455                 460

Phe Gln Pro Asn Leu Gly Thr Gln Asp Ala Gly Ala Pro Val Ala Thr
465                 470                 475                 480

Leu Thr Trp Asn Asp Ala Asp Gly Glu His Thr Ser Ala Asp Leu Leu
                485                 490                 495

Thr Asn Pro Pro Val Tyr Arg Lys
            500

<210> SEQ ID NO 15
<211> LENGTH: 504
<212> TYPE: PRT
<213> ORGANISM: Artificial Sequence
<220> FEATURE:
<223> OTHER INFORMATION: >L371A

<400> SEQUENCE: 15

Met Lys Asn Lys Val Gln Met Ile Thr Tyr Ala Asn Arg Leu Gly Asp
1               5                   10                  15

Gly Asn Leu Ala Ser Leu Thr Glu Ile Leu Arg Thr Arg Phe Asn Gly
            20                  25                  30

Ala Tyr Glu Gly Val His Ile Leu Pro Phe Phe Thr Pro Phe Asp Gly
        35                  40                  45

Ala Asp Ala Gly Phe Asp Pro Ile Asp His Thr Lys Val Asp Pro Arg
    50                  55                  60

Leu Gly Asp Trp Asn Asp Ile Ala Glu Leu Ser Lys Thr His Asp Ile
65                  70                  75                  80

Met Val Asp Ala Ile Val Asn His Met Ser Trp Glu Ser Ala Gln Phe
                85                  90                  95

Gln Asp Val Met Lys Asn Gly Glu Glu Ser Glu Tyr Tyr Pro Met Phe
            100                 105                 110

Leu Thr Met Ser Ser Val Phe Pro Leu Gly Ala Ser Glu Glu Asp Leu
        115                 120                 125

Ala Gly Ile Tyr Arg Pro Arg Pro Gly Leu Pro Phe Thr Pro Tyr Arg
    130                 135                 140

Phe Gly Asn Ala Asn Arg Leu Val Trp Thr Thr Phe Thr Pro Gln Gln
145                 150                 155                 160

Val Asp Ile Asp Thr Asp Ser Asp Lys Gly Trp Glu Tyr Leu Met Ser
                165                 170                 175

Ile Phe Asp Gln Met Ser Lys Ser His Val Ser Gln Ile Arg Leu Asp
            180                 185                 190

Ala Val Gly Tyr Gly Ala Lys Glu Ala Gly Thr Ser Cys Phe Met Thr
        195                 200                 205

Pro Lys Thr Phe Arg Leu Ile Ser Arg Leu Arg Glu Glu Gly Ala Lys
    210                 215                 220

Arg Cys Leu Glu Ile Leu Ile Glu Val His Ser Tyr Tyr Lys Lys Gln
225                 230                 235                 240

```
Ile Glu Ile Ala Ser Lys Val Asp Arg Val Tyr Asp Phe Ala Leu Pro
                245                 250                 255

Pro Leu Leu Leu His Ser Leu Phe Thr Gly Asp Val Asp Ala Leu Ser
            260                 265                 270

His Trp Ile Asp Ile Arg Pro Asn Asn Ala Val Thr Val Leu Asp Thr
        275                 280                 285

His Asp Gly Ile Gly Val Ile Asp Ile Gly Ser Asp Gln Gln Asp Arg
    290                 295                 300

Ser Leu Lys Gly Leu Val Ser Asp Glu Ala Val Asp Ala Leu Val Glu
305                 310                 315                 320

Lys Ile Ala Glu Asn Ser His Gly Glu Ser Lys Ala Ala Thr Gly Ala
                325                 330                 335

Ala Ala Ser Asn Leu Asp Leu Tyr Gln Val Asn Cys Thr Tyr Tyr Ser
            340                 345                 350

Ala Leu Gly Cys Asn Asp Gln Gln Tyr Leu Ala Ala Arg Ala Val Gln
        355                 360                 365

Phe Phe Ala Pro Gly Val Pro Gln Val Tyr Tyr Val Gly Ala Leu Ala
    370                 375                 380

Gly Arg Asn Asp Met Thr Leu Leu Lys Glu Thr Gly Val Gly Arg Asp
385                 390                 395                 400

Ile Asn Arg His Tyr Tyr Ser Val Ala Glu Ile Asp Glu Asp Leu Lys
                405                 410                 415

Arg Pro Val Val Arg Ala Leu Asn Asp Leu Ala Lys Phe Arg Asn Asp
            420                 425                 430

Cys Pro Ala Phe Asp Gly Glu Phe Thr Trp Glu Arg Asp Gly Gln Asp
        435                 440                 445

Ser Val Thr Leu Thr Trp Thr Asn Gly Asp Ser His Thr Ser Leu Thr
    450                 455                 460

Phe Gln Pro Asn Leu Gly Thr Gln Asp Ala Gly Ala Pro Val Ala Thr
465                 470                 475                 480

Leu Thr Trp Asn Asp Ala Asp Gly Glu His Thr Ser Ala Asp Leu Leu
                485                 490                 495

Thr Asn Pro Pro Val Tyr Arg Lys
                500

<210> SEQ ID NO 16
<211> LENGTH: 504
<212> TYPE: PRT
<213> ORGANISM: Artificial Sequence
<220> FEATURE:
<223> OTHER INFORMATION: >T461G

<400> SEQUENCE: 16

Met Lys Asn Lys Val Gln Met Ile Thr Tyr Ala Asn Arg Leu Gly Asp
1               5                   10                  15

Gly Asn Leu Ala Ser Leu Thr Glu Ile Leu Arg Thr Arg Phe Asn Gly
            20                  25                  30

Ala Tyr Glu Gly Val His Ile Leu Pro Phe Phe Thr Pro Phe Asp Gly
        35                  40                  45

Ala Asp Ala Gly Phe Asp Pro Ile Asp His Thr Lys Val Asp Pro Arg
    50                  55                  60

Leu Gly Asp Trp Asn Asp Ile Ala Glu Leu Ser Lys Thr His Asp Ile
65                  70                  75                  80

Met Val Asp Ala Ile Val Asn His Met Ser Trp Glu Ser Ala Gln Phe
                85                  90                  95
```

```
Gln Asp Val Met Lys Asn Gly Glu Glu Ser Glu Tyr Tyr Pro Met Phe
                100                 105                 110
Leu Thr Met Ser Ser Val Phe Pro Leu Gly Ala Ser Glu Glu Asp Leu
            115                 120                 125
Ala Gly Ile Tyr Arg Pro Arg Pro Gly Leu Pro Phe Thr Pro Tyr Arg
        130                 135                 140
Phe Gly Asn Ala Asn Arg Leu Val Trp Thr Thr Phe Thr Pro Gln Gln
145                 150                 155                 160
Val Asp Ile Asp Thr Asp Ser Asp Lys Gly Trp Glu Tyr Leu Met Ser
                165                 170                 175
Ile Phe Asp Gln Met Ser Lys Ser His Val Ser Gln Ile Arg Leu Asp
            180                 185                 190
Ala Val Gly Tyr Gly Ala Lys Glu Ala Gly Thr Ser Cys Phe Met Thr
        195                 200                 205
Pro Lys Thr Phe Arg Leu Ile Ser Arg Leu Arg Glu Glu Gly Ala Lys
    210                 215                 220
Arg Cys Leu Glu Ile Leu Ile Glu Val His Ser Tyr Tyr Lys Lys Gln
225                 230                 235                 240
Ile Glu Ile Ala Ser Lys Val Asp Arg Val Tyr Asp Phe Ala Leu Pro
                245                 250                 255
Pro Leu Leu Leu His Ser Leu Phe Thr Gly Asp Val Asp Ala Leu Ser
            260                 265                 270
His Trp Ile Asp Ile Arg Pro Asn Asn Ala Val Thr Val Leu Asp Thr
        275                 280                 285
His Asp Gly Ile Gly Val Ile Asp Ile Gly Ser Asp Gln Gln Asp Arg
    290                 295                 300
Ser Leu Lys Gly Leu Val Ser Asp Glu Ala Val Asp Ala Leu Val Glu
305                 310                 315                 320
Lys Ile Ala Glu Asn Ser His Gly Glu Ser Lys Ala Ala Thr Gly Ala
                325                 330                 335
Ala Ala Ser Asn Leu Asp Leu Tyr Gln Val Asn Cys Thr Tyr Tyr Ser
            340                 345                 350
Ala Leu Gly Cys Asn Asp Gln Gln Tyr Leu Ala Ala Arg Ala Val Gln
        355                 360                 365
Phe Phe Leu Pro Gly Val Pro Gln Val Tyr Tyr Val Gly Ala Leu Ala
    370                 375                 380
Gly Arg Asn Asp Met Thr Leu Leu Lys Glu Thr Gly Val Gly Arg Asp
385                 390                 395                 400
Ile Asn Arg His Tyr Tyr Ser Val Ala Glu Ile Asp Glu Asp Leu Lys
                405                 410                 415
Arg Pro Val Val Arg Ala Leu Asn Asp Leu Ala Lys Phe Arg Asn Asp
            420                 425                 430
Cys Pro Ala Phe Asp Gly Glu Phe Thr Trp Glu Arg Asp Gly Gln Asp
        435                 440                 445
Ser Val Thr Leu Thr Trp Thr Asn Gly Asp Ser His Gly Ser Leu Thr
    450                 455                 460
Phe Gln Pro Asn Leu Gly Thr Gln Asp Ala Gly Ala Pro Val Ala Thr
465                 470                 475                 480
Leu Thr Trp Asn Asp Ala Asp Gly Glu His Thr Ser Ala Asp Leu Leu
                485                 490                 495
Thr Asn Pro Pro Val Tyr Arg Lys
            500
```

```
<210> SEQ ID NO 17
<211> LENGTH: 504
<212> TYPE: PRT
<213> ORGANISM: Artificial Sequence
<220> FEATURE:
<223> OTHER INFORMATION: >A148K_Q188Y

<400> SEQUENCE: 17
```

| Met | Lys | Asn | Lys | Val | Gln | Met | Ile | Thr | Tyr | Ala | Asn | Arg | Leu | Gly | Asp |
|---|---|---|---|---|---|---|---|---|---|---|---|---|---|---|---|
| 1 | | | | 5 | | | | | 10 | | | | | 15 | |

| Gly | Asn | Leu | Ala | Ser | Leu | Thr | Glu | Ile | Leu | Arg | Thr | Arg | Phe | Asn | Gly |
|---|---|---|---|---|---|---|---|---|---|---|---|---|---|---|---|
| | | | 20 | | | | | 25 | | | | | 30 | | |

| Ala | Tyr | Glu | Gly | Val | His | Ile | Leu | Pro | Phe | Phe | Thr | Pro | Phe | Asp | Gly |
|---|---|---|---|---|---|---|---|---|---|---|---|---|---|---|---|
| | | | 35 | | | | | 40 | | | | | 45 | | |

| Ala | Asp | Ala | Gly | Phe | Asp | Pro | Ile | Asp | His | Thr | Lys | Val | Asp | Pro | Arg |
|---|---|---|---|---|---|---|---|---|---|---|---|---|---|---|---|
| | | 50 | | | | | 55 | | | | | 60 | | | |

| Leu | Gly | Asp | Trp | Asn | Asp | Ile | Ala | Glu | Leu | Ser | Lys | Thr | His | Asp | Ile |
|---|---|---|---|---|---|---|---|---|---|---|---|---|---|---|---|
| 65 | | | | | 70 | | | | | 75 | | | | | 80 |

| Met | Val | Asp | Ala | Ile | Val | Asn | His | Met | Ser | Trp | Glu | Ser | Ala | Gln | Phe |
|---|---|---|---|---|---|---|---|---|---|---|---|---|---|---|---|
| | | | | 85 | | | | | 90 | | | | | 95 | |

| Gln | Asp | Val | Met | Lys | Asn | Gly | Glu | Glu | Ser | Glu | Tyr | Tyr | Pro | Met | Phe |
|---|---|---|---|---|---|---|---|---|---|---|---|---|---|---|---|
| | | | 100 | | | | | 105 | | | | | 110 | | |

| Leu | Thr | Met | Ser | Ser | Val | Phe | Pro | Leu | Gly | Ala | Ser | Glu | Glu | Asp | Leu |
|---|---|---|---|---|---|---|---|---|---|---|---|---|---|---|---|
| | | 115 | | | | | 120 | | | | | 125 | | | |

| Ala | Gly | Ile | Tyr | Arg | Pro | Arg | Pro | Gly | Leu | Pro | Phe | Thr | Pro | Tyr | Arg |
|---|---|---|---|---|---|---|---|---|---|---|---|---|---|---|---|
| | | 130 | | | | | 135 | | | | | 140 | | | |

| Phe | Gly | Asn | Lys | Asn | Arg | Leu | Val | Trp | Thr | Thr | Phe | Thr | Pro | Gln | Gln |
|---|---|---|---|---|---|---|---|---|---|---|---|---|---|---|---|
| 145 | | | | | 150 | | | | | 155 | | | | | 160 |

| Val | Asp | Ile | Asp | Thr | Asp | Ser | Asp | Lys | Gly | Trp | Glu | Tyr | Leu | Met | Ser |
|---|---|---|---|---|---|---|---|---|---|---|---|---|---|---|---|
| | | | | 165 | | | | | 170 | | | | | 175 | |

| Ile | Phe | Asp | Gln | Met | Ser | Lys | Ser | His | Val | Ser | Tyr | Ile | Arg | Leu | Asp |
|---|---|---|---|---|---|---|---|---|---|---|---|---|---|---|---|
| | | | 180 | | | | | 185 | | | | | 190 | | |

| Ala | Val | Gly | Tyr | Gly | Ala | Lys | Glu | Ala | Gly | Thr | Ser | Cys | Phe | Met | Thr |
|---|---|---|---|---|---|---|---|---|---|---|---|---|---|---|---|
| | | 195 | | | | | 200 | | | | | 205 | | | |

| Pro | Lys | Thr | Phe | Arg | Leu | Ile | Ser | Arg | Leu | Arg | Glu | Glu | Gly | Ala | Lys |
|---|---|---|---|---|---|---|---|---|---|---|---|---|---|---|---|
| | 210 | | | | | 215 | | | | | 220 | | | | |

| Arg | Cys | Leu | Glu | Ile | Leu | Ile | Glu | Val | His | Ser | Tyr | Tyr | Lys | Lys | Gln |
|---|---|---|---|---|---|---|---|---|---|---|---|---|---|---|---|
| 225 | | | | | 230 | | | | | 235 | | | | | 240 |

| Ile | Glu | Ile | Ala | Ser | Lys | Val | Asp | Arg | Val | Tyr | Asp | Phe | Ala | Leu | Pro |
|---|---|---|---|---|---|---|---|---|---|---|---|---|---|---|---|
| | | | | 245 | | | | | 250 | | | | | 255 | |

| Pro | Leu | Leu | Leu | His | Ser | Leu | Phe | Thr | Gly | Asp | Val | Asp | Ala | Leu | Ser |
|---|---|---|---|---|---|---|---|---|---|---|---|---|---|---|---|
| | | | 260 | | | | | 265 | | | | | 270 | | |

| His | Trp | Ile | Asp | Ile | Arg | Pro | Asn | Asn | Ala | Val | Thr | Val | Leu | Asp | Thr |
|---|---|---|---|---|---|---|---|---|---|---|---|---|---|---|---|
| | | 275 | | | | | 280 | | | | | 285 | | | |

| His | Asp | Gly | Ile | Gly | Val | Ile | Asp | Ile | Gly | Ser | Asp | Gln | Gln | Asp | Arg |
|---|---|---|---|---|---|---|---|---|---|---|---|---|---|---|---|
| | 290 | | | | | 295 | | | | | 300 | | | | |

| Ser | Leu | Lys | Gly | Leu | Val | Ser | Asp | Glu | Ala | Val | Asp | Ala | Leu | Val | Glu |
|---|---|---|---|---|---|---|---|---|---|---|---|---|---|---|---|
| 305 | | | | | 310 | | | | | 315 | | | | | 320 |

| Lys | Ile | Ala | Glu | Asn | Ser | His | Gly | Glu | Ser | Lys | Ala | Ala | Thr | Gly | Ala |
|---|---|---|---|---|---|---|---|---|---|---|---|---|---|---|---|
| | | | | 325 | | | | | 330 | | | | | 335 | |

| Ala | Ala | Ser | Asn | Leu | Asp | Leu | Tyr | Gln | Val | Asn | Cys | Thr | Tyr | Tyr | Ser |
|---|---|---|---|---|---|---|---|---|---|---|---|---|---|---|---|
| | | | 340 | | | | | 345 | | | | | 350 | | |

| Ala | Leu | Gly | Cys | Asn | Asp | Gln | Gln | Tyr | Leu | Ala | Ala | Arg | Ala | Val | Gln |
|---|---|---|---|---|---|---|---|---|---|---|---|---|---|---|---|
| | | 355 | | | | | 360 | | | | | 365 | | | |

| Phe | Phe | Leu | Pro | Gly | Val | Pro | Gln | Val | Tyr | Tyr | Val | Gly | Ala | Leu | Ala |

```
            370                 375                 380
Gly Arg Asn Asp Met Thr Leu Leu Lys Glu Thr Gly Val Gly Arg Asp
385                 390                 395                 400

Ile Asn Arg His Tyr Tyr Ser Val Ala Glu Ile Asp Glu Asp Leu Lys
                405                 410                 415

Arg Pro Val Val Arg Ala Leu Asn Asp Leu Ala Lys Phe Arg Asn Asp
                420                 425                 430

Cys Pro Ala Phe Asp Gly Glu Phe Thr Trp Glu Arg Asp Gly Gln Asp
                435                 440                 445

Ser Val Thr Leu Thr Trp Thr Asn Gly Asp Ser His Thr Ser Leu Thr
450                 455                 460

Phe Gln Pro Asn Leu Gly Thr Gln Asp Ala Gly Ala Pro Val Ala Thr
465                 470                 475                 480

Leu Thr Trp Asn Asp Ala Asp Gly Glu His Thr Ser Ala Asp Leu Leu
                485                 490                 495

Thr Asn Pro Pro Val Tyr Arg Lys
                500
```

<210> SEQ ID NO 18
<211> LENGTH: 504
<212> TYPE: PRT
<213> ORGANISM: Artificial Sequence
<220> FEATURE:
<223> OTHER INFORMATION: >A148K_T157D_Q188Y_L371A_T461G

<400> SEQUENCE: 18

```
Met Lys Asn Lys Val Gln Met Ile Thr Tyr Ala Asn Arg Leu Gly Asp
1               5                   10                  15

Gly Asn Leu Ala Ser Leu Thr Glu Ile Leu Arg Thr Arg Phe Asn Gly
                20                  25                  30

Ala Tyr Glu Gly Val His Ile Leu Pro Phe Phe Thr Pro Phe Asp Gly
            35                  40                  45

Ala Asp Ala Gly Phe Asp Pro Ile Asp His Thr Lys Val Asp Pro Arg
50                  55                  60

Leu Gly Asp Trp Asn Asp Ile Ala Glu Leu Ser Lys Thr His Asp Ile
65                  70                  75                  80

Met Val Asp Ala Ile Val Asn His Met Ser Trp Glu Ser Ala Gln Phe
                85                  90                  95

Gln Asp Val Met Lys Asn Gly Glu Glu Ser Glu Tyr Tyr Pro Met Phe
                100                 105                 110

Leu Thr Met Ser Ser Val Phe Pro Leu Gly Ala Ser Glu Glu Asp Leu
            115                 120                 125

Ala Gly Ile Tyr Arg Pro Arg Pro Gly Leu Pro Phe Thr Pro Tyr Arg
130                 135                 140

Phe Gly Asn Lys Asn Arg Leu Val Trp Thr Thr Phe Asp Pro Gln Gln
145                 150                 155                 160

Val Asp Ile Asp Thr Asp Ser Asp Lys Gly Trp Glu Tyr Leu Met Ser
                165                 170                 175

Ile Phe Asp Gln Met Ser Lys Ser His Val Ser Tyr Ile Arg Leu Asp
            180                 185                 190

Ala Val Gly Tyr Gly Ala Lys Glu Ala Gly Thr Ser Cys Phe Met Thr
            195                 200                 205

Pro Lys Thr Phe Arg Leu Ile Ser Arg Leu Arg Glu Glu Gly Ala Lys
    210                 215                 220

Arg Cys Leu Glu Ile Leu Ile Glu Val His Ser Tyr Tyr Lys Lys Gln
```

-continued

```
              225                 230                 235                 240
    Ile Glu Ile Ala Ser Lys Val Asp Arg Val Tyr Asp Phe Ala Leu Pro
                        245                 250                 255

Pro Leu Leu Leu His Ser Leu Phe Thr Gly Asp Val Asp Ala Leu Ser
                        260                 265                 270

His Trp Ile Asp Ile Arg Pro Asn Asn Ala Val Thr Val Leu Asp Thr
                275                 280                 285

His Asp Gly Ile Gly Val Ile Asp Ile Gly Ser Asp Gln Gln Asp Arg
                290                 295                 300

Ser Leu Lys Gly Leu Val Ser Asp Glu Ala Val Asp Ala Leu Val Glu
    305                 310                 315                 320

Lys Ile Ala Glu Asn Ser His Gly Glu Ser Lys Ala Ala Thr Gly Ala
                        325                 330                 335

Ala Ala Ser Asn Leu Asp Leu Tyr Gln Val Asn Cys Thr Tyr Tyr Ser
                        340                 345                 350

Ala Leu Gly Cys Asn Asp Gln Gln Tyr Leu Ala Ala Arg Ala Val Gln
                        355                 360                 365

Phe Phe Ala Pro Gly Val Pro Gln Val Tyr Tyr Val Gly Ala Leu Ala
        370                 375                 380

Gly Arg Asn Asp Met Thr Leu Leu Lys Glu Thr Gly Val Gly Arg Asp
    385                 390                 395                 400

Ile Asn Arg His Tyr Tyr Ser Val Ala Glu Ile Asp Glu Asp Leu Lys
                        405                 410                 415

Arg Pro Val Val Arg Ala Leu Asn Asp Leu Ala Lys Phe Arg Asn Asp
                        420                 425                 430

Cys Pro Ala Phe Asp Gly Glu Phe Thr Trp Glu Arg Asp Gly Gln Asp
                        435                 440                 445

Ser Val Thr Leu Thr Trp Thr Asn Gly Asp Ser His Gly Ser Leu Thr
                        450                 455                 460

Phe Gln Pro Asn Leu Gly Thr Gln Asp Ala Gly Ala Pro Val Ala Thr
    465                 470                 475                 480

Leu Thr Trp Asn Asp Ala Asp Gly Glu His Thr Ser Ala Asp Leu Leu
                        485                 490                 495

Thr Asn Pro Pro Val Tyr Arg Lys
                        500
```

SUCROSE PHOSPHORYLASE

This application is the U.S. national stage of International Patent Application No. PCT/EP2018/082854, filed Nov. 28, 2018, which claims the benefit of European Patent Application 17204146.9, filed Nov. 28, 2017.

FIELD OF THE INVENTION

The invention relates to phosphorylase enzymes, also called phosphorylases. Specifically this invention relates to certain phosphorylases, that are capable of converting, among other reactions, sucrose to fructose and alpha-D-glucose-1 phosphate ("aG1P") through phosphorolytic cleavage of the sucrose. Such sucrose phosphorylases may be also abbreviated and referred to in the following as "SP". The Sucrose Phosphorylases according to the invention are particularly useful for catalyzing the conversion of sucrose to fructose and aG1P.

BACKGROUND OF THE INVENTION

The term "sucrose phosphorylase" (SP) describes specifically enzymes that catalyse the phosphorolytic cleavage of sucrose with net retention of its anomeric configuration and by using phosphate as a glucosyl acceptor into fructose and alpha-D-glucose 1-phosphate (aG1P). Additionally, the enzymes have been described to catalyse the hydrolysis of aG1P and transglycosylation reactions involving alternative glucosyl acceptors (e.g., monosaccharides, sugar alcohols; for review see Goedl et al. Biocatal. Biotransform. 28 (2010) 10-21).

Cerdobbel et al (Protein Eng Des Sel. 2011 Nov.; 24(11): 829-34) describes single and double mutants of the sucrose phosphorylase from *Bifidobacterium adolescentis* which show either an increased thermal stability with decreased activities, or a slightly improved activity with no improvement in thermal stability. The wild-type sucrose phosphorylase from *Bifidobacterium adolescentis* has an identity of 79% to the wild-type sucrose phosphorylase from *Bifidobacterium magnum*. WO 2011/124538 describes thermally stable sucrose phosphorylase variants of the wild-type enzyme from *Bifidobacterium adolescentis*. The wild-type sucrose phosphorylase showed a residual activity of 79% after incubation for 16 h at 60° C. Through mutagenesis at one or more positions selected from positions R393, Q460, E485, D445, D446, and Q331, the thermal stability could be increased: a six-fold mutant containing the mutations R393N, Q460E, E485H, D445P, D446T, and Q331E showed the highest improvement with no apparent loss in residual activity after incubation at 60° C. for 16 h. These mutations led to a decrease in activity of up to 20%.

WO 2017/153420 discloses seven 2-4-fold mutants of the sucrose phosphorylase from *Bifidobacterium adolescentis* with mutations positions selected from the amino acid positions S21, H142, L151, H185, I295, N396, S451, D474 and T476. Two variants showed a lower thermal stability than the wild-type, while the other variants showed the same thermal stability as the wild-type enzyme.

Fuji et al (Journal of Applied Glycoscience Vol. 53 (2006) No. 2 P 91-97) showed that the single amino acids substitutions T47S, S62P, Y77H, V128L, K140M, Q144R, N155S and D249G, contributed to the enhancement of thermal stability in the sucrose phosphorylase from *Streptococcus mutans* (38% identity to the sucrose phosphorylase from *Bifidobacterium magnum*). The best variant, an 8-fold mutant, retained approx. 65% residual activity after incubation at 60° C. for 20 min.

Aerts et al (Biotechnology and Bioengineering, Vol. 110, No. 10, 2013, 2563-2572) generated three artificial sucrose phosphorylase sequences based on the most frequently occurring amino acids at their positions in a multiple sequence alignment (MSA) of known sucrose phosphorylases and homologous database sequences (consensus approach) which would be expected to result in more stable and possibly more promiscuous enzymes. One of these artificial sucrose phosphorylases, which can be considered a 84-fold mutant of the sucrose phosphorylase from *Bifidobacterium adolescentis*, showed slightly decreased activities for sucrose phosphorolysis and was also less stable. The two artificial homologues of the SP from *Streptococcus* mutants with 65 and 77 mutations, respectively, showed significantly lower activities than the wild-type enzyme while exhibiting increased stability.

Silverstein et al. (The Journal of Biological Chemistry, Vol. 242, No. 6, 1967, 1338-1346) characterized the sucrose phosphorylase from *Pseudomonas saccharophila* and determined a 67-fold higher phosphorolytic activity than hydrolytic activity.

The reaction that is catalysed by sucrose phosphorylases is reversible (equilibrium reaction) and may undergo substrate or product inhibition, depending on the specific direction of the reaction.

Sucrose phosphorylases may furthermore catalyse the hydrolysis of aG1P to glucose and inorganic phosphate and transglycosylation reactions with a wide variety of acceptor molecules.

A low hydrolytic activity of a sucrose phosphorylase enzyme is advantageous as it leads to improved product yields with respect to both the phosphorolytic cleavage of sucrose and the transglycosidation reaction. In order to obtain industrially relevant yields of a desired product, sucrose phosphorylase enzymes are required that catalyse the conversion of substrates with high specific activity and at high substrate concentration and low aG1P hydrolysis rate. Besides pure enzyme characteristics, it may be required to bias the equilibrium reaction toward production of a certain product compound by choosing optimal reaction conditions, resulting in high product yields over process time. In addition, other kinetic factors, such as substrate selectivity, $K_M$ and stereoselectivity may play an important role for overall product yields over time. Other relevant aspects may include, but are not limited to, the inhibition by other factors (e.g. crude extract components, substrate contaminants or side products), and recombinant soluble expression in suitable hosts.

Another important criterion in the industrial use of sucrose phosphorylases is a long process stability, which often correlates with a high stability at elevated temperatures, which is also referred to as a "high thermal stability", and good stability in solvents and/or at high concentrations of substrate and product, respectively. In industrial applications, process stability also may encompass chemical and physical stability, enzymatic activity in differing solvents (aqueous, non-aqueous environments, biphasic systems), and/or at a broad pH-range, e.g. from about pH 4 to about pH 11, and/or applicability with any solid supports or carriers or other processing technique.

Sucrose phosphorylase enzymes in particular are widely described for industrial processes that involve the formation of aG1P from sucrose in a first step, and wherein the aG1P in a second step is further converted into a secondary product by additional enzymes, e.g. in the production of cellobiose, trehalose, laminaribiose, and others. Most of such processes currently described use the sucrose phosphorylase from *Leuconostoc mesenteroides* or *Bifidobacterium adolescentis*, and production yields are achieved through optimal adjustment of overall process conditions.

The ratio of phosphorolytic to hydrolytic activity of the sucrose phosphorylase enzymes described in the state of the art, alone and in combination with thermal stability, therefore, is insufficient for industrial scale processes involving sucrose phosphorylases. Accordingly there is a need for obtaining enzymes that provide high activity at high sucrose concentration, a high ratio of phosphorolytic to hydrolytic activity, a high thermal stability, and which can stand long process times. There is further a demand for the selection of suitable sucrose phosphorylase enzymes having advantages compared to conventional sucrose phosphorylase enzymes, in particular with respect to high ratio of phosphorolytic to hydrolytic activity, diminished substrate inhibition, and thermal and process stabilities at high temperatures during industrial processes with high yields and high conversion rates.

It is an object of the invention to provide sucrose phosphorylase enzymes that have advantages over the sucrose phosphorylases known in the art. This object has been achieved by the subject-matter of the patent claims.

DETAILED DESCRIPTION OF THE INVENTION

The present invention relates to a sucrose phosphorylase, wherein the sucrose phosphorylase is a wild-type sucrose phosphorylase from *Bifidobacterium magnum*, characterized in that the wild-type sucrose phosphorylase from *Bifidobacterium magnum* is distinguished from other sucrose phosphorylase wild-type enzymes by a low hydrolytic activity and by an efficient production of aG1P at high sucrose concentrations.

The present invention further relates to a sucrose phosphorylase, wherein the sucrose phosphorylase is a mutant of wild-type sucrose phosphorylase from *Bifidobacterium magnum*, characterized in that the mutant sucrose phosphorylase is distinguished by an increased thermal stability in comparison to the wild-type sucrose phosphorylase.

Specifically, the sucrose phosphorylase of the invention is a mutant of wild-type sucrose phosphorylase from *Bifidobacterium magnum*, characterized in that the mutant sucrose phosphorylase is distinguished by an increased thermal stability, and by a low hydrolytic activity in comparison to the wild-type sucrose phosphorylase.

More specifically, the sucrose phosphorylase of the invention is a mutant of wild-type sucrose phosphorylase from *Bifidobacterium magnum*, characterized in that the mutant sucrose phosphorylase is distinguished by an increased thermal stability, by a low hydrolytic activity, and by an efficient production of aG1P at high sucrose concentrations in comparison to the wild-type sucrose phosphorylase.

In a first aspect, the invention relates to a sucrose phosphorylase comprising or consisting of an amino acid sequence, wherein the amino acid sequence is at least 75% homologous and/or identical to the amino acid sequence of SEQ ID NO: 1.

In a preferred embodiment of the first aspect, the sucrose phosphorylase comprises an amino acid sequence selected from the group consisting of SEQ ID NO: 1, SEQ ID NO: 2, SEQ ID NO: 3, and SEQ ID NO: 4, preferably of SEQ ID NO: 1.

In a further preferred embodiment of the first aspect, the sucrose phosphorylase consists of an amino acid sequence selected from the group consisting of SEQ ID NO: 1, SEQ ID NO: 2, SEQ ID NO: 3, and SEQ ID NO: 4, preferably of SEQ ID NO: 1.

The sucrose phosphorylase of the invention is preferably characterized in that the homology and/or identity of the amino acid sequence to SEQ ID NO: 1 is at least 75.0%, is at least 75.1%, is at least 75.2%, is at least 75.3%, is at least 75.4%, is at least 75.5%, is at least 75.6%, is at least 75.7%, is at least 75.8%, is at least 75.9%, 76.0%, is at least 76.1%, is at least 76.2%, is at least 76.3%, is at least 76.4%, is at least 76.5%, is at least 76.6%, is at least 76.7%, is at least 76.8%, is at least 76.9%, 77.0%, is at least 77.1%, is at least 77.2%, is at least 77.3%, is at least 77.4%, is at least 77.5%, is at least 77.6%, is at least 77.7%, is at least 77.8%, is at least 77.9%, 78.0%, is at least 78.1%, is at least 78.2%, is at least 78.3%, is at least 78.4%, is at least 78.5%, is at least 78.6%, is at least 78.7%, is at least 78.8%, is at least 78.9%, 79.0%, is at least 79.1%, is at least 79.2%, is at least 79.3%, is at least 79.4%, is at least 79.5%, is at least 79.6%, is at least 79.7%, is at least 79.8%, is at least 79.9%, is at least 80%, is at least 81%, is at least 82%, is at least 83%, is at least 84%, and preferably is at least 85%, or at least 86%, or at least 87%, or at least 88%, or at least 89%, and more preferably is at least 90%, or at least 91%, or at least 92%, or at least 93%, or at least 94%, or at least 95, and even more preferably at least 96%, or at least 97%, or at least 98%, and most preferably at least 99%, at least 99.1%, or at least 99.2%, or at least 99.3%, or at least 99.4%, or at least 99.5%, or at least 99.6%, or at least 99.7%, or at least 99.8%, and in particular at least 99.9%, or 100%.

In a further preferred embodiment of the first aspect, the sucrose phosphorylase has one or more of the characteristics selected from the group consisting of (C) and (D), as defined by any of the aspects and/or embodiments described herein.

Preferably, the sucrose phosphorylase has one or more of the characteristics selected from the group consisting of (C) and (D), wherein the characteristic (C) is defined as a P/H-ratio of at least 200% up to 600%; and/or wherein the characteristic (D) is defined as an aG1P formation activity in 24 hours from 1 M sucrose and 1 M phosphate at 30° C. using 20 U heat-purified sucrose phosphorylase of at least 300 mM up to 1000 mM.

In another preferred embodiment of the first aspect, which is also a preferred embodiment of all previous embodiments, the invention relates to a sucrose phosphorylase comprising or consisting of an amino acid sequence, wherein the amino acid sequence is at least 79% homologous and/or identical to the amino acid sequence of SEQ ID NO: 1.

In this context, it is further preferred that the sucrose phosphorylase comprises the amino acid sequences selected from the group consisting of SEQ ID NO: 1, SEQ ID NO: 2, and SEQ ID NO: 3, preferably of SEQ ID NO: 1.

In a further preferred embodiment of the first aspect, the sucrose phosphorylase consists of the amino acid sequences selected from the group consisting of SEQ ID NO: 1, SEQ ID NO: 2, and SEQ ID NO: 3, preferably of SEQ ID NO: 1.

In another preferred embodiment of the first aspect, the sucrose phosphorylase comprises or consists of an amino acid sequence with at least 84% homology to SEQ ID NO: 1, characterized in that this amino acid sequence does not comprise or consist of the sequence of the wild type sucrose phosphorylase according to SEQ ID NO:1.

In another preferred embodiment of the first aspect, which is also a preferred embodiment of all previous embodiments, the sucrose phosphorylase comprises or consists of an amino acid sequence with at least 84% homology and/or at least 84% identity to SEQ ID NO: 1, wherein the amino acid sequence comprises one or more substitution at one or more amino acid positions compared to SEQ ID NO: 1, wherein the one or more amino acid positions is/are each and independently selected from the group consisting of the amino acid position E92, S124, A148, Q188, I231, L371, T461, preferably wherein the one or more amino acid positions is/are each and independently selected from the group consisting of the amino acids positions E92, S124, A148, Q188, I231, more preferably wherein the one or more amino acid positions is/are each and independently selected from the group consisting of the amino acids positions S124, A148, Q188 and most preferably wherein the one or more amino acid positions is/are each and independently selected from the group consisting of the amino acids positions A148, Q188.

Preferably, the amino acid sequence is, in addition, engineered compared to SEQ ID NO: 1 such that it comprises two or more substitutions, wherein the additional substitution amino acid positions are each and independently selected from the group consisting of the amino acid position E92, S124, A148, T157, Q188, I231, L371, and T461.

In another preferred embodiment of the first aspect, which is also a preferred embodiment of all previous embodiments described herein, the sucrose phosphorylase comprises or consists of an amino acid sequence, wherein the amino acid sequence is at least 84% homologous and/or at least 84% identical to SEQ ID NO: 1, and wherein the amino acid sequence comprises one or more substitutions at one or more amino acid positions of SEQ ID NO: 1, wherein the one or more amino acid positions is/are each and independently selected from the group consisting of the amino acid positions E92L, S124Q, S124K, S124T, A148R, A148K, Q188Y, I231V, L371A, and T461G.

In another preferred embodiment of the first aspect of the invention, which is also a preferred embodiment of all previous embodiments described herein, the amino acid sequence is engineered compared to SEQ ID NO: 1 such that it comprises two or more substitutions, wherein the pair of two amino acid positions is selected from the group consisting of E92 and S124, E92 and A148, E92 and T157, E92 and Q188, E92 and I231, E92 and L371, E92 and T461, S124 and A148, S124 and T157, S124 and Q188, S124 and I231, S124 and L371, S124 and T461, A148 and T157, A148 and Q188, A148 and I231, A148 and L371, A148 and T461, T157 and Q188, T157 and I231, T157 and L371, T157 and T461, Q188 and I231, Q188 and L371, Q188 and T461, I231 and L371, I231 and T461, L371 and T461, preferably wherein the pair of two amino acid positions is selected from the group consisting of E92 and S124, E92 and A148, E92 and Q188, E92 and I231, E92 and L371, E92 and T461, S124 and A148, S124 and Q188, S124 and I231, S124 and L371, S124 and T461, A148 and Q188, A148 and I231, A148 and L371, A148 and T461, Q188 and I231, Q188 and L371, Q188 and T461, I231 and L371, I231 and T461, L371 and T461, more preferably wherein the pair of two amino acid positions is selected from the group consisting of E92 and S124, E92 and A148, E92 and Q188, E92 and I231, S124 and A148, S124 and Q188, S124 and I231, A148 and Q188, A148 and I231, Q188 and I231, even more preferably wherein the pair of two amino acid positions is selected from the group consisting of S124 and A148, S124 and Q188, A148 and Q188, and most preferably is A148 and Q188.

In another preferred embodiment of the first aspect, which is also a preferred embodiment of all previous embodiments, the amino acid sequence is engineered compared to SEQ ID NO: 1 such that it comprises two or more substitutions, wherein the two or more amino acid positions is/are each and independently selected from the group consisting the amino acid position E92, S124, A148, T157, Q188, I231, L371, T461, preferably wherein the two or more amino acid positions is/are each and independently selected from the group consisting of the amino acids positions E92, S124, A148, Q188, I231, L371, T461, more preferably wherein the two or more amino acid positions is/are each and independently selected from the group consisting of the amino acids positions E92, S124, A148, Q188, I231, even more preferably wherein the two or more amino acid positions is/are each and independently selected from the group consisting of the amino acids positions S124, A148, Q188, and most preferably wherein the two or more amino acid positions is/are each and independently selected from the group consisting of the amino acids positions A148, Q188.

Preferably, the amino acid sequence is engineered compared to SEQ ID NO: 1 such that it comprises two or more substitutions, wherein the two or more amino acid positions is/are each and independently selected from the group consisting the amino acid position E92L, S124Q, S124K, S124T, A148K, A148R, T157D, Q188Y, I231V, L371A, T461G, preferably wherein the two or more amino acid positions is/are each and independently selected from the group consisting of the amino acids positions E92L, S124Q, S124K, S124T, A148K, A148R, Q188Y, I231V, L371A, T461G, more preferably wherein the two or more amino acid positions is/are each and independently selected from the group consisting of the amino acids positions E92L, S124Q, S124K, S124T, A148K, A148R, Q188Y, I231V, even more preferably wherein the two or more amino acid positions is/are each and independently selected from the group consisting of the amino acids positions S124Q, S124K, S124T, A148K, A148R, Q188Y, and most preferably wherein the two or more amino acid positions is/are each and independently selected from the group consisting of the amino acids positions A148K, A148R, Q188Y.

In another preferred embodiment, the amino acid sequence is, in addition, engineered compared to SEQ ID NO: 1 such that it comprises two or more substitutions, wherein the additional substitution amino acid positions are each and independently selected from the group consisting of the amino acid position E92, S124, A148, T157, Q188, I231, L371, T461.

Even more preferably, the amino acid sequence is, in addition, engineered compared to SEQ ID NO: 1 such that it comprises two or more substitutions, wherein the additional substitution amino acid positions are each and independently selected from the group consisting of the amino acid position E92L, S124Q, S124K, S124T, A148K, A148R, T157D, Q188Y, I231V, L371A, T461G.

In another preferred embodiment of the first aspect, which is also a preferred embodiment of all previous embodiments, the amino acid sequence is engineered compared to SEQ ID NO: 1 such that it comprises one or more substitution at one or more amino acid positions, wherein substitution at the one or more amino acid positions is/are each and independently selected from the group consisting of the substitutions:

(i) position E92 is substituted with A, R, N, D, C, Q, G, H, I, L, K, M, F, P, S, T, W, Y, or V; preferably is substituted with A, I, L, or V; and most preferably is substituted with L;
  (ii) position S124 is substituted with A, R, N, D, C, Q, E, G, H, I, L, K, M, F, P, T, W, Y, or V; preferably is substituted with R, H, K, N, M, C, S, T, or Q; even more preferably is substituted with Q, K, or T; still even more preferably is substituted with K, T; and most preferably substituted with K;
(iii) position A148 is substituted with R, N, D, C, Q, E, G, H, I, L, K, M, F, P, S, T, W, Y, or V; preferably is substituted with R, H, or K; more preferably is substituted with K, or R; and most preferably with K;
(iv) position T157 is substituted with A, R, N, D, C, Q, E, G, H, I, L, K, M, F, P, S, W, Y, or V; and preferably substituted with D;
(v) position Q188 is substituted with A, R, N, D, C, E, G, H, I, L, K, M, F, P, S, T, W, Y, or V; preferably is substituted with F, W, or Y; and most preferably is substituted with Y;
(vi) position I231 is substituted with A, R, N, D, C, Q, E, G, H, L, K, M, F, P, S, T, W, Y, or V; preferably is substituted with A, I, L, or V; and most preferably is substituted with V;
(vii) position L371 is substituted with A, R, N, D, C, Q, E, G, H, I, K, M, F, P, S, T, W, Y, or V; preferably is substituted with A, I, L, or V; and most preferably is substituted with A;
(viii) position T461 is substituted with A, R, N, D, C, Q, E, G, H, I, L, K, M, F, P, S, W, Y, or V; preferably is substituted with G, or P; and most preferably is substituted with G.

In another preferred embodiment of the first aspect, which is also a preferred embodiment of all previous embodiments, the sucrose phosphorylase comprises or consists of the amino acid sequences selected from the group consisting of SEQ ID NO: 6, SEQ ID NO: 7, SEQ ID NO: 8, SEQ ID NO: 9, SEQ ID NO: 10, SEQ ID NO: 11, SEQ ID NO: 13, ID NO: 14, SEQ ID NO: 15, SEQ ID NO: 16, SEQ ID NO: 17, and SEQ ID NO: 18, preferably of SEQ ID NO: 7, SEQ ID NO: 8, SEQ ID NO: 9, SEQ ID NO: 10, SEQ ID NO: 11, SEQ ID NO: 13, SEQ ID NO: 17, and SEQ ID NO: 18, and most preferably of SEQ ID NO: 10, SEQ ID NO: 11, SEQ ID NO: 13, SEQ ID NO: 17, and SEQ ID NO: 18.

In another preferred embodiment of the first aspect, which is also a preferred embodiment of all previous embodiments, the sucrose phosphorylase comprises or consists of the amino acid sequences selected from the group consisting of SEQ ID NO: 11, and SEQ ID NO: 17, wherein the sucrose phosphorylase preferably comprises or consists of the amino acid sequence of SEQ ID NO: 17.

In another preferred embodiment of the first aspect, which is also a preferred embodiment of the previous embodiments, the homology and/or identity of the amino acid sequence to SEQ ID NO: 1 is at least 79.0%, is at least 79.1%, is at least 79.2%, is at least 79.3%, is at least 79.4%, is at least 79.5%, is at least 79.6%, is at least 79.7%, is at least 79.8%, is at least 79.9%, is at least 80%, is at least 81%, is at least 82%, is at least 83%, is at least 84%, and preferably is at least 85%, or at least 86%, or at least 87%, or at least 88%, or at least 89%, and more preferably is at least 90%, or at least 91%, or at least 92%, or at least 93%, or at least 94%, or at least 95, and even more preferably at least 96%, or at least 97%, or at least 98%, and most preferably at least 99%, at least 99.1%, or at least 99.2%, or at least 99.3%, or at least 99.4%, or at least 99.5%, or at least 99.6%, or at least 99.7%, or at least 99.8%, and in particular at least 99.9%, or 100%.

In the context of the present invention, and with respect to all aspects and embodiments described herein, the sucrose phosphorylase of the invention is capable of catalyzing the phosphorolytic cleavage of substrate glucoside into aG1P and a co-product.

Preferably, the sucrose phosphorylase of the present invention is capable of catalyzing the phosphorolytic cleavage of a substrate glucoside, wherein the substrate glucoside is sucrose.

More preferably, the sucrose phosphorylase is capable of catalyzing the phosphorolytic cleavage of a substrate glucoside to aG1P and a co-product, wherein the co-product is fructose.

Even more preferably, the catalytic reaction is characterized in that the reaction of aG1P and the co-product is reversible.

In yet another preferred embodiment of the first aspect, which is also a preferred embodiment of all previous embodiments, the sucrose phosphorylase of the invention is capable of catalyzing the phosphorolytic cleavage of a substrate glucoside to aG1P and a co-product, wherein the aG1P is enzymatically converted by at least one further enzyme into a final product.

Preferably, the final product is selected from the group consisting of trehalose, cellobiose, laminaribiose, laminaritriose, laminaritetraose, laminaribiose-oligosaccharides, lacto-N-biose, galacto-N-biose, kojibiose.

Even more preferred is that the at least one further enzyme for conversion into a final product is selected from the group consisting of trehalose phosphorylase, cellobiose phosphorylase, laminaribiose phosphorylase, lacto-N-biose phosphorylase, UDP-glucose-4-epimerase, UTP-glucose-1-phosphate uridylyltransferase, phosphoglucomutase, glucose 6-phosphate 1-epimerase, beta-phosphoglucomutase, kojibiose phosphorylase, glucose isomerase.

In yet another preferred embodiment of the first aspect, which is also a preferred embodiment of all previous embodiments, the sucrose phosphorylase of the invention is capable of catalyzing a transglycosylation reaction of a donor glucoside and an acceptor substrate.

Preferably, the sucrose phosphorylase is capable of catalyzing a transglycosylation reaction of a donor glucoside and an acceptor substrate, and wherein the acceptor substrate is selected from the group consisting of a carbohydrate, an alditol, glycerol, 1,2-propanediol and derivatives, carboxy acids and phenolic compounds, preferably glucose, arabinose, sorbose, ketoxylose, ketoarabinose, rhamnulose, fucose, fructose, galactose, xylose, xylitol, arabitol, sorbitol, glycerol, 1,2-propanediol, 2,3-methoxy-1,2-propanediol, 3,3-ethoxy-1,2-propanediol, 4,3-allyloxy-1,2-propanediol, 5,3-tert-butoxy-1,2-propanediol, 6,3-(o-methoxyphenoxy)-1,2-propanediol, caffeic acid, acetate, formate, sodium benzoate, hydrochinone, catechin, epigallocatechin gallate, 4-hydroxy-2,5-dimethyl-3(2H)-furanone, 2-ethyl-4-hydroxy-5-methyl-3(2H)-furanone, and kojic acid.

In another preferred embodiment of the first aspect, which is also a preferred embodiment of all previous embodiments, the sucrose phosphorylase of the invention has one or more of the characteristics selected from the group (A), (B) (C), and (D):

(A) a Tm50 value of at least 66.5° C. up to 90° C., at least 67.0° C. up to 90° C., at least 67.5° C. up to 90° C., at least 68.0° C. up to 90° C., at least 68.5° C. up to 90° C., at least 69.0° C. up to 90° C., at least 69.5° C. up to 90° C., at least 70.0° C. up to 90° C., at least 70.5° C. up to 90° C., at least 71.0° C. up to 90° C., at least 71.5° C. up to 90° C., at least 72.0° C. up to 90° C., preferably of at least 68.0° C. up to 90° C., at least 68.5° C. up to 90° C., at least 69.0° C. up to 90° C., at least 69.5° C. up to 90° C., at least 70.0° C. up to 90° C., at least 70.5° C. up to 90° C., at least 71.0° C. up to 90° C., at least 71.5° C. up to 90° C., at least 72.0°

C. up to 90° C., more preferably of at least 70.0° C. up to 90° C., at least 70.5° C. up to 90° C., at least 71.0° C. up to 90° C., at least 71.5° C. up to 90° C., at least 72.0° C. up to 90° C., and most preferably of at least 68.0° C. up to 85° C., at least 68.5° C. up to 85° C., at least 69.0° C. up to 85° C., at least 69.5° C. up to 85° C., at least 70.0° C. up to 85° C., at least 70.5° C. up to 85° C., at least 71.0° C. up to 85° C., at least 71.5° C. up to 85° C., at least 72.0° C. up to 85° C., of at least 68.0° C. up to 80° C., at least 68.5° C. up to 80° C., at least 69.0° C. up to 80° C., at least 69.5° C. up to 80° C., at least 70.0° C. up to 80° C., at least 70.5° C. up to 80° C., at least 71.0° C. up to 80° C., at least 71.5° C. up to 80° C., at least 72.0° C. up to 80° C., of at least 68.0° C. up to 75° C., at least 68.5° C. up to 75° C., at least 69.0° C. up to 75° C., at least 69.5° C. up to 75° C., at least 70.0° C. up to 75° C., at least 70.5° C. up to 75° C., at least 71.0° C. up to 75° C., at least 71.5° C. up to 75° C., at least 72.0° C. up to 75° C., and utmost preferably of at least 68.0° C. up to 72° C., at least 68.5° C. up to 72° C., or at least 68.0° C. up to 70° C.;

(B) residual activity after 15 min incubation at 70° C. of at least 25% up to 100%, at least 26% up to 100%, at least 27% up to 100%, at least 28% up to 100%, at least 29% up to 100%, at least 30% up to 100%, at least 31% up to 100%, at least 32% up to 100%, at least 33% up to 100%, at least 34% up to 100%, at least 35% up to 100%, at least 36% up to 100%, at least 37% up to 100%, at least 38% up to 100%, at least 39% up to 100%, at least 40% up to 100%, at least 41% up to 100%, at least 42% up to 100%, at least 43% up to 100%, at least 44% up to 100%, at least 45% up to 100%, at least 46% up to 100%, at least 47% up to 100%, at least 48% up to 100%, at least 49% up to 100%, at least 50% up to 100%, at least 51% up to 100%, at least 52% up to 100%, at least 53% up to 100%, at least 54% up to 100%, at least 55% up to 100%, at least 56% up to 100%, at least 57% up to 100%, at least 58% up to 100%, at least 59% up to 100%, 60% up to 100%, at least 61% up to 100%, at least 62% up to 100%, at least 63% up to 100%, at least 64% up to 100%, preferably at least 40% up to 100%, at least 41% up to 100%, at least 42% up to 100%, at least 43% up to 100%, at least 44% up to 100%, at least 45% up to 100%, at least 46% up to 100%, at least 47% up to 100%, at least 48% up to 100%, at least 49% up to 100%, at least 50% up to 100%, at least 51% up to 100%, at least 52% up to 100%, at least 53% up to 100%, at least 54% up to 100%, at least 55% up to 100%, at least 56% up to 100%, at least 57% up to 100%, at least 58% up to 100%, at least 59% up to 100%, 60% up to 100%, at least 61% up to 100%, at least 62% up to 100%, at least 63% up to 100%, at least 64% up to 100%, more preferably of at least 50% up to 100%, at least 51% up to 100%, at least 52% up to 100%, at least 53% up to 100%, at least 54% up to 100%, at least 55% up to 100%, at least 56% up to 100%, at least 57% up to 100%, at least 58% up to 100%, at least 59% up to 100%, 60% up to 100%, at least 61% up to 100%, at least 62% up to 100%, at least 63% up to 100%, at least 64% up to 100%, and most preferably of at least of at least 50% up to 64%, at least 51% up to 64%, at least 52% up to 64%, at least 53% up to 64%, at least 54% up to 64%, at least 55% up to 64%, at least 56% up to 64%, at least 57% up to 64%, at least 58% up to 64%, at least 59% up to 64%, 60% up to 64%, at least 61% up to 64%, at least 62% up to 64%, at least 63% up to 64%, and utmost preferably of 64%;

(C) P/H-ratio of at least 200% up to 600%, at least 250% up to 600%, at least 275% up to 600%, at least 296% up to 600%, at least 299% up to 600%, at least 300% up to 600%, at least 331% up to 600%, at least 350% up to 600%, at least 354% up to 600%, at least 360% up to 600%, at least 370% up to 600%, at least 373% up to 600%, preferably of at least 200% up to 500%, at least 250% up to 500%, at least 275% up to 500%, at least 296% up to 500%, at least 299% up to 500%, at least 300% up to 500%, at least 331% up to 500%, at least 350% up to 500%, at least 354% up to 500%, at least 360% up to 500%, at least 370% up to 500%, at least 373% up to 500%, more preferably of at least 200% up to 450%, at least 250% up to 450%, at least 275% up to 450%, at least 296% up to 450%, at least 299% up to 450%, at least 300% up to 450%, at least 331% up to 450%, at least 350% up to 450%, at least 354% up to 450%, at least 360% up to 450%, at least 370% up to 450%, at least 373% up to 450%, even more preferably of at least 200% up to 400%, at least 250% up to 400%, at least 275% up to 400%, at least 296% up to 400%, at least 299% up to 400%, at least 300% up to 400%, at least 331% up to 400%, at least 350% up to 400%, at least 354% up to 400%, at least 360% up to 400%, at least 370% up to 400%, at least 373% up to 400%, and most preferably of at least 275% up to 373%, at least 296% up to 373%, at least 299% up to 373%, at least 300% up to 373%, at least 331% up to 373%;

(D) aG1P formation activity in 24 hours from 1M sucrose and 1M phosphate at 30° C. using 20 U heat-purified sucrose phosphorylase of at least 300 mM up to 1000 mM, at least 350 mM up to 1000 mM, at least 354 mM up to 1000 mM, at least 367 mM up to 1000 mM, at least 400 mM up to 1000 mM, at least 422 mM up to 1000 mM, at least 450 mM up to 1000 mM, at least 484 mM up to 1000 mM, at least 500 mM up to 1000 mM, at least 501 mM up to 1000 mM, preferably of at least 300 mM up to 750 mM, at least 350 mM up to 750 mM, at least 354 mM up to 750 mM, at least 367 mM up to 750 mM, at least 400 mM up to 750 mM, at least 422 mM up to 750 mM, at least 450 mM up to 750 mM, at least 484 mM up to 750 mM, at least 500 mM up to 750 mM, at least 501 mM up to 750 mM, more preferably at least 300 mM up to 600 mM, at least 350 mM up to 600 mM, at least 354 mM up to 600 mM, at least 367 mM up to 600 mM, at least 400 mM up to 600 mM, at least 422 mM up to 600 mM, at least 450 mM up to 600 mM, at least 484 mM up to 600 mM, at least 500 mM up to 600 mM, at least 501 mM up to 600 mM, even more preferably at least 300 mM up to 550 mM, at least 350 mM up to 550 mM, at least 354 mM up to 550 mM, at least 367 mM up to 550 mM, at least 400 mM up to 550 mM, at least 422 mM up to 550 mM, at least 450 mM up to 550 mM, at least 484 mM up to 550 mM, at least 500 mM up to 550 mM, at least 501 mM up to 550 mM, and most preferably of at least 300 mM up to 501 mM, at least 350 mM up to 501 mM, at least 354 mM up to 501 mM, at least 367 mM up to 501 mM, at least 400 mM up to 501 mM, at least 422 mM up to 501 mM, at least 450 mM up to 501 mM, at least 484 mM up to 501 mM.

Preferably, the sucrose phosphorylase has two or more characteristics selected from the group consisting of the characteristics (A) and (B), (A) and (C), (A) and (D), (B) and (C), (B) and (D), (C) and (D), (A) and (B) and (C), (A) and (B) and (D), (A) and (C) and (D), and (A) and (B) and (C) and (D), and preferably (A) and (B) and (C).

In another preferred embodiment, which is also a preferred embodiment of all previous embodiments, the sucrose phosphorylase has at least the characteristic (C):

(C) a P/H-ratio of at least 200% up to 600%, at least 250% up to 600%, at least 275% up to 600%, at least 296% up to 600%, at least 299% up to 600%, at least 300% up to 600%, at least 331% up to 600%, at least 350% up to 600%, at least 354% up to 600%, at least 360% up to 600%, at least 370% up to 600%, at least 373% up to 600%, preferably of at least 200% up to 500%, at least 250% up to 500%, at least 275% up to 500%, at least 296% up to 500%, at least 299% up to 500%, at least 300% up to 500%, at least 331% up to 500%, at least 350% up to 500%, at least 354% up to 500%, at least 360% up to 500%, at least 370% up to 500%, at least 373% up to 500%, more preferably of at least 200% up to 450%, at least 250% up to 450%, at least 275% up to 450%, at least 296% up to 450%, at least 299% up to 450%, at least 300% up to 450%, at least 331% up to 450%, at least 350% up to 450%, at least 354% up to 450%, at least 360% up to 450%, at least 370% up to 450%, at least 373% up to 450%, even more preferably of at least 200% up to 400%, at least 250% up to 400%, at least 275% up to 400%, at least 296% up to 400%, at least 299% up to 400%, at least 300% up to 400%, at least 331% up to 400%, at least 350% up to 400%, at least 354% up to 400%, at least 360% up to 400%, at least 370% up to 400%, at least 373% up to 400%, and most preferably of at least 275% up to 373%, at least 296% up to 373%, at least 299% up to 373%, at least 300% up to 373%, at least 331% up to 373%.

In the context of the present invention, the sucrose phosphorylase is preferably the sucrose phosphorylase as defined by any one of the embodiments described above.

In another preferred embodiment of the first aspect, and to any one of the embodiments described herein, the sucrose phosphorylase is the sucrose phosphorylase of SEQ ID NO: 1, 2, 3, 4, 6, 7, 8, 9, 10, 11, 12, 13, 14, 15, 16, 17, and 18, preferably of SEQ ID NO: 1, 6, 7, 8, 9, 10, 11, 12, 13, 14, 15, 16, 17, and 18, more preferably of SEQ ID NO: 1, 7, 8, 9, 10, 11, 13, 17, and 18, even more preferably of SEQ ID NO: 1, 10, 11, 13, 17, and most preferably of SEQ ID NO: 1, and 17.

In another preferred embodiment of the invention, which is also a preferred embodiment of all previous embodiments, the sucrose phosphorylase has at least the characteristic (D):

(D) aG1P formation activity in 24 hours from 1M sucrose and 1M phosphate at 30° C. using 20 U heat-purified sucrose phosphorylase of at least 300 mM up to 1000 mM, at least 350 mM up to 1000 mM, at least 354 mM up to 1000 mM, at least 367 mM up to 1000 mM, at least 400 mM up to 1000 mM, at least 422 mM up to 1000 mM, at least 450 mM up to 1000 mM, at least 484 mM up to 1000 mM, at least 500 mM up to 1000 mM, at least 501 mM up to 1000 mM, preferably of at least 300 mM up to 750 mM, at least 350 mM up to 750 mM, at least 354 mM up to 750 mM, at least 367 mM up to 750 mM, at least 400 mM up to 750 mM, at least 422 mM up to 750 mM, at least 450 mM up to 750 mM, at least 484 mM up to 750 mM, at least 500 mM up to 750 mM, at least 501 mM up to 750 mM, more preferably at least 300 mM up to 600 mM, at least 350 mM up to 600 mM, at least 354 mM up to 600 mM, at least 367 mM up to 600 mM, at least 400 mM up to 600 mM, at least 422 mM up to 600 mM, at least 450 mM up to 600 mM, at least 484 mM up to 600 mM, at least 500 mM up to 600 mM, at least 501 mM up to 600 mM, even more preferably at least 300 mM up to 550 mM, at least 350 mM up to 550 mM, at least 354 mM up to 550 mM, at least 367 mM up to 550 mM, at least 400 mM up to 550 mM, at least 422 mM up to 550 mM, at least 450 mM up to 550 mM, at least 484 mM up to 550 mM, at least 500 mM up to 550 mM, at least 501 mM up to 550 mM, and most preferably of at least 300 mM up to 501 mM, at least 350 mM up to 501 mM, at least 354 mM up to 501 mM, at least 367 mM up to 501 mM, at least 400 mM up to 501 mM, at least 422 mM up to 501 mM, at least 450 mM up to 501 mM, at least 484 mM up to 501 mM in aG1P formation assay.

In the context of the present invention, the sucrose phosphorylase is preferably the sucrose phosphorylase as defined by any one of the embodiments described above.

In yet another preferred embodiment of the first aspect, and to any one of the embodiments described herein, the sucrose phosphorylase is the sucrose phosphorylase of SEQ ID NO: 1, 2, 3, 4, 6, 7, 8, 9, 10, 11, 12, 13, 14, 15, 16, 17, and 18, preferably of SEQ ID NO: 1, 6, 7, 8, 9, 10, 11, 12, 13, 14, 15, 16, 17, and 18, more preferably of SEQ ID NO: 1, 7, 8, 9, 10, 11, 13, 17, and 18, even more preferably of SEQ ID NO: 1, 10, 11, 13, 17, and most preferably of SEQ ID NO: 1, and 17.

In another preferred embodiment, which is also a preferred embodiment of all previous embodiments, the sucrose phosphorylase of the invention has at least the characteristic (A) and/or (B):

(A) a thermal stability of a Tm50 value of at least 66.5° C. up to 90° C., at least 67.0° C. up to 90° C., at least 67.5° C. up to 90° C., at least 68.0° C. up to 90° C., at least 68.5° C. up to 90° C., at least 69.0° C. up to 90° C., at least 69.5° C. up to 90° C., at least 70.0° C. up to 90° C., at least 70.5° C. up to 90° C., at least 71.0° C. up to 90° C., at least 71.5° C. up to 90° C., at least 72.0° C. up to 90° C., preferably of at least 68.0° C. up to 90° C., at least 68.5° C. up to 90° C., at least 69.0° C. up to 90° C., at least 69.5° C. up to 90° C., at least 70.0° C. up to 90° C., at least 70.5° C. up to 90° C., at least 71.0° C. up to 90° C., at least 71.5° C. up to 90° C., at least 72.0° C. up to 90° C., more preferably of at least 70.0° C. up to 90° C., at least 70.5° C. up to 90° C., at least 71.0° C. up to 90° C., at least 71.5° C. up to 90° C., at least 72.0° C. up to 90° C., and most preferably of at least 68.0° C. up to 85° C., at least 68.5° C. up to 85° C., at least 69.0° C. up to 85° C., at least 69.5° C. up to 85° C., at least 70.0° C. up to 85° C., at least 70.5° C. up to 85° C., at least 71.0° C. up to 85° C., at least 71.5° C. up to 85° C., at least 72.0° C. up to 85° C., of at least 68.0° C. up to 80° C., at least 68.5° C. up to 80° C., at least 69.0° C. up to 80° C., at least 69.5° C. up to 80° C., at least 70.0° C. up to 80° C., at least 70.5° C. up to 80° C., at least 71.0° C. up to 80° C., at least 71.5° C. up to 80° C., at least 72.0° C. up to 80° C., of at least 68.0° C. up to 75° C., at least 68.5° C. up to 75° C., at least 69.0° C. up to 75° C., at least 69.5° C. up to 75° C., at least 70.0° C. up to 75° C., at least 70.5° C. up to 75° C., at least 71.0° C. up to 75° C., at least 71.5° C. up to 75° C., at least 72.0° C. up to 75° C., and utmost preferably of at least 68.0° C. up to 72° C., at least 68.5° C. up to 72° C., or at least 68.0° C. up to 70° C.;

(B) a thermal stability of residual activity after 15 min incubation at 70° C. of at least 25% up to 100%, at least 26% up to 100%, at least 27% up to 100%, at least 28% up to 100%, at least 29% up to 100%, at least 30% up to 100%, at least 31% up to 100%, at least 32% up to 100%, at least 33% up to 100%, at least 34% up to 100%, at least 35% up to 100%, at least 36% up to 100%, at least 37% up to 100%, at least 38% up to 100%, at least 39% up to 100%, at least 40% up to 100%, at least 41% up to 100%, at least 42% up to 100%, at least 43% up to 100%, at least 44% up to 100%, at least 45% up to 100%, at least 46% up to 100%, at least 47% up to 100%, at least 48% up to 100%, at least 49% up to 100%, at least 50% up to 100%, at least 51% up to 100%, at least 52% up to 100%, at least 53% up to 100%, at least 54% up to 100%, at least 55% up to 100%, at least 56% up to 100%, at least 57% up to 100%, at least 58% up to 100%, at least 59% up to 100%, 60% up to 100%, at least 61% up to 100%, at least 62% up to 100%, at least 63% up to 100%, at least 64% up to 100%, preferably at least 40% up to 100%, at least 41% up to 100%, at least 42% up to 100%, at least 43% up to 100%, at least 44% up to 100%, at least 45% up to 100%, at least 46% up to 100%, at least 47% up to 100%, at least 48% up to 100%, at least 49% up to 100%, at least 50% up to 100%, at least 51% up to 100%, at least 52% up to 100%, at least 53% up to 100%, at least 54% up to 100%, at least 55% up to 100%, at least 56% up to 100%, at least 57% up to 100%, at least 58% up to 100%, at least 59% up to 100%, 60% up to 100%, at least 61% up to 100%, at least 62% up to 100%, at least 63% up to 100%, at least 64% up to 100%, more preferably of at least 50% up to 100%, at least 51% up to 100%, at least 52% up to 100%, at least 53% up to 100%, at least 54% up to 100%, at least 55% up to 100%, at least 56% up to 100%, at least 57% up to 100%, at least 58% up to 100%, at least 59% up to 100%, 60% up to 100%, at least 61% up to 100%, at least 62% up to 100%, at least 63% up to 100%, at least 64% up to 100%, and most preferably of at least of at least 50% up to 64%, at least 51% up to 64%, at least 52% up to 64%, at least 53% up to 64%, at least 54% up to 64%, at least 55% up to 64%, at least 56% up to 64%, at least 57% up to 64%, at least 58% up to 64%, at least 59% up to 64%, 60% up to 64%, at least 61% up to 64%, at least 62% up to 64%, at least 63% up to 64%, and utmost preferably of 64%.

In the context of the present invention, the sucrose phosphorylase is preferably the sucrose phosphorylase as defined by any one of the embodiments described above.

In another preferred embodiment, and to any one of the embodiments described herein, the sucrose phosphorylase is the sucrose phosphorylase of SEQ ID NO: 6, 7, 8, 9, 10, 11, 13, 14, 15, 16, 17, and 18, preferably of SEQ ID NO: 6, 7, 8, 9, 10, 11, 13, 14, 17, and 18, more preferably of SEQ ID NO: 7, 8, 9, 10, 11, 13, 17, and 18, even more preferably of SEQ ID NO: 10, 11, 13, 17, and most preferably of SEQ ID NO: 11, and 17, and utmost preferably of SEQ ID NO: 17.

In a second aspect, the invention relates to a sucrose phosphorylase comprising or consisting of an amino acid sequence, wherein the amino acid sequence of the sucrose phosphorylase is at least 75% identical to and/or at least 75% homologous to the amino acid sequence of SEQ ID NO: 1, wherein the sucrose phosphorylase has one or more of the characteristics selected from the group (A), (B) (C), and (D):

(A) a Tm50 value of at least 66.5° C. up to 90° C., at least 67.0° C. up to 90° C., at least 67.5° C. up to 90° C., at least 68.0° C. up to 90° C., at least 68.5° C. up to 90° C., at least 69.0° C. up to 90° C., at least 69.5° C. up to 90° C., at least 70.0° C. up to 90° C., at least 70.5° C. up to 90° C., at least 71.0° C. up to 90° C., at least 71.5° C. up to 90° C., at least 72.0° C. up to 90° C., preferably of at least 68.0° C. up to 90° C., at least 68.5° C. up to 90° C., at least 69.0° C. up to 90° C., at least 69.5° C. up to 90° C., at least 70.0° C. up to 90° C., at least 70.5° C. up to 90° C., at least 71.0° C. up to 90° C., at least 71.5° C. up to 90° C., at least 72.0° C. up to 90° C., more preferably of at least 70.0° C. up to 90° C., at least 70.5° C. up to 90° C., at least 71.0° C. up to 90° C., at least 71.5° C. up to 90° C., at least 72.0° C. up to 90° C., and most preferably of at least 68.0° C. up to 85° C., at least 68.5° C. up to 85° C., at least 69.0° C. up to 85° C., at least 69.5° C. up to 85° C., at least 70.0° C. up to 85° C., at least 70.5° C. up to 85° C., at least 71.0° C. up to 85° C., at least 71.5° C. up to 85° C., at least 72.0° C. up to 85° C., of at least 68.0° C. up to 80° C., at least 68.5° C. up to 80° C., at least 69.0° C. up to 80° C., at least 69.5° C. up to 80° C., at least 70.0° C. up to 80° C., at least 70.5° C. up to 80° C., at least 71.0° C. up to 80° C., at least 71.5° C. up to 80° C., at least 72.0° C. up to 80° C., of at least 68.0° C. up to 75° C., at least 68.5° C. up to 75° C., at least 69.0° C. up to 75° C., at least 69.5° C. up to 75° C., at least 70.0° C. up to 75° C., at least 70.5° C. up to 75° C., at least 71.0° C. up to 75° C., at least 71.5° C. up to 75° C., at least 72.0° C. up to 75° C., and utmost preferably of at least 68.0° C. up to 72° C., at least 68.5° C. up to 72° C., or at least 68.0° C. up to 70° C.;

(B) residual activity after 15 min incubation at 70° C. of at least 25% up to 100%, at least 26% up to 100%, at least 27% up to 100%, at least 28% up to 100%, at least 29% up to 100%, at least 30% up to 100%, at least 31% up to 100%, at least 32% up to 100%, at least 33% up to 100%, at least 34% up to 100%, at least 35% up to 100%, at least 36% up to 100%, at least 37% up to 100%, at least 38% up to 100%, at least 39% up to 100%, at least 40% up to 100%, at least 41% up to 100%, at least 42% up to 100%, at least 43% up to 100%, at least 44% up to 100%, at least 45% up to 100%, at least 46% up to 100%, at least 47% up to 100%, at least 48% up to 100%, at least 49% up to 100%, at least 50% up to 100%, at least 51% up to 100%, at least 52% up to 100%, at least 53% up to 100%, at least 54% up to 100%, at least 55% up to 100%, at least 56% up to 100%, at least 57% up to 100%, at least 58% up to 100%, at least 59% up to 100%, 60% up to 100%, at least 61% up to 100%, at least 62% up to 100%, at least 63% up to 100%, at least 64% up to 100%, preferably at least 40% up to 100%, at least 41% up to 100%, at least 42% up to 100%, at least 43% up to 100%, at least 44% up to 100%, at least 45% up to 100%, at least 46% up to 100%, at least 47% up to 100%, at least 48% up to 100%, at least 49% up to 100%, at least 50% up to 100%, at least 51% up to 100%, at least 52% up to 100%, at least 53% up to 100%, at least 54% up to 100%, at least 55% up to 100%, at least 56% up to 100%, at least 57% up to 100%, at least 58% up to 100%, at least 59% up to 100%, 60% up to 100%, at least 61% up to 100%, at least 62% up to 100%, at least 63% up to 100%, at least 64% up to 100%, more preferably of at least 50% up to 100%, at least 51% up to 100%, at least 52% up to 100%, at least 53% up to 100%, at least 54% up to 100%, at least 55% up to 100%, at least 56% up to 100%, at least 57% up to 100%, at least 58% up to 100%, at least 59% up to 100%, 60% up to 100%, at least 61% up to 100%, at least 62% up to 100%, at least 63% up to 100%, at least 64% up to 100%, and most preferably of at least of at least 50% up to 64%, at least 51% up to 64%, at least 52% up to 64%, at least 53% up to 64%, at least 54% up to 64%, at least 55% up to 64%, at least 56% up to 64%, at least 57% up to 64%, at least 58% up to 64%, at least 59% up to 64%, 60% up to 64%, at least 61% up to 64%, at least 62% up to 64%, at least 63% up to 64%, and utmost preferably of 64%;

(C) P/H-ratio of at least 200% up to 600%, at least 250% up to 600%, at least 275% up to 600%, at least 296% up to 600%, at least 299% up to 600%, at least 300% up to 600%, at least 331% up to 600%, at least 350% up to 600%, at least 354% up to 600%, at least 360% up to 600%, at least 370% up to 600%, at least 373% up to 600%, preferably of at least 200% up to 500%, at least 250% up to 500%, at least 275% up to 500%, at least 296% up to 500%, at least 299% up to 500%, at least 300% up to 500%, at least 331% up to 500%, at least 350% up to 500%, at least 354% up to 500%, at least 360% up to 500%, at least 370% up to 500%, at least 373% up to 500%, more preferably of at least 200% up to 450%, at least 250% up to 450%, at least 275% up to 450%, at least 296% up to 450%, at least 299% up to 450%, at least 300% up to 450%, at least 331% up to 450%, at least 350% up to 450%, at least 354% up to 450%, at least 360% up to 450%, at least 370% up to 450%, at least 373% up to 450%, even more preferably of at least 200% up to 400%, at least 250% up to 400%, at least 275% up to 400%, at least 296% up to 400%, at least 299% up to 400%, at least 300% up to 400%, at least 331% up to 400%, at least 350% up to 400%, at least 354% up to 400%, at least 360% up to 400%, at least 370% up to 400%, at least 373% up to 400%, and most preferably of at least 275% up to 373%, at least 296% up to 373%, at least 299% up to 373%, at least 300% up to 373%, at least 331% up to 373%;

(D) aG1P formation activity in 24 hours from 1M sucrose and 1M phosphate at 30° C. using 20 U heat-purified sucrose phosphorylase of at least 300 mM up to 1000 mM, at least 350 mM up to 1000 mM, at least 354 mM up to 1000 mM, at least 367 mM up to 1000 mM, at least 400 mM up to 1000 mM, at least 422 mM up to 1000 mM, at least 450 mM up to 1000 mM, at least 484 mM up to 1000 mM, at least 500 mM up to 1000 mM, at least 501 mM up to 1000 mM, preferably of at least 300 mM up to 750 mM, at least 350 mM up to 750 mM, at least 354 mM up to 750 mM, at least 367 mM up to 750 mM, at least 400 mM up to 750 mM, at least 422 mM up to 750 mM, at least 450 mM up to 750 mM, at least 484 mM up to 750 mM, at least 500 mM up to 750 mM, at least 501 mM up to 750 mM, more preferably at least 300 mM up to 600 mM, at least 350 mM up to 600 mM, at least 354 mM up to 600 mM, at least 367 mM up to 600 mM, at least 400 mM up to 600 mM, at least 422 mM up to 600 mM, at least 450 mM up to 600 mM, at least 484 mM up to 600 mM, at least 500 mM up to 600 mM, at least 501 mM up to 600 mM, even more preferably at least 300 mM up to 550 mM, at least 350 mM up to 550 mM, at least 354 mM up to 550 mM, at least 367 mM up to 550 mM, at least 400 mM up to 550 mM, at least 422 mM up to 550 mM, at least 450 mM up to 550 mM, at least 484 mM up to 550 mM, at least 500 mM up to 550 mM, at least 501 mM up to 550 mM, and most preferably of at least 300 mM up to 501 mM, at least 350 mM up to 501 mM, at least 354 mM up to 501 mM, at least 367 mM up to 501 mM, at least 400 mM up to 501 mM, at least 422 mM up to 501 mM, at least 450 mM up to 501 mM, at least 484 mM up to 501 mM.

Preferably, in this context, the sucrose phosphorylase has two or more characteristics selected from the group consisting of the characteristics (A) and (B), (A) and (C), (A) and (D), (B) and (C), (B) and (D), (C) and (D), (A) and (B) and (C), (A) and (B) and (D), (A) and (C) and (D), and (A) and (B) and (C) and (D), and preferably (A) and (B) and (C).

More preferably, the sucrose phosphorylase has at least the characteristics (C):

(C) a P/H-ratio of at least 200% up to 600%, at least 250% up to 600%, at least 275% up to 600%, at least 296% up to 600%, at least 299% up to 600%, at least 300% up to 600%, at least 331% up to 600%, at least 350% up to 600%, at least 354% up to 600%, at least 360% up to 600%, at least 370% up to 600%, at least 373% up to 600%, preferably of at least 200% up to 500%, at least 250% up to 500%, at least 275% up to 500%, at least 296% up to 500%, at least 299% up to 500%, at least 300% up to 500%, at least 331% up to 500%, at least 350% up to 500%, at least 354% up to 500%, at least 360% up to 500%, at least 370% up to 500%, at least 373% up to 500%, more preferably of at least 200% up to 450%, at least 250% up to 450%, at least 275% up to 450%, at least 296% up to 450%, at least 299% up to 450%, at least 300% up to 450%, at least 331% up to 450%, at least 350% up to 450%, at least 354% up to 450%, at least 360% up to 450%, at least 370% up to 450%, at least 373% up to 450%, even more preferably of at least 200% up to 400%, at least 250% up to 400%, at least 275% up to 400%, at least 296% up to 400%, at least 299% up to 400%, at least 300% up to 400%, at least 331% up to 400%, at least 350% up to 400%, at least 354% up to 400%, at least 360% up to 400%, at least 370% up to 400%, at least 373% up to 400%, and most preferably of at least 275% up to 373%, at least 296% up to 373%, at least 299% up to 373%, at least 300% up to 373%, at least 331% up to 373%.

In a preferred embodiment of the second aspect, the sucrose phosphorylase comprises or consists of an amino acid sequence, wherein amino acid sequence has an homology and/or an identity to the amino acid sequence to SEQ ID NO: 1 which is at least 75.0%, at least 76.0%, at least 77.0%, at least 78.0%, at least 79.0%, is at least 79.1%, is at least 79.2%, is at least 79.3%, is at least 79.4%, is at least 79.5%, is at least 79.6%, is at least 79.7%, is at least 79.8%, is at least 79.9%, is at least 80%, is at least 81%, is at least 82%, is at least 83%, is at least 84%, and preferably is at least 85%, or at least 86%, or at least 87%, or at least 88%, or at least 89%, and more preferably is at least 90%, or at least 91%, or at least 92%, or at least 93%, or at least 94%, or at least 95, and even more preferably at least 96%, or at least 97%, or at least 98%, and most preferably at least 99%, at least 99.1%, or at least 99.2%, or at least 99.3%, or at least 99.4%, or at least 99.5%, or at least 99.6%, or at least 99.7%, or at least 99.8%, and in particular at least 99.9%, or 100%.

In a preferred embodiment of the second aspect, which is also a preferred embodiment of all previous embodiments described herein, the sucrose phosphorylase is the sucrose phosphorylase as defined by any one of the embodiments described above.

Even more preferably, the sucrose phosphorylase is the sucrose phosphorylase of SEQ ID NO: 1, 2, 3, 4, 6, 7, 8, 9, 10, 11, 12, 13, 14, 15, 16, 17, and 18, preferably of SEQ ID NO: 1, 6, 7, 8, 9, 10, 11, 12, 13, 14, 15, 16, 17, and 18, more preferably of SEQ ID NO: 1, 7, 8, 9, 10, 11, 13, 17, and 18, even more preferably of SEQ ID NO: 1, 10, 11, 13, 17, and most preferably of SEQ ID NO: 1, and 17.

In another preferred embodiment of the second aspect, which is also a preferred embodiment to any one of the previous embodiments thereto, the sucrose phosphorylase has at least the characteristic (D):

(D) aG1P formation activity in 24 hours from 1M sucrose and 1M phosphate at 30° C. using 20 U heat-purified sucrose phosphorylase of at least 300 mM up to 1000 mM, at least 350 mM up to 1000 mM, at least 354 mM up to 1000 mM, at least 367 mM up to 1000 mM, at least 400 mM up to 1000 mM, at least 422 mM up to 1000 mM, at least 450 mM up to 1000 mM, at least 484 mM up to 1000 mM, at least 500 mM up to 1000 mM, at least 501 mM up to 1000 mM, preferably of at least 300 mM up to 750 mM, at least 350 mM up to 750 mM, at least 354 mM up to 750 mM, at least 367 mM up to 750 mM, at least 400 mM up to 750 mM, at least 422 mM up to 750 mM, at least 450 mM up to 750 mM, at least 484 mM up to 750 mM, at least 500 mM up to 750 mM, at least 501 mM up to 750 mM, more preferably at least 300 mM up to 600 mM, at least 350 mM up to 600 mM, at least 354 mM up to 600 mM, at least 367 mM up to 600 mM, at least 400 mM up to 600 mM, at least 422 mM up to 600 mM, at least 450 mM up to 600 mM, at least 484 mM up to 600 mM, at least 500 mM up to 600 mM, at least 501 mM up to 600 mM, even more preferably at least 300 mM up to 550 mM, at least 350 mM up to 550 mM, at least 354 mM up to 550 mM, at least 367 mM up to 550 mM, at least 400 mM up to 550 mM, at least 422 mM up to 550 mM, at least 450 mM up to 550 mM, at least 484 mM up to 550 mM, at least 500 mM up to 550 mM, at least 501 mM up to 550 mM, and most preferably of at least 300 mM up to 501 mM, at least 350 mM up to 501 mM, at least 354 mM up to 501 mM, at least 367 mM up to 501 mM, at least 400 mM up to 501 mM, at least 422 mM up to 501 mM, at least 450 mM up to 501 mM, at least 484 mM up to 501 mM in aG1P formation assay.

In a preferred embodiment of the second aspect, which is also a preferred embodiment of all previous embodiments, the sucrose phosphorylase is the sucrose phosphorylase as defined by any one of the embodiments described above.

Preferably, the sucrose phosphorylase is the sucrose phosphorylase of SEQ ID NO: 1, 2, 3, 4, 6, 7, 8, 9, 10, 11, 12, 13, 14, 15, 16, 17, and 18, preferably of SEQ ID NO: 1, 6, 7, 8, 9, 10, 11, 12, 13, 14, 15, 16, 17, and 18, more preferably of SEQ ID NO: 1, 7, 8, 9, 10, 11, 13, 17, and 18, even more preferably of SEQ ID NO: 1, 10, 11, 13, 17, and most preferably of SEQ ID NO: 1, and 17.

In yet another preferred embodiment of the second aspect, which is also a preferred embodiment to any one of the previous embodiments thereto, the sucrose phosphorylase has at least the characteristic (A) and/or (B):

(A) a thermal stability of a Tm50 value of at least 66.5° C. up to 90° C., at least 67.0° C. up to 90° C., at least 67.5° C. up to 90° C., at least 68.0° C. up to 90° C., at least 68.5° C. up to 90° C., at least 69.0° C. up to 90° C., at least 69.5° C. up to 90° C., at least 70.0° C. up to 90° C., at least 70.5° C. up to 90° C., at least 71.0° C. up to 90° C., at least 71.5° C. up to 90° C., at least 72.0° C. up to 90° C., preferably of at least 68.0° C. up to 90° C., at least 68.5° C. up to 90° C., at least 69.0° C. up to 90° C., at least 69.5° C. up to 90° C., at least 70.0° C. up to 90° C., at least 70.5° C. up to 90° C., at least 71.0° C. up to 90° C., at least 71.5° C. up to 90° C., at least 72.0° C. up to 90° C., more preferably of at least 70.0° C. up to 90° C., at least 70.5° C. up to 90° C., at least 71.0° C. up to 90° C., at least 71.5° C. up to 90° C., at least 72.0° C. up to 90° C., and most preferably of at least 68.0° C. up to 85° C., at least 68.5° C. up to 85° C., at least 69.0° C. up to 85° C., at least 69.5° C. up to 85° C., at least 70.0° C. up to 85° C., at least 70.5° C. up to 85° C., at least 71.0° C. up to 85° C., at least 71.5° C. up to 85° C., at least 72.0° C. up to 85° C., of at least 68.0° C. up to 80° C., at least 68.5° C. up to 80° C., at least 69.0° C. up to 80° C., at least 69.5° C. up to 80° C., at least 70.0° C. up to 80° C., at least 70.5° C. up to 80° C., at least 71.0° C. up to 80° C., at least 71.5° C. up to 80° C., at least 72.0° C. up to 80° C., of at least 68.0° C. up to 75° C., at least 68.5° C. up to 75° C., at least 69.0° C. up to 75° C., at least 69.5° C. up to 75° C., at least 70.0° C. up to 75° C., at least 70.5° C. up to 75° C., at least 71.0° C. up to 75° C., at least 71.5° C. up to 75° C., at least 72.0° C. up to 75° C., and utmost preferably of at least 68.0° C. up to 72° C., at least 68.5° C. up to 72° C., or at least 68.0° C. up to 70° C.;

(B) a thermal stability of residual activity after 15 min incubation at 70° C. of at least 25% up to 100%, at least 26% up to 100%, at least 27% up to 100%, at least 28% up to 100%, at least 29% up to 100%, at least 30% up to 100%, at least 31% up to 100%, at least 32% up to 100%, at least 33% up to 100%, at least 34% up to 100%, at least 35% up to 100%, at least 36% up to 100%, at least 37% up to 100%, at least 38% up to 100%, at least 39% up to 100%, at least 40% up to 100%, at least 41% up to 100%, at least 42% up to 100%, at least 43% up to 100%, at least 44% up to 100%, at least 45% up to 100%, at least 46% up to 100%, at least 47% up to 100%, at least 48% up to 100%, at least 49% up to 100%, at least 50% up to 100%, at least 51% up to 100%, at least 52% up to 100%, at least 53% up to 100%, at least 54% up to 100%, at least 55% up to 100%, at least 56% up to 100%, at least 57% up to 100%, at least 58% up to 100%, at least 59% up to 100%, 60% up to 100%, at least 61% up to 100%, at least 62% up to 100%, at least 63% up to 100%, at least 64% up to 100%, preferably at least 40% up to 100%, at least 41% up to 100%, at least 42% up to 100%, at least 43% up to 100%, at least 44% up to 100%, at least 45% up to 100%, at least 46% up to 100%, at least 47% up to 100%, at least 48% up to 100%, at least 49% up to 100%, at least 50% up to 100%, at least 51% up to 100%, at least 52% up to 100%, at least 53% up to 100%, at least 54% up to 100%, at least 55% up to 100%, at least 56% up to 100%, at least 57% up to 100%, at least 58% up to 100%, at least 59% up to 100%, 60% up to 100%, at least 61% up to 100%, at least 62% up to 100%, at least 63% up to 100%, at least 64% up to 100%, more preferably of at least 50% up to 100%, at least 51% up to 100%, at least 52% up to 100%, at least 53% up to 100%, at least 54% up to 100%, at least 55% up to 100%, at least 56% up to 100%, at least 57% up to 100%, at least 58% up to 100%, at least 59% up to 100%, 60% up to 100%, at least 61% up to 100%, at least 62% up to 100%, at least 63% up to 100%, at least 64% up to 100%, and most preferably of at least of at least 50% up to 64%, at least 51% up to 64%, at least 52% up to 64%, at least 53% up to 64%, at least 54% up to 64%, at least 55% up to 64%, at least 56% up to 64%, at least 57% up to 64%, at least 58% up to 64%, at least 59% up to 64%, 60% up to 64%, at least 61% up to 64%, at least 62% up to 64%, at least 63% up to 64%, and utmost preferably of 64%.

In a preferred embodiment of the second aspect, which is also a preferred embodiment of all previous embodiments, the sucrose phosphorylase is the sucrose phosphorylase as defined by any one of the embodiments described above.

Preferably, the sucrose phosphorylase is the sucrose phosphorylase of SEQ ID NO: 6, 7, 8, 9, 10, 11, 13, 14, 15, 16, 17, and 18, preferably of SEQ ID NO: 6, 7, 8, 9, 10, 11, 13, 14, 17, and 18, more preferably of SEQ ID NO: 7, 8, 9, 10, 11, 13, 17, and 18, even more preferably of SEQ ID NO: 10, 11, 13, 17, and most preferably of SEQ ID NO: 11, and 17, and utmost preferably of SEQ ID NO: 17.

The sucrose phosphorylase of the present invention, preferably the sucrose phosphorylase of the second aspect including all embodiments relating thereto, is capable of catalyzing the phosphorolytic cleavage of substrate glucoside into aG1P and a co-product.

Preferably, the sucrose phosphorylase is capable of catalyzing the phosphorolytic cleavage of a substrate glucoside, wherein the substrate glucoside is sucrose.

More preferably, the sucrose phosphorylase is capable of catalyzing the phosphorolytic cleavage of a substrate glucoside to aG1 P and a co-product, wherein the co-product is fructose.

Preferably, the reaction of aG1P and the co-product is reversible.

In another preferred embodiment of the second aspect, which is also a preferred embodiment of all embodiments relating thereto, the sucrose phosphorylase is capable of catalyzing the phosphorolytic cleavage of a substrate glucoside to aG1P and a co-product, which aG1P is enzymatically converted by at least one further enzyme into a final product.

Preferably, the final product is selected from the group consisting of trehalose, cellobiose, laminaribiose, laminaritriose, laminaritetraose, laminaribiose-oligosaccharides, lacto-N-biose, galacto-N-biose, and kojibiose.

More preferably, the at least one further enzyme for conversion into a final product is selected from the group consisting of trehalose phosphorylase, cellobiose phosphorylase, laminaribiose phosphorylase, lacto-N-biose phosphorylase, UDP-glucose-4-epimerase, UTP-glucose-1-phosphate uridylyltransferase, phosphoglucomutase, glucose 6-phosphate 1-epimerase, beta-phosphoglucomutase, kojibiose phosphorylase, and glucose isomerase.

In another preferred embodiment of the second aspect, which is also a preferred embodiment of all embodiments relating thereto, the sucrose phosphorylase is capable of catalyzing a transglycosylation reaction of a donor glucoside and an acceptor substrate.

Preferably, the sucrose phosphorylase is capable of catalyzing a transglycosylation reaction of a donor glucoside and an acceptor substrate, and wherein the acceptor substrate is selected from the group consisting of a carbohydrate, an alditol, glycerol, 1,2-propanediol and derivatives, carboxy acids and phenolic compounds, preferably glucose, arabinose, sorbose, ketoxylose, ketoarabinose, rhamnulose, fucose, fructose, galactose, xylose, xylitol, arabitol, sorbitol, glycerol, 1,2-propanediol, 2,3-methoxy-1,2-propanediol, 3,3-ethoxy-1,2-propanediol, 4,3-allyloxy-1,2-propanediol, 5,3-tert-butoxy-1,2-propanediol, 6,3-(o-methoxyphenoxy)-1,2-propanediol, caffeic acid, acetate, formate, sodium benzoate, hydrochinone, catechin, epigallocatechin gallate, 4-hydroxy-2,5-dimethyl-3(2H)-furanone, 2-ethyl-4-hydroxy-5-methyl-3(2H)-furanone, and kojic acid.

In another preferred embodiment of the second aspect, which is also a preferred embodiment of all embodiments relating thereto, the sucrose phosphorylase is a sucrose phosphorylase according to EC number EC 2.4.1.7.

Preferably, the sucrose phosphorylase is a sucrose phosphorylase from the group of species consisting of *Bifidobacterium magnum*, *Bifidobacterium animalis*, *Bifidobacterium longum*, *Bifidobacterium thermophilum*, and preferably is the sucrose phosphorylases from *Bifidobacterium magnum*.

In yet another embodiment of the second aspect, the sucrose phosphorylase is a sucrose phosphorylase variant from *Bifidobacterium*, wherein the sucrose phosphorylase provides wherein the sucrose phosphorylase has one or more of the characteristics selected from the group (A), (B) (C), and (D):

(A) a Tm50 value of at least 66.5° C. up to 90° C., at least 67.0° C. up to 90° C., at least 67.5° C. up to 90° C., at least 68.0° C. up to 90° C., at least 68.5° C. up to 90° C., at least 69.0° C. up to 90° C., at least 69.5° C. up to 90° C., at least 70.0° C. up to 90° C., at least 70.5° C. up to 90° C., at least 71.0° C. up to 90° C., at least 71.5° C. up to 90° C., at least 72.0° C. up to 90° C., preferably of at least 68.0° C. up to 90° C., at least 68.5° C. up to 90° C., at least 69.0° C. up to 90° C., at least 69.5° C. up to 90° C., at least 70.0° C. up to 90° C., at least 70.5° C. up to 90° C., at least 71.0° C. up to 90° C., at least 71.5° C. up to 90° C., at least 72.0° C. up to 90° C., more preferably of at least 70.0° C. up to 90° C., at least 70.5° C. up to 90° C., at least 71.0° C. up to 90° C., at least 71.5° C. up to 90° C., at least 72.0° C. up to 90° C., and most preferably of at least 68.0° C. up to 85° C., at least 68.5° C. up to 85° C., at least 69.0° C. up to 85° C., at least 69.5° C. up to 85° C., at least 70.0° C. up to 85° C., at least 70.5° C. up to 85° C., at least 71.0° C. up to 85° C., at least 71.5° C. up to 85° C., at least 72.0° C. up to 85° C., of at least 68.0° C. up to 80° C., at least 68.5° C. up to 80° C., at least 69.0° C. up to 80° C., at least 69.5° C. up to 80° C., at least 70.0° C. up to 80° C., at least 70.5° C. up to 80° C., at least 71.0° C. up to 80° C., at least 71.5° C. up to 80° C., at least 72.0° C. up to 80° C., of at least 68.0° C. up to 75° C., at least 68.5° C. up to 75° C., at least 69.0° C. up to 75° C., at least 69.5° C. up to 75° C., at least 70.0° C. up to 75° C., at least 70.5° C. up to 75° C., at least 71.0° C. up to 75° C., at least 71.5° C. up to 75° C., at least 72.0° C. up to 75° C., and utmost preferably of at least 68.0° C. up to 72° C., at least 68.5° C. up to 72° C., or at least 68.0° C. up to 70° C.;

(B) residual activity after 15 min incubation at 70° C. of at least 25% up to 100%, at least 26% up to 100%, at least 27% up to 100%, at least 28% up to 100%, at least 29% up to 100%, at least 30% up to 100%, at least 31% up to 100%, at least 32% up to 100%, at least 33% up to 100%, at least 34% up to 100%, at least 35% up to 100%, at least 36% up to 100%, at least 37% up to 100%, at least 38% up to 100%, at least 39% up to 100%, at least 40% up to 100%, at least 41% up to 100%, at least 42% up to 100%, at least 43% up to 100%, at least 44% up to 100%, at least 45% up to 100%, at least 46% up to 100%, at least 47% up to 100%, at least 48% up to 100%, at least 49% up to 100%, at least 50% up to 100%, at least 51% up to 100%, at least 52% up to 100%, at least 53% up to 100%, at least 54% up to 100%, at least 55% up to 100%, at least 56% up to 100%, at least 57% up to 100%, at least 58% up to 100%, at least 59% up to 100%, 60% up to 100%, at least 61% up to 100%, at least 62% up to 100%, at least 63% up to 100%, at least 64% up to 100%, preferably at least 40% up to 100%, at least 41% up to 100%, at least 42% up to 100%, at least 43% up to 100%, at least 44% up to 100%, at least 45% up to 100%, at least 46% up to 100%, at least 47% up to 100%, at least 48% up to 100%, at least 49% up to 100%, at least 50% up to 100%, at least 51% up to 100%, at least 52% up to 100%, at least 53% up to 100%, at least 54% up to 100%, at least 55% up to 100%, at least 56% up to 100%, at least 57% up to 100%, at least 58% up to 100%, at least 59% up to 100%, 60% up to 100%, at least 61% up to 100%, at least 62% up to 100%, at least 63% up to 100%, at least 64% up to 100%, more preferably of at least 50% up to 100%, at least 51% up to 100%, at least 52% up to 100%, at least 53% up to 100%, at least 54% up to 100%, at least 55% up to 100%, at least 56% up to 100%, at least 57% up to 100%, at least 58% up to 100%, at least 59% up to 100%, 60% up to 100%, at least 61% up to 100%, at least 62% up to 100%, at least 63% up to 100%, at least 64% up to 100%, and most preferably of at least of at least 50% up to 64%, at least 51% up to 64%, at least 52% up to 64%, at least 53% up to 64%, at least 54% up to 64%, at least 55% up to 64%, at least 56% up to 64%, at least 57% up to 64%, at least 58% up to 64%, at least 59% up to 64%, 60% up to 64%, at least 61% up to 64%, at least 62% up to 64%, at least 63% up to 64%, and utmost preferably of 64%;

(C) P/H-ratio of at least 200% up to 600%, at least 250% up to 600%, at least 275% up to 600%, at least 296% up to 600%, at least 299% up to 600%, at least 300% up to 600%, at least 331% up to 600%, at least 350% up to 600%, at least 354% up to 600%, at least 360% up to 600%, at least 370% up to 600%, at least 373% up to 600%, preferably of at least 200% up to 500%, at least 250% up to 500%, at least 275% up to 500%, at least 296% up to 500%, at least 299% up to 500%, at least 300% up to 500%, at least 331% up to 500%, at least 350% up to 500%, at least 354% up to 500%, at least 360% up to 500%, at least 370% up to 500%, at least 373% up to 500%, more preferably of at least 200% up to 450%, at least 250% up to 450%, at least 275% up to 450%, at least 296% up to 450%, at least 299% up to 450%, at least 300% up to 450%, at least 331% up to 450%, at least 350% up to 450%, at least 354% up to 450%, at least 360% up to 450%, at least 370% up to 450%, at least 373% up to 450%, even more preferably of at least 200% up to 400%, at least 250% up to 400%, at least 275% up to 400%, at least 296% up to 400%, at least 299% up to 400%, at least 300% up to 400%, at least 331% up to 400%, at least 350% up to 400%, at least 354% up to 400%, at least 360% up to 400%, at least 370% up to 400%, at least 373% up to 400%, and most preferably of at least 275% up to 373%, at least 296% up to 373%, at least 299% up to 373%, at least 300% up to 373%, at least 331% up to 373%;

(D) aG1P formation activity in 24 hours from 1M sucrose and 1M phosphate at 30° C. using 20 U heat-purified sucrose phosphorylase of at least 300 mM up to 1000 mM, at least 350 mM up to 1000 mM, at least 354 mM up to 1000 mM, at least 367 mM up to 1000 mM, at least 400 mM up to 1000 mM, at least 422 mM up to 1000 mM, at least 450 mM up to 1000 mM, at least 484 mM up to 1000 mM, at least 500 mM up to 1000 mM, at least 501 mM up to 1000 mM, preferably of at least 300 mM up to 750 mM, at least 350 mM up to 750 mM, at least 354 mM up to 750 mM, at least 367 mM up to 750 mM, at least 400 mM up to 750 mM, at least 422 mM up to 750 mM, at least 450 mM up to 750 mM, at least 484 mM up to 750 mM, at least 500 mM up to 750 mM, at least 501 mM up to 750 mM, more preferably at least 300 mM up to 600 mM, at least 350 mM up to 600 mM, at least 354 mM up to 600 mM, at least 367 mM up to 600 mM, at least 400 mM up to 600 mM, at least 422 mM up to 600 mM, at least 450 mM up to 600 mM, at least 484 mM up to 600 mM, at least 500 mM up to 600 mM, at least 501 mM up to 600 mM, even more preferably at least 300 mM up to 550 mM, at least 350 mM up to 550 mM, at least 354 mM up to 550 mM, at least 367 mM up to 550 mM, at least 400 mM up to 550 mM, at least 422 mM up to 550 mM, at least 450 mM up to 550 mM, at least 484 mM up to 550 mM, at least 500 mM up to 550 mM, at least 501 mM up to 550 mM, and most preferably of at least 300 mM up to 501 mM, at least 350 mM up to 501 mM, at least 354 mM up to 501 mM, at least 367 mM up to 501 mM, at least 400 mM up to 501 mM, at least 422 mM up to 501 mM, at least 450 mM up to 501 mM, at least 484 mM up to 501 mM.

Preferably, the sucrose phosphorylase has two or more characteristics selected from the group consisting of the characteristics (A) and (B), (A) and (C), (A) and (D), (B) and (C), (B) and (D), (C) and (D), (A) and (B) and (C), (A) and (B) and (D), (A) and (C) and (D), and (A) and (B) and (C) and (D), and preferably (A) and (B) and (C).

More preferably, the sucrose phosphorylase variant is a variant of the sucrose phosphorylases from the group of species consisting of *Bifidobacterium magnum*, *Bifidobacterium animalis*, *Bifidobacterium longum*, *Bifidobacterium thermophilum*, and preferably is a variant of the sucrose phosphorylases from *Bifidobacterium magnum*.

Even more preferably, the sucrose phosphorylase variant is a variant of the sucrose phosphorylases from any one of the first or second aspect of the invention hereof.

In a third aspect, the invention relates to a method for preparing aG1P and a co-product, wherein the method comprises reacting a glucoside substrate with a sucrose phosphorylase as defined in any one of the aspects and embodiments of the invention described above.

Preferably, the method comprises reacting a sucrose substrate with a sucrose phosphorylase as defined in any one of the aspects and embodiments of the invention described above, wherein the co-product is fructose.

The invention further relates to a method for preparing a glucoside product, wherein the method comprises the steps of
  (i) reacting a glucoside substrate with a sucrose phosphorylase to create a co-product and aG1P intermediate;
  (ii) reacting the aG1P intermediate and a glucoside acceptor molecule and one or more additional enzymes to create a glucoside final product.

Preferably, the method of the invention is defined in that the
  (i) the glucoside substrate is preferably sucrose;
  (ii) the glucoside final product is selected from group comprising the glucoside products trehalose, cellobiose, laminaribiose, laminaritriose, laminaritetraose, laminaribiose-oligosaccharides, lacto-N-biose, galacto-N-biose, and kojibiose;
(iii) the one or more additional enzyme(s) for conversion into a final product is/are selected from the group consisting of trehalose phosphorylase, cellobiose phosphorylase, laminaribiose phosphorylase, lacto-N-biose phosphorylase, UDP-glucose-4-epimerase, UTP-glucose-1-phosphate uridylyltransferase, phosphoglucomutase, glucose 6-phosphate 1-epimerase, beta-phosphoglucomutase, kojibiose phosphorylase, and glucose isomerase.

In a preferred embodiment, the co-product is separated from aG1P between steps (i) corresponding to reacting a glucoside substrate with a sucrose phosphorylase to create a co-product and aG1P intermediate and step (ii) corresponding to reacting the aG1P intermediate and a glucoside acceptor molecule and one or more additional enzymes to create a glucoside final product.

Preferably, the steps (i) and (ii) of the embodiment described hereunder are done simultaneously and in the same reaction vessels.

In a preferred embodiment, the steps (i) and (ii) are done in separate vessels.

The invention also relates to a method for preparing a transglycosylated product, wherein the method comprises reacting a donor glucoside substrate with a sucrose phosphorylase and an acceptor substrate to create a transglycosylated product.

The method is preferably a method, wherein
(i) wherein the donor glucoside substrate is preferably sucrose; and/or
(ii) wherein the acceptor substrate is selected from the group consisting of a carbohydrate, an alditol, glycerol, 1,2-propanediol and derivatives, carboxy acids and phenolic compounds, preferably glucose, arabinose, sorbose, ketoxylose, ketoarabinose, rhamnulose, fucose, fructose, galactose, xylose, xylitol, arabitol, sorbitol, glycerol, 1,2-propanediol, 2,3-methoxy-1,2-propanediol, 3,3-ethoxy-1,2-propanediol, 4,3-allyloxy-1,2-propanediol, 5,3-tert-butoxy-1,2-propanediol, 6,3-(o-methoxyphenoxy)-1,2-propanediol, caffeic acid, acetate, formate, sodium benzoate, hydrochinone, catechin, epigallocatechin gallate, 4-hydroxy-2,5-dimethyl-3(2H)-furanone, 2-ethyl-4-hydroxy-5-methyl-3(2H)-furanone, and kojic acid.

In the context of the third aspect including all embodiments relating thereto, the sucrose phosphorylase is preferably a sucrose phosphorylase according to EC number EC 2.4.1.7.

In another preferred embodiment of the third aspect, which is also a preferred embodiment of all embodiments relating thereto, the sucrose phosphorylase is a sucrose phosphorylases from the group of species consisting of *Bifidobacterium magnum*, *Bifidobacterium animalis*, *Bifidobacterium longum*, *Bifidobacterium thermophilum*, and preferably is the sucrose phosphorylases from *Bifidobacterium magnum*.

In another even more preferred embodiment of the third aspect, which is also a preferred embodiment of all embodiments relating thereto, the sucrose phosphorylase variant is a variant of the sucrose phosphorylases from any one of the first or second aspect of the invention hereof.

Preferably, the method comprises reacting a glucoside substrate with a sucrose phosphorylase as defined in any one of the aspects and the embodiments defined above.

In another preferred embodiment of the third aspect, which is also an embodiment of all embodiments relating thereto, the method comprises reacting a glucoside substrate with a sucrose phosphorylase of SEQ ID NO: 1, 2, 3, 4, 6, 7, 8, 9, 10, 11, 13, 14, 15, 16, 17, and 18, preferably of SEQ ID NO: 1, 6, 7, 8, 9, 10, 11, 13, 14, 15, 16, 17, and 18, more preferably of SEQ ID NO: 1, 7, 8, 9, 10, 11, 13, 17, and 18, even more preferably of SEQ ID NO: 1, 10, 11, 13, 17, and most preferably of SEQ ID NO: 1, and 17.

The present invention is further related to methods according to the third aspect of the invention and any of the embodiments thereto, for creating
a) aG1P and a co-product; and/or
b) aG1P and a co-product, wherein the aG1P intermediate and a glucoside acceptor molecule are further reacting by use of one or more additional enzymes to create a glucoside final product; and/or
c) a transglycosylated product,
by using a sucrose phosphorylase according to any aspect of the invention and their embodiments.

Accordingly, in another preferred embodiment, the method of the invention aims at producing a sucrose phosphorylase, wherein the sucrose phosphorylase has at least one of the characteristics (A), (B), (C), (D), or any combination thereof:
(A) a Tm50 value of at least 66.5° C. up to 90° C., at least 67.0° C. up to 90° C., at least 67.5° C. up to 90° C., at least 68.0° C. up to 90° C., at least 68.5° C. up to 90° C., at least 69.0° C. up to 90° C., at least 69.5° C. up to 90° C., at least 70.0° C. up to 90° C., at least 70.5° C. up to 90° C., at least 71.0° C. up to 90° C., at least 71.5° C. up to 90° C., at least 72.0° C. up to 90° C., preferably of at least 68.0° C. up to 90° C., at least 68.5° C. up to 90° C., at least 69.0° C. up to 90° C., at least 69.5° C. up to 90° C., at least 70.0° C. up to 90° C., at least 70.5° C. up to 90° C., at least 71.0° C. up to 90° C., at least 71.5° C. up to 90° C., at least 72.0° C. up to 90° C., more preferably of at least 70.0° C. up to 90° C., at least 70.5° C. up to 90° C., at least 71.0° C. up to 90° C., at least 71.5° C. up to 90° C., at least 72.0° C. up to 90° C., and most preferably of at least 68.0° C. up to 85° C., at least 68.5° C. up to 85° C., at least 69.0° C. up to 85° C., at least 69.5° C. up to 85° C., at least 70.0° C. up to 85° C., at least 70.5° C. up to 85° C., at least 71.0° C. up to 85° C., at least 71.5° C. up to 85° C., at least 72.0° C. up to 85° C., of at least 68.0° C. up to 80° C., at least 68.5° C. up to 80° C., at least 69.0° C. up to 80° C., at least 69.5° C. up to 80° C., at least 70.0° C. up to 80° C., at least 70.5° C. up to 80° C., at least 71.0° C. up to 80° C., at least 71.5° C. up to 80° C., at least 72.0° C. up to 80° C., of at least 68.0° C. up to 75° C., at least 68.5° C. up to 75° C., at least 69.0° C. up to 75° C., at least 69.5° C. up to 75° C., at least 70.0° C. up to 75° C., at least 70.5° C. up to 75° C., at least 71.0° C. up to 75° C., at least 71.5° C. up to 75° C., at least 72.0° C. up to 75° C., and utmost preferably of at least 68.0° C. up to 72° C., at least 68.5° C. up to 72° C., or at least 68.0° C. up to 70° C.;
(B) residual activity after 15 min incubation at 70° C. of at least 25% up to 100%, at least 26% up to 100%, at least 27% up to 100%, at least 28% up to 100%, at least 29% up to 100%, at least 30% up to 100%, at least 31% up to 100%, at least 32% up to 100%, at least 33% up to 100%, at least 34% up to 100%, at least 35% up to 100%, at least 36% up to 100%, at least 37% up to 100%, at least 38% up to 100%, at least 39% up to 100%, at least 40% up to 100%, at least 41% up to 100%, at least 42% up to 100%, at least 43% up to 100%, at least 44% up to 100%, at least 45% up to 100%, at least 46% up to 100%, at least 47% up to 100%, at least 48% up to 100%, at least 49% up to 100%, at least 50% up to 100%, at least 51% up to 100%, at least 52% up to 100%, at least 53% up to 100%, at least 54% up to 100%, at least 55% up to 100%, at least 56% up to 100%, at least 57% up to 100%, at least 58% up to 100%, at least 59% up to 100%, 60% up to 100%, at least 61% up to 100%, at least 62% up to 100%, at least 63% up to 100%, at least 64% up to 100%, preferably at least 40% up to 100%, at least 41% up to 100%, at least 42% up to 100%, at least 43% up to 100%, at least 44% up to 100%, at least 45% up to 100%, at least 46% up to 100%, at least 47% up to 100%, at least 48% up to 100%, at least 49% up to 100%, at least 50% up to 100%, at least 51% up to 100%, at least 52% up to 100%, at least 53% up to 100%, at least 54% up to 100%, at least 55% up to 100%, at least 56% up to 100%, at least 57% up to 100%, at least 58% up to 100%, at least 59% up to 100%, 60% up to 100%, at least 61% up to 100%, at least 62% up to 100%, at least 63% up to 100%, at least 64% up to 100%, more preferably of at least 50% up to 100%, at least 51% up to 100%, at least 52% up to 100%, at least 53% up to 100%, at least 54% up to 100%, at least 55% up to 100%, at least 56% up to 100%, at least 57% up to 100%, at least 58% up to 100%, at least 59% up to 100%, 60% up to 100%, at least 61% up to 100%, at least 62% up to 100%, at least 63% up to 100%, at least 64% up to 100%, and most preferably of at least of at least 50% up to 64%, at least 51% up to 64%, at least 52% up to 64%, at least 53% up to 64%, at least 54% up to 64%, at least 55% up to 64%, at least 56% up to 64%, at least 57% up to 64%, at least 58% up to 64%, at least 59% up to 64%, 60% up to 64%, at least 61% up to 64%, at least 62% up to 64%, at least 63% up to 64%, and utmost preferably of 64%;

(C) P/H-ratio of at least 200% up to 600%, at least 250% up to 600%, at least 275% up to 600%, at least 296% up to 600%, at least 299% up to 600%, at least 300% up to 600%, at least 331% up to 600%, at least 350% up to 600%, at least 354% up to 600%, at least 360% up to 600%, at least 370% up to 600%, at least 373% up to 600%, preferably of at least 200% up to 500%, at least 250% up to 500%, at least 275% up to 500%, at least 296% up to 500%, at least 299% up to 500%, at least 300% up to 500%, at least 331% up to 500%, at least 350% up to 500%, at least 354% up to 500%, at least 360% up to 500%, at least 370% up to 500%, at least 373% up to 500%, more preferably of at least 200% up to 450%, at least 250% up to 450%, at least 275% up to 450%, at least 296% up to 450%, at least 299% up to 450%, at least 300% up to 450%, at least 331% up to 450%, at least 350% up to 450%, at least 354% up to 450%, at least 360% up to 450%, at least 370% up to 450%, at least 373% up to 450%, even more preferably of at least 200% up to 400%, at least 250% up to 400%, at least 275% up to 400%, at least 296% up to 400%, at least 299% up to 400%, at least 300% up to 400%, at least 331% up to 400%, at least 350% up to 400%, at least 354% up to 400%, at least 360% up to 400%, at least 370% up to 400%, at least 373% up to 400%, and most preferably of at least 275% up to 373%, at least 296% up to 373%, at least 299% up to 373%, at least 300% up to 373%, at least 331% up to 373%;

(D) aG1P formation activity in 24 hours from 1M sucrose and 1M phosphate at 30° C. using 20 U heat-purified sucrose phosphorylase of at least 300 mM up to 1000 mM, at least 350 mM up to 1000 mM, at least 354 mM up to 1000 mM, at least 367 mM up to 1000 mM, at least 400 mM up to 1000 mM, at least 422 mM up to 1000 mM, at least 450 mM up to 1000 mM, at least 484 mM up to 1000 mM, at least 500 mM up to 1000 mM, at least 501 mM up to 1000 mM, preferably of at least 300 mM up to 750 mM, at least 350 mM up to 750 mM, at least 354 mM up to 750 mM, at least 367 mM up to 750 mM, at least 400 mM up to 750 mM, at least 422 mM up to 750 mM, at least 450 mM up to 750 mM, at least 484 mM up to 750 mM, at least 500 mM up to 750 mM, at least 501 mM up to 750 mM, more preferably at least 300 mM up to 600 mM, at least 350 mM up to 600 mM, at least 354 mM up to 600 mM, at least 367 mM up to 600 mM, at least 400 mM up to 600 mM, at least 422 mM up to 600 mM, at least 450 mM up to 600 mM, at least 484 mM up to 600 mM, at least 500 mM up to 600 mM, at least 501 mM up to 600 mM, even more preferably at least 300 mM up to 550 mM, at least 350 mM up to 550 mM, at least 354 mM up to 550 mM, at least 367 mM up to 550 mM, at least 400 mM up to 550 mM, at least 422 mM up to 550 mM, at least 450 mM up to 550 mM, at least 484 mM up to 550 mM, at least 500 mM up to 550 mM, at least 501 mM up to 550 mM, and most preferably of at least 300 mM up to 501 mM, at least 350 mM up to 501 mM, at least 354 mM up to 501 mM, at least 367 mM up to 501 mM, at least 400 mM up to 501 mM, at least 422 mM up to 501 mM, at least 450 mM up to 501 mM, at least 484 mM up to 501 mM.

Preferably, in this context, the sucrose phosphorylase is a sucrose phosphorylase according to EC number EC 2.4.1.7.

In another preferred embodiment, the sucrose phosphorylase is an sucrose phosphorylases from the group of species consisting of *Bifidobacterium magnum*, *Bifidobacterium animalis*, *Bifidobacterium longum*, *Bifidobacterium thermophilum*, and preferably is the sucrose phosphorylases from *Bifidobacterium magnum*.

More preferably, the method comprises reacting a glucoside substrate with a sucrose phosphorylase as defined in any one of the aspects and of the embodiments defined herein.

In another preferred embodiment of this aspect, the method comprises reacting a glucoside substrate with a sucrose phosphorylase of SEQ ID NO: 1, 2, 3, 4, 6, 7, 8, 9, 10, 11, 13, 14, 15, 16, 17, and 18, preferably of SEQ ID NO: 1, 6, 7, 8, 9, 10, 11, 13, 14, 15, 16, 17, and 18, more preferably of SEQ ID NO: 1, 7, 8, 9, 10, 11, 13, 17, and 18, even more preferably of SEQ ID NO: 1, 10, 11, 13, 17, and most preferably of SEQ ID NO: 1, and 17.

In a $4^{th}$ aspect, the present invention relates to a method for increasing of the thermal stability of a sucrose phosphorylase which can be aligned to the sucrose phosphorylase of SEQ ID NO: 1, which method comprises (i) aligning an amino acid sequence of a first sucrose phosphorylase with an amino acid sequence of a second sucrose phosphorylase;

(ii) identifying one or more amino acid positions of the amino acid sequence of the second sucrose phosphorylase which correspond to one or more amino acid positions of the amino acid sequence of the first sucrose phosphorylase, wherein substitution of an amino acid residue at the one or more amino acid positions of the amino acid sequence of the first sucrose phosphorylase increases thermal stability of the first sucrose phosphorylase;

(iii) substituting an amino acid residue at the one or more amino acid positions of the second sucrose phosphorylase corresponding to the one or more amino acid positions of the amino acid sequence of the first sucrose phosphorylase, wherein substitution of an amino acid residue at the one or more amino acid position of the amino acid sequence of the first sucrose phosphorylase increases thermal stability of the first sucrose phosphorylase;

(iv) testing whether the substituted amino acid residue at the one or more amino acid positions of the second sucrose phosphorylase corresponding to the one or more amino acid positions of the amino acid sequence of the sucrose phosphorylase, results in increased thermal stability of the second sucrose phosphorylase compared to the thermal stability of the first sucrose phosphorylase;

wherein the first sucrose phosphorylase is a sucrose phosphorylase comprising an amino acid sequence according to SEQ ID NO: 1.

In a preferred embodiment, the method comprises the selected one or more amino acids positions of the second sucrose phosphorylase, which amino acid residue at the one or more amino acid positions of the second sucrose phosphorylase are aligning and corresponding to the one or more amino acid positions of the amino acid sequence of the first sucrose phosphorylase, is substituted such that the substituted amino acid residue results in increased thermal stability of the second sucrose phosphorylase.

In a preferred embodiment of this aspect, the homology and/or identity between the amino acid sequence of the first sucrose phosphorylase and the amino acid sequence of the second sucrose phosphorylase is at least 75%.

More preferably, the homology and/or identity is at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%, preferably the homology and/or identity is at least 99.1%, or at least 99.2%, or at least 99.3%, or at least 99.4%, or at least 99.5%, or at least 99.6%, or at least 99.7%, or at least 99.8%, and in particular at least 99.9%, or 100%.

Even more preferably, the one or more amino acid positions of the amino acid sequence of the first sucrose is/are each and individually selected from the group consisting of amino acid positions of SEQ ID NO: 1 positions E92, S124, A148, Q188, I231, L371, T461, preferably is/are selected from the group consisting of the amino acids positions E92, S124, A148, Q188, I231, more preferably is/are selected from the group consisting of the amino acids positions S124, A148, Q188 and most preferably is/are selected from the group consisting of the amino acids positions A148, Q188.

In another preferred embodiment of the $4^{th}$ aspect, which is also a preferred embodiment of all embodiments relating thereto, the amino acid sequence is substituted compared to SEQ ID NO: 1 such that it comprises one or more substitution at one or more amino acid positions, wherein substitution at the one or more amino acid positions is/are each and independently selected from the group consisting of the substitutions:

(i) position E92 is substituted with A, R, N, D, C, Q, G, H, I, L, K, M, F, P, S, T, W, Y, or V; preferably is substituted with A, I, L, or V; and most preferably is substituted with L;

(ii) position S124 is substituted with A, R, N, D, C, Q, E, G, H, I, L, K, M, F, P, T, W, Y, or V; preferably is substituted with R, H, K, N, M, C, S, T, or Q; even more preferably is substituted with Q, K, or T; still even more preferably is substituted with K, T; and most preferably substituted with K;

(iii) position A148 is substituted with R, N, D, C, Q, E, G, H, I, L, K, M, F, P, S, T, W, Y, or V; preferably is substituted with R, H, or K; more preferably is substituted with K, or R; and most preferably with K;

(iv) position T157 is substituted with A, R, N, D, C, Q, E, G, H, I, L, K, M, F, P, S, W, Y, or V; and preferably substituted with D;

(v) position Q188 is substituted with A, R, N, D, C, E, G, H, I, L, K, M, F, P, S, T, W, Y, or V; [preferably is substituted with F, W, or Y; and most preferably is substituted with Y;

(vi) position I231 is substituted with A, R, N, D, C, Q, E, G, H, L, K, M, F, P, S, T, W, Y, or V; preferably is substituted with A, I, L, or V; and most preferably is substituted with V;

(vii) position L371 is substituted with A, R, N, D, C, Q, E, G, H, I, K, M, F, P, S, T, W, Y, or V; preferably is substituted with A, I, L, or V; and most preferably is substituted with A;

(viii) position T461 is substituted with A, R, N, D, C, Q, E, G, H, I, L, K, M, F, P, S, W, Y, or V; preferably is substituted with G, or P; and most preferably is substituted with G.

The present invention also relates to the use of sucrose phoshorylase for preparing aG1P.

Accordingly, in a $5^{th}$ aspect, the invention relates to the use of a sucrose phosphorylase as defined in the context of the present invention, preferably as defined in the context of all previous aspects and embodiments, for the conversion of a glucoside substrate to aG1P and a co-product, wherein (i) the glucoside substrate is selected from group comprising and/or consisting of the glucoside substrates sucrose, maltose, nigerose, and kojibiose;

(ii) the co-product is selected from group comprising and/or consisting of the co-products fructose, and glucose.

In the context of the present invention, the use of a sucrose phosphorylase is preferably for the production of aG1P.

More preferably, the use of a sucrose phosphorylase as defined in any of the embodiments described herein is (i) for the conversion of a glucoside substrate to aG1P intermediate and a co-product, and (ii) for reacting the aG1P intermediate and a glucoside acceptor molecule and one or more additional enzymes to create a glucoside final product.

Even more preferably, the use of a sucrose phosphorylase as defined herein is a use wherein the (i) the glucoside substrate is preferably sucrose;

(ii) the glucoside final product is selected from group comprising the glucoside products trehalose, cellobiose, laminaribiose, laminaritriose, laminaritetraose, laminaribiose-oligosaccharides, lacto-N-biose, galacto-N-biose, kojibiose;

(iii) the one and more additional enzyme(s) for conversion into a final product is/are selected from the group consisting of trehalose phosphorylase, cellobiose phosphorylase, laminaribiose phosphorylase, lacto-N-biose phosphorylase, UDP-glucose-4-epimerase, UTP-glucose-1-phosphate uridylyltransferase, phosphoglucomutase, glucose 6-phosphate 1-epimerase, beta-phosphoglucomutase, kojibiose phosphorylase, glucose isomerase The use of a sucrose phosphorylase according to the present invention is preferably characterized in that the co-product is separated from aG1P between steps (i) corresponding to reacting a glucoside substrate with a sucrose phosphorylase to create a co-product and aG1P intermediate and step (ii) corresponding to reacting the aG1P intermediate and a glucoside acceptor molecule and one or more additional enzymes to create a glucoside final product.

The use of a sucrose phosphorylase according to the present invention is preferably a use wherein the steps (i) and (ii) of the embodiments described above are done simultaneously and in the same reaction vessels.

Preferably, the steps (i) and (ii) are done in separate vessels.

The present invention also relates to the use of a sucrose phosphorylase according to any of the embodiments defined herein for the production of a transglycosylated product, wherein the sucrose phosphorylase is reacted with a donor glucoside substrate and an acceptor substrate to create a transglycosylated product.

In this context, the use of a sucrose phosphorylase is preferably a use
  (i) wherein the donor glucoside substrate is preferably sucrose; and/or
  (ii) wherein the acceptor substrate is selected from the group consisting of a carbohydrate, an alditol, glycerol, 1,2-propanediol and derivatives, carboxy acids and phenolic compounds, preferably glucose, arabinose, sorbose, ketoxylose, ketoarabinose, rhamnulose, fucose, fructose, galactose, xylose, xylitol, arabitol, sorbitol, glycerol, 1,2-propanediol, 2,3-methoxy-1,2-propanediol, 3,3-ethoxy-1,2-propanediol, 4,3-allyloxy-1,2-propanediol, 5,3-tert-butoxy-1,2-propanediol, 6,3-(o-methoxyphenoxy)-1,2-propanediol, caffeic acid, acetate, formate, sodium benzoate, hydrochinone, catechin, epigallocatechin gallate, 4-hydroxy-2,5-dimethyl-3(2H)-furanone, 2-ethyl-4-hydroxy-5-methyl-3 (2H)-furanone, and kojic acid.

In another preferred embodiment of this $5^{th}$ aspect, the sucrose phosphorylase is a sucrose phosphorylase, wherein the sucrose phosphorylase is a sucrose phosphorylase according to EC number EC 2.4.1.7.

In yet another preferred embodiment of this aspect, the sucrose phosphorylase is a sucrose phosphorylases from the group of species consisting of *Bifidobacterium magnum*, *Bifidobacterium animalis*, *Bifidobacterium longum*, *Bifidobacterium thermophilum*, and preferably is the sucrose phosphorylases from *Bifidobacterium magnum*.

In the context of the $5^{th}$ aspect, the sucrose phosphorylase is a sucrose phosphorylase as defined in any one of the aspects of the invention or embodiments defined herein.

Preferably, the sucrose phosphorylase is a sucrose phosphorylase of SEQ ID NO: 1, 2, 3, 4, 6, 7, 8, 9, 10, 11, 13, 14, 15, 16, 17, and 18, preferably of SEQ ID NO: 1, 6, 7, 8, 9, 10, 11, 13, 14, 15, 16, 17, and 18, more preferably of SEQ ID NO: 1, 7, 8, 9, 10, 11, 13, 17, and 18, even more preferably of SEQ ID NO: 1, 10, 11, 13, 17, and most preferably of SEQ ID NO: 1, and 17.

Definition of phosphorolytic activity: For the purpose of this invention, phosphorolytic activity of a sucrose phosphorylase is defined as the activity for phosphorolytic sucrose cleavage to aG1P and fructose. Phosphorolytic activity of a sucrose phosphorylase was routinely assayed using Assay I or Assay II. Assay I comprises using a continuous coupled assay at 30° C. in which the aG1P produced from a sucrose substrate is converted to glucose-6-phosphate by phosphoglucomutase. Glucose-6-phosphate and NADP is converted to 6-phospho-gluconate and NADPH by glucose 6-phosphate dehydrogenase. The detection is based on measuring the absorbance of NADPH at 340 nm. The assay solution contained: 75 mM potassium phosphate buffer pH 7, 2.5 mM NADP, 10 μM glucose 1,6-bisphosphate, 10 mM $MgCl_2$, 250 mM sucrose, 3 U/mL phosphoglucomutase and 3.4 U/mL glucose 6-phosphate dehydrogenase. 1 U is defined as the amount of enzyme that catalyzes the production of 1 μmol of aG1P at the specified conditions. Alternatively, phosphorolytic activity can be determined in an uncoupled assay as described in Assay II: In brief, sucrose phosphorylase is incubated at 30° C. in the presence of 500 mM sucrose and 200 mM potassium phosphate buffer pH 7. At discrete time-points, 20 μl samples were taken and inactivated by the addition of 80 μL 0.25 M HCl. Samples were neutralized and the aG1P-concentration determined as described above. 1 U is defined as the amount of enzyme that catalyzes the production of 1 μmol of aG1P at the specified conditions.

Definition of hydrolytic activity: For the purpose of this invention, hydrolytic activity of a sucrose phosphorylase is defined as the activity for hydrolytic aG1P cleavage to glucose and inorganic phosphate. Hydrolytic activity of a sucrose phosphorylase was routinely measured using Assay III. In Assay III, sucrose phosphorylase was added to a solution containing 100 mM aG1P and 50 mM 2-(N-morpholino)ethanesulfonic acid-buffer pH 7 and incubated at 30° C. At discrete time-points, 100 μl samples were taken and inactivated by the addition of 200 μL 1 M HCl. Samples were neutralized and the aG1P-concentration determined as described in Example 1. In short, a 10 μL sample was added to 90 μL detection reagent containing 48 mM potassium phosphate buffer, 2 mM $MgCl_2$, 0.7 mM NADP, 3.8 mM glucose 6-phosphate dehydrogenase and 3.3 U/mL phosphoglucomutase. After incubation for 20 min at room temperature, the absorbance at 340 nm was determined. The amount of aG1P was quantified with an aG1P calibration curve derived from samples with known amounts of aG1P. Hydrolytic activity was calculated from the initial slope by linear regression of aG1P-concentration over time. 1 U is defined as the amount of enzyme that catalyzes the hydrolytic cleavage of 1 μmol of aG1P per min at the specified conditions. If the sucrose phosphorylase was derived from a non-purified cell free extract, a heat purification step was performed in order to remove the aG1P-degrading activity of the host background. Therefor cell extract was incubated at 55° C. for 15 min. The heat-purified cell free extract containing soluble enzyme was separated from the debris by centrifugation. A decrease in hydrolytic activity of a sucrose phosphorylase of a wild-type enzyme or a variant thereof compared to another wild-type enzyme is indicative of a greater stability of aG1P in a reaction resulting from an inherent enzyme characteristic.

Definition P/H-ratio: The P/H-ratio of a sucrose phosphorylase is the ratio between the phosphorolytic and hydrolytic activity of the respective sucrose phosphorylase. It is calculated by dividing the phosphorolytic activity determined using Assay I of such sucrose phosphorylase by the hydrolytic activity determined using Assay III of the same sucrose phosphorylase and multiplying the value by 100 to obtain the P/H-ratio for such sucrose phosphorylase in percent.

Definition thermal stability: For the purpose of the specification, thermal stability of a sucrose phosphorylase is the property of such enzyme to retain enzymatic activity upon incubation at elevated temperatures for a given time. The sucrose phosphorylase activity thereby can be determined at any assay conditions. For the purpose of this invention improvements in thermal stability of a certain sucrose phosphorylase were determined by measuring one or more of the following characteristics:

Tm50-value: For the purpose of this invention, the Tm50-value is the temperature at which the sucrose phosphorylase enzyme possesses 50% of its initial activity after incubation for 15 min at this temperature. The initial activity is the activity of the respective enzyme without temperature treatment, i.e. with 15 min incubation at room temperature. The enzyme activity can be determined in principle by using any activity assay. For the purpose of this invention Assay I or Assay II for the determination of phosphorolytic activity as described above have been used as specified in the examples.

Residual activity after 15 min/70° C.: For the purpose of this invention, residual activity after 15 min/70° C. is defined as the activity of a sucrose phosphorylase enzyme after incubation for 15 min at 70° C. compared to its activity without incubation at 70° C. The residual activity is calculated by dividing the activity after incubation at 70° C. for 15 min by the activity without incubation at 70° C. and multiplying the value by 100 to obtain the residual activity value in percent. The enzyme activity can be determined in principle by using any activity assay. For the purpose of this invention Assay II for the determination of phosphorolytic activity as described above has been used as specified in the examples.

aG1P formation: For the purpose of this invention, the efficiency of a sucrose phosphorylases in aG1P formation at high concentrations of the substrate sucrose was tested by incubation of 20 U of each heat-purified sucrose phosphorylase in a solution containing 1 M sucrose and 1 M phosphate buffer pH 7 at 30° C. for 24 h, and subsequent quantification of the aG1P concentration of the reaction mixture. The aG1P concentration was determined by adding a 10 µL sample to 90 µL detection reagent containing 48 mM potassium phosphate buffer, 2 mM MgCl2, 0.7 mM NADP, 3.8 mM glucose 6-phosphate dehydrogenase and 3.3 U/mL phosphoglucomutase. After incubation for 20 min at room temperature, the absorbance at 340 nm was determined. The amount of aG1P was quantified with an aG1P calibration curve derived from samples with known amounts of aG1P.

Definition Homology: In the meaning of this invention, the homology is preferably calculated as identity using BLASSP (Stephen F. Altschul, Thomas L. Madden, Alejandro A. Schaffer, Jinghui Zhang, Zheng Zhang, Webb Miller, and David J. Lipman (1997) "Gapped BLAST and PSI-BLAST: a new generation of protein database search programs", Nucleic Acids Res. 25:3389-3402; Stephen F. Altschul, John C. Wootton, E. Michael Gertz, Richa Agarwala, Aleksandr Morgulis, Alejandro A. Schaffer, and Yi-Kuo Yu (2005) "Protein database searches using compositionally adjusted substitution matrices." FEBS J. 272:5101-5109), preferably using version BLASTP 2.2.29+, preferably using the following settings:

Field "Enter Query Sequence": Query subrange: none
Field "Choose Search Set": Database: non-redundant protein sequences (nr); optional parameters: none
Field "Program Selection": Algorithm: blastp (protein-protein BLAST)
Algorithm parameters: Field "General parameters": Max target sequences: 100; Short queries: Automatically adjust parameters for short input sequences; Expect threshold: 10; Word size: 3; Max matches in a query range: 0
Algorithm parameters: Field "Scoring parameters": Matrix: BLOSUM62; Gap Costs: Existence: 11 Extension: 1; Compositional adjustments: Conditional compositional score matrix adjustment
Algorithm parameters: Field "Filters and Masking": Filter: none; Mask: none. Results are filtered for sequences with more than 35% query coverage.

Substrates of sucrose phosphorylase enzymes: For phosphorolytic reactions of sucrose phosphorylases, sucrose is the substrate with highest industrial relevance, which is converted into the product aG1P and the co-product fructose. aG1P may be further converted by additional enzymes to secondary products, either sequentially, or concurrently in a one-pot-reaction. Secondary products include molecules such as trehalose, cellobiose, laminaribiose, laminaritriose, laminaritetraose, laminaribiose-oligosaccharides, lacto-N-biose, galacto-N-biose, and kojibiose. Additional enzymes for the conversion of aG1P to secondary products are enzymes like trehalose phosphorylase (EC 2.4.1.64 or EC 2.4.1.216), cellobiose phosphorylase (EC 2.4.1.20), laminaribiose phosphorylase (EC 2.4.1.31), lacto-N-biose phosphorylase (EC 2.4.1.211), UDP-glucose-4-epimerase (EC 5.1.3.2), UTP-glucose-1-phosphate uridylyltransferase (EC 2.7.7.9), phosphoglucomutase (EC 5.4.2.2), glucose 6-phosphate 1-epimerase (EC 5.1.3.15), beta-phosphoglucomutase (EC 5.4.2.6), kojibiose phosphorylase (EC 2.4.1.230), and xylose isomerase (EC 5.3.1.5). For transglycosylation reactions of sucrose phosphorylases, sucrose or aG1P are usual substrates, which may be converted without any additional enzyme in the presence of a co-substrate. Co-substrates enclose molecules like glucose, arabinose, sorbose, ketoxylose, ketoarabinose, rhamnulose, fucose. fructose, galactose, xylose, xylitol, arabitol, sorbitol, glycerol, 1,2-propanediol, 2,3-methoxy-1,2-propanediol, 3,3-ethoxy-1,2-propanediol, 4,3-allyloxy-1,2-propanediol, 5,3-tert-butoxy-1,2-propanediol, 6,3-(o-methoxyphenoxy)-1,2-propanediol, caffeic acid, acetate, formate, sodium benzoate, hydrochinone, catechin, epigallocatechin gallate, 4-hydroxy-2,5-dimethyl-3(2H)-furanone, 2-ethyl-4-hydroxy-5-methyl-3(2H)-furanone, and kojic acid.

TABLE 1

Overview over the Sequence IDs

| SEQ ID | Source | Mutations compared to SEQ ID NO: 1 |
|---|---|---|
| SEQ ID NO: 1 | Bifidobacterium magnum | none |
| SEQ ID NO: 2 | Bifidobacterium longum | not applicable |
| SEQ ID NO: 3 | Bifidobacterium animalis | not applicable |
| SEQ ID NO: 4 | Bifidobacterium thermophilum | not applicable |
| SEQ ID NO: 5 | Bifidobacterium adolescentis | not applicable |
| SEQ ID NO: 6 | variant of SEQ ID NO: 1 | E92L |
| SEQ ID NO: 7 | variant of SEQ ID NO: 1 | S124Q |
| SEQ ID NO: 8 | variant of SEQ ID NO: 1 | S124K |
| SEQ ID NO: 9 | variant of SEQ ID NO: 1 | S124T |
| SEQ ID NO: 10 | variant of SEQ ID NO: 1 | A148R |
| SEQ ID NO: 11 | variant of SEQ ID NO: 1 | A148K |
| SEQ ID NO: 12 | variant of SEQ ID NO: 1 | T157D |
| SEQ ID NO: 13 | variant of SEQ ID NO: 1 | Q188Y |
| SEQ ID NO: 14 | variant of SEQ ID NO: 1 | I231V |
| SEQ ID NO: 15 | variant of SEQ ID NO: 1 | L371A |
| SEQ ID NO: 16 | variant of SEQ ID NO: 1 | T461G |
| SEQ ID NO: 17 | variant of SEQ ID NO: 1 | A148K, Q188Y |
| SEQ ID NO: 18 | variant of SEQ ID NO: 1 | A148K, T157D, Q188Y, L371A, T461G |

The present invention is further illustrated by the examples and the sequence listing from which further features, embodiments and advantages may be taken.

EXAMPLES

Example 1

General Methods

Cloning of the wild-type sucrose phosphorylases: The sucrose phosphorylase genes from *Bifidobacterium magnum*, *Bifidobacterium longum*, *Bifidobacterium animalis*, *Bifidobacterium thermophilum* and *Bifidobacterium adolescentis* were codon-optimized for expression in *E. coli* and synthesized by Eurofins MWG Operon or Geneart Thermo Fisher Scientific. Each gene was cloned into the expression vector pLE1A17 or pLE1A27 (both derivatives of pRSF-1b, Novagen). The resulting plasmids were used for transformation of *E. coli* BL21(DE3) cells.

Molecular biology methods: Mutants of the sucrose phosphorylase enzymes were created by standard site directed mutagenesis technologies as known to the skilled person and as described in the state of the art.

Expression of recombinant sucrose phosphorylases: Recombinant sucrose phosphorylases were routinely expressed by inoculating Medium I (4.6 g/L yeast extract, 9.3 g/L peptone, 25 mM $Na_2HPO_4*12H_2O$, 25 mM $KH_2PO_4$, 50 mM $NH_4Cl_2$, $Na_2SO_4$, 5 g/L glycerol, 0.5 g/L glucose *$1H_2O$, 2 mM $MgSO_4$, 50 µg/mL kanamycin) with a fresh overnight culture. Cultures were grown at 37° C. up to an optical density at 600 nm of 0.6-0.8. Cultures were induced with 0.1 mM IPTG final concentration. Expression was at 30° C. overnight.

Preparation of sucrose phosphorylase enzyme preparations: Preparation of cell free extract was done using procedures well known as described elsewhere. Cells were harvested by centrifugation and suspended in a buffer containing 50 mM potassium phosphate buffer pH 7, 2 mM $MgCl_2$, 0.5 mg/mL lysozyme and 20 U/mL nuclease. Cell disruption was achieved by sonication or repeated freeze/thaw cycles. Cell free extract containing soluble enzyme was separated from the debris by centrifugation.

Determination of aG1P concentration: 10 µL sample was added to 90 µL detection reagent containing 48 mM potassium phosphate buffer, 2 mM $MgCl_2$, 0.7 mM NADP, 3.8 mM glucose 6-phosphate dehydrogenase and 3.3 U/mL phosphoglucomutase. After incubation for 20 min at room temperature, the absorbance at 340 nm was determined. The amount of aG1P was quantified with an aG1P calibration curve derived from samples with known amounts of aG1P.

Determination of sucrose phosphorylase concentration: 10 µL of a sample containing 0.5-1.5 µg sucrose phosphorylase were loaded onto 12% acrylamide gel, resolved in SDS-PAGE and stained with Coomassie Brilliant Blue G-250. Experimental conditions were selected for SDS-PAGE in order to assure proper separation of proteins and allow correct quantification. The intensity of the band corresponding to the sucrose phosphorylase was measured and the enzyme amount quantified with a bovine serum albumin calibration curve derived from samples with known amounts of bovine serum albumin analyzed on the same gel. Samples were analysed in triplicates.

Activity measurements: Activity of sucrose phosphorylase can be determined as the phosphorolytic cleavage of sucrose as described in Assay I or Assay II. Additionally, the activity of a sucrose phosphorylase for the hydrolysis of aG1P can be determined as described in Assay III.

Assay I: Phosphorolytic activity of a sucrose phosphorylase was routinely assayed at 30° C. using a continuous coupled assay in which the aG1P produced from sucrose substrate is converted to glucose-6-phosphate by phosphoglucomutase. Glucose-6-phosphate and NADP is converted to 6-phospho-gluconate and NADPH by glucose 6-phosphate dehydrogenase. The detection is based on measuring the absorbance of NADPH at 340 nm. The assay solution contained: 75 mM potassium phosphate buffer pH 7, 2.5 mM NADP, 10 µM glucose 1,6-bisphosphate, 10 mM $MgCl_2$, 250 mM sucrose, 3 U/mL phosphoglucomutase and 3.4 U/mL glucose 6-phosphate dehydrogenase. 1 U is defined as the amount of enzyme that catalyzes the production of 1 µmol of aG1P at the specified conditions.

Assay II: Alternatively, phosphorolytic activity can be determined in an uncoupled assay. In brief, sucrose phosphorylase is incubated at 30° C. in the presence of 500 mM sucrose and 200 mM potassium phosphate buffer pH 7. At discrete time-points, 20 µl samples were taken and inactivated by the addition of 80 µL 0.25 M HCl. Samples were neutralized and the aG1P-concentration determined as described above. 1 U is defined as the amount of enzyme that catalyzes the production of 1 µmol of aG1P at the specified conditions.

Assay III: For the determination of hydrolytic activity of a sucrose phosphorylase, such sucrose phosphorylase was added to a solution containing 100 mM aG1P and 50 mM 2-(N-morpholino)ethanesulfonic acid-buffer pH 7 and incubated at 30° C. At discrete time-points, 100 µl samples were taken and inactivated by the addition of 200 µL 1 M HCl. Samples were neutralized and the aG1P-concentration determined as described above. Hydrolytic activity was calculated from the initial slope by linear regression of aG1P-concentration over time. 1 HU (hydrolytic unit) is defined as the amount of enzyme that catalyzes the hydrolytic cleavage of 1 µmol of aG1P per min at the specified conditions. If the sucrose phosphorylase was derived from a non-purified cell free extract, a heat purification step was performed in order to remove the aG1P-degrading activity of the host background. Therefor cell extract was incubated at 55° C. for 15 min. The heat-purified cell free extract containing soluble enzyme was separated from the debris by centrifugation.

Example 2

Characterization of Wild-Type Sucrose Phosphorylases

Expression of recombinant sucrose phosphorylases: Recombinant sucrose phosphorylases were expressed by inoculating Medium I (4.6 g/L yeast extract, 9.3 g/L peptone, 25 mM $Na_2HPO_4*12H_2O$, 25 mM $KH_2PO_4$, 50 mM $NH_4Cl_2$, $Na_2SO_4$, 5 g/L glycerol, 0.5 g/L glucose *$1H_2O$, 2 mM $MgSO_4$, 50 µg/mL kanamycin) with a fresh overnight culture. Cultures were grown at 37° C. up to an optical density at 600 nm of 0.6-0.8. Cultures were induced with 0.1 mM IPTG final concentration. Expression was at 30° C. overnight.

Preparation of sucrose phosphorylase enzyme preparations: Cells were harvested by centrifugation and suspended in a buffer containing 50 mM potassium phosphate buffer pH 7, 2 mM $MgCl_2$, 0.5 mg/mL lysozyme and 20 U/mL nuclease. Cell disruption was achieved by sonication or repeated freeze/thaw cycles. Cell free extract containing soluble enzyme was separated from the debris by centrifugation.

The Tm50-values of the wild-type sucrose phosphorylases were determined. Cell extracts containing a certain sucrose phosphorylase were incubated for 15 minutes at temperatures between 50° C.-80° C. After a regeneration step for 30 minutes on ice, and after centrifugation to remove precipitated protein, the sucrose phosphorylase activities in the supernatant were determined using Assay I described in Example 1. Additionally, the activity of cell extract without heat treatment was determined using Assay I described in Example 1. Residual activity was calculated by dividing the activity after the heat treatment by the activity without heat treatment and multiplication by 100. The Tm50-value was determined as the temperature at which the enzyme possesses 50% residual activity. Table 1 lists the Tm50-values of the different wild-type sucrose phosphorylases. The highest Tm50-values were observed by the sucrose phosphorylases encoded by SEQ ID NO: 3 and 4. All wild-type enzymes showed unusually high thermal stability for enzymes derived from mesophilic isolates.

TABLE 1

| Tm50-value of wild-type sucrose phosphorylases | |
|---|---|
| SEQ ID | Tm 50 (° C.) |
| SEQ ID NO: 1 | 65 |
| SEQ ID NO: 2 | 68 |
| SEQ ID NO: 3 | 72 |
| SEQ ID NO: 4 | 72 |
| SEQ ID NO: 5 | 69 |

The phosphorolytic and hydrolytic activities of the wild-type sucrose phosphorylases were determined using Assays I and III as described in Example 1. For Assay III, the enzymes were purified by heat treatment as described in Assay III in Example 1. The ratio of phosphorolytic activity to hydrolytic activity (P/H-ratio) of each sucrose phosphorylase was determined by dividing the phosphorolytic activity of the sucrose phosphorylase by the hydrolytic activity of the same sucrose phosphorylase, and multiplying the value by 100 to obtain the P/H-ratio for such sucrose phosphorylase in percent. The results for the different wild-type enzymes are listed in Table 2. Surprisingly it was found, that the sucrose phosphorylases encoded by SEQ ID NO: 1 and SEQ ID NO: 3 showed the highest P/H-ratio of >300. A high P/H-ratio is very desirable for the use of sucrose phosphorylases in industrial applications as it leads to higher product yields both in the application of sucrose phosphorylases for aG1P synthesis as well as for transglycosidation reactions.

TABLE 2

| P/H-ratio | |
|---|---|
| SEQ ID | P/H-ratio (%) |
| SEQ ID NO: 1 | 373 |
| SEQ ID NO: 2 | 299 |
| SEQ ID NO: 3 | 354 |
| SEQ ID NO: 4 | 296 |
| SEQ ID NO: 5 | 157 |

The wild-type sucrose phosphorylases were tested for aG1P synthesis at high concentrations of the substrate sucrose. Cell extracts containing the wild-type sucrose phosphorylases were heat-purified by incubation at 55° C. for 15 min. The heat-purified cell free extract containing soluble enzyme was separated from the debris by centrifugation. 20 U of the respective sucrose phosphorylase was added to a solution containing 1 M sucrose and 1 M phosphate buffer pH 7. The reaction mixture was incubated at 30° C. for 24 h. The aG1P-concentration of the reaction mixture was determined as described in Example 1. SEQ ID NO: 1 produced the highest aG1P amount at the given reaction conditions (Table 3). This indicates that SEQ ID NO: 1 is the best enzyme for aG1P synthesis at high sucrose and phosphate concentrations.

TABLE 3

| aG1P synthesis from 1M sucrose and 1M phosphate | |
|---|---|
| SEQ ID | aG1P (mM) |
| SEQ ID NO: 1 | 484 |
| SEQ ID NO: 2 | 367 |
| SEQ ID NO: 3 | 354 |
| SEQ ID NO: 4 | 422 |
| SEQ ID NO: 5 | 293 |

The phosphorolytic activity (Assay I) and the sucrose phosphorylase concentration of a sample containing sucrose phosphorylase of SEQ ID: 1 were determined as described in Example 1. The specific activity was calculated by dividing the phosphorolytic activity by the sucrose phosphorylase concentration of the sample (Table 4).

TABLE 4

| Specific activity | |
|---|---|
| SEQ ID | U/mg |
| SEQ ID NO: 1 | 124 |

The sucrose phosphorylase coded by SEQ ID NO: 1 showed an excellent P/H-ratio, a high specific activity as well as an excellent performance at high substrate concentrations. However, the enzyme showed a slightly lower thermal stability than the related sucrose phosphorylases of SEQ ID NO: 2, 3, 4, and 5. It was therefore decided to improve the enzyme's thermal stability by enzyme engineering.

Example 3

Enzyme Engineering of Sucrose Phosphorylase

Expression of recombinant sucrose phosphorylases: Recombinant sucrose phosphorylases were expressed by inoculating Medium I (4.6 g/L yeast extract, 9.3 g/L peptone, 25 mM $Na_2HPO_4 \cdot 12H_2O$, 25 mM $KH_2PO_4$, 50 mM $NH_4Cl_2$, $Na_2SO_4$, 5 g/L glycerol, 0.5 g/L glucose $\cdot 1H_2O$, 2 mM $MgSO_4$, 50 µg/mL kanamycin) with a fresh overnight culture. Cultures were grown at 37° C. up to an optical density at 600 nm of 0.6-0.8. Cultures were induced with 0.1 mM IPTG final concentration. Expression was at 30° C. overnight.

Preparation of sucrose phosphorylase enzyme preparations: Cells were harvested by centrifugation and suspended in a buffer containing 50 mM potassium phosphate buffer pH 7, 2 mM $MgCl_2$, 0.5 mg/mL lysozyme and 20 U/mL nuclease. Cell disruption was achieved by repeated freeze/thaw cycles. Cell free extract containing soluble enzyme was separated from the debris by centrifugation.

Determination of residual activity after 15 min at 70° C.: A 50 µL aliquot of each sucrose phosphorylase was incubated at 70° C. for 15 min. Denatured protein was separated by centrifugation. The activity of the supernatant was determined using Assay II described in Example 1. Another aliquot of each SP was assayed directly for activity without heat-inactivation using Assay II described in Example 1. The resulting residual activities are listed in Table 5. Many variants showed a higher residual activity than the wild-type enzyme which means they possess an improved thermal stability compared to the wild-type.

TABLE 5

Residual activity after incubation at 70° C. for 15 min

| SEQ ID | Residual activity after 15 min at 70° C. (%) |
|---|---|
| SEQ ID NO: 1 | 17% |
| SEQ ID NO: 6 | 30% |
| SEQ ID NO: 7 | 16% |
| SEQ ID NO: 8 | 51% |
| SEQ ID NO: 9 | 42% |
| SEQ ID NO: 10 | 50% |
| SEQ ID NO: 11 | 52% |
| SEQ ID NO: 12 | 1% |
| SEQ ID NO: 13 | 17% |
| SEQ ID NO: 14 | 35% |
| SEQ ID NO: 15 | 16% |
| SEQ ID NO: 16 | 19% |
| SEQ ID NO: 17 | 64% |
| SEQ ID NO: 18 | 36% |

The Tm50-values of four SP variants was determined as described in Example 2. SEQ ID NO: 17 showed the highest Tm50-value, 5° C. higher than SEQ ID NO: 1.

TABLE 6

Tm50-value

| SEQ ID | Tm 50 (° C.) |
|---|---|
| SEQ ID NO: 11 | 68.5 |
| SEQ ID NO: 13 | 64.5 |
| SEQ ID NO: 17 | 70 |
| SEQ ID NO: 18 | 66.5 | aG1P formation, specific acitivity and P/H-ratio of SEQ ID NO:1 were determined as described in Example 2 (Table 7).

TABLE 7

Characterization of SEQ ID NO: 17 in comparison to SEQ ID NO: 1

| SEQ ID | SEQ ID NO: 1 | SEQ ID NO: 17 |
|---|---|---|
| aG1P after 24 h (mM) | 484 | 501 |
| Specific activity: (U/mg) | 124 U/mg | 128 U/mg |
| P/H-ratio | 373 | 331 |

---

The invention claimed is:

1. A sucrose phosphorylase comprising an amino acid sequence, wherein the amino acid sequence has at least 84% sequence identity or is 84% identical to SEQ ID NO: 1, and wherein the amino acid sequence comprises one or more substitutions at one or more amino acid positions of SEQ ID NO: 1, wherein the one or more amino acid positions is/are each and independently selected from the group consisting of the amino acid positions E92, S124, A148, Q188, I231, L371, and T461.

2. The sucrose phosphorylase of claim 1, wherein the sucrose phosphorylase comprises or consists of an amino acid sequence, wherein the amino acid sequence is has at least 84% sequence identity or is 84% identical to SEQ ID NO: 1, and wherein the amino acid sequence comprises one or more substitutions at one or more amino acid positions of SEQ ID NO: 1, wherein the one or more amino acid positions is/are each and independently selected from the group consisting of the amino acid positions E92L, S124Q, S124K, S124T, A148R, A148K, Q188Y, I231V, L371A, and T461G.

3. The sucrose phosphorylase of claim 1, wherein the amino acid sequence comprises two or more substitutions, wherein the pair of two amino acid positions of SEQ ID NO: 1 is selected from the group consisting of E92 and S124, E92 and A148, E92 and T157, E92 and Q188, E92 and I231, E92 and L371, E92 and T461, S124 and A148, S124 and T157, S124 and Q188, S124 and I231, S124 and L371, S124 and T461, A148 and T157, A148 and Q188, A148 and I231, A148 and L371, A148 and T461, T157 and Q188, T157 and I231, T157 and L371, T157 and T461, Q188 and I231, Q188 and L371, Q188 and T461, I231 and L371, I231 and T461, and L371 and T461.

4. The sucrose phosphorylase of claim 1, wherein the amino acid sequence comprises two or more amino acid substitutions at position A148 and Q188 of SEQ ID NO: 1.

5. The sucrose phosphorylase of claim 4, wherein the amino acid sequence comprises two or more of the following amino acid substitutions A148K, A148R, and Q188Y.

6. The sucrose phosphorylase of claim 1, wherein the amino acid sequence comprises one or more substitution at one or more amino acid positions of SEQ ID NO: 1, wherein the substitution at the one or more amino acid positions is/are each and independently selected from the group consisting of the substitutions:
- (i) position E92 is substituted with A, R, N, D, C, Q, G, H, I, L, K, M, F, P, S, T, W, Y, or V;
- (ii) position S124 is substituted with A, R, N, D, C, Q, E, G, H, I, L, K, M, F, P, T, W, Y, or V;
- (iii) position A148 is substituted with R, N, D, C, Q, E, G, H, I, L, K, M, F, P, S, T, W, Y, or V;
- (iv) position T157 is substituted with A, R, N, D, C, Q, E, G, H, I, L, K, M, F, P, S, W, Y, or V;
- (v) position Q188 is substituted with A, R, N, D, C, E, G, H, I, L, K, M, F, P, S, T, W, Y, or V;
- (vi) position I231 is substituted with A, R, N, D, C, Q, E, G, H, L, K, M, F, P, S, T, W, Y, or V;
- (vii) position L371 is substituted with A, R, N, D, C, Q, E, G, H, I, K, M, F, P, S, T, W, Y, or V; and
- (viii) position T461 is substituted with A, R, N, D, C, Q, E, G, H, I, L, K, M, F, P, S, W, Y, or V.

7. The sucrose phosphorylase of claim 1, wherein the sucrose phosphorylase comprises or consists of an amino acid sequence selected from the group consisting of SEQ ID NO: 8, SEQ ID NO:10, SEQ ID NO:11, SEQ ID NO:13, and SEQ ID NO:17.

8. The sucrose phosphorylase of claim 1, wherein the sucrose phosphorylase is capable of:
- a) catalyzing the phosphorolytic cleavage of substrate glucoside into alpha-D-glucose-1 phosphate and a co-product;
- b) catalyzing a transglycosylation reaction of a donor glucoside and an acceptor substrate, or
- c) a combination of a) and b).

9. The sucrose phosphorylase of claim 1, wherein the sucrose phosphorylase has one or more of the characteristics selected from the group (A), (B), (C), and (D):
- (A) a Tm50 value of at least 66.5° C. up to 90° C.;
- (B) a residual activity after 15 min incubation at 70° C. of at least 25% up to 100%;
- (C) a P/H-ratio of at least 200% up to 600%; or
- (D) an alpha-D-glucose-1 phosphate formation activity in 24 hours from 1M sucrose and 1M phosphate at 30° C. using 20 U heat-purified sucrose phosphorylase of at least 300 mM up to 1000 mM.

10. The sucrose phosphorylase of claim 9, wherein the sucrose phosphorylase has two or more of the characteristics selected from the group consisting of the characteristics
- a) (B) and (C);
- b) (B) and (D);
- c) (A) and (B) and (C);
- d) (A) and (B) and (D); or
- e) (A) and (B) and (C) and (D).

11. A method for preparing alpha-D-glucose-1 phosphate and a co-product, wherein the method comprises reacting a sucrose phosphorylase with a glucoside substrate, wherein the sucrose phosphorylase is a sucrose phosphorylase as defined in claim 1.

12. A method for preparing a glucoside product, wherein the method comprises the steps of
- (i) reacting a sucrose phosphorylase with a glucoside substrate to create a co-product and aG1P intermediate,
- (ii) reacting the alpha-D-glucose-1 phosphate intermediate and a glucoside acceptor molecule and one or more additional enzymes to create a glucoside final product, wherein the sucrose phosphorylase is a sucrose phosphorylase as defined in claim 1.

13. A method for preparing a transglycosylated product, wherein the method comprises reacting a donor glucoside substrate with a sucrose phosphorylase and an acceptor substrate to create a transglycosylated product, wherein the sucrose phosphorylase is a sucrose phosphorylase as defined in claim 1.

14. The sucrose phosphorylase of claim 1, wherein the amino acid sequence has at least 90% sequence identity with SEQ ID NO: 1.

15. The sucrose phosphorylase of claim 1, wherein the amino acid sequence has at least 95% sequence identity with SEQ ID NO: 1.

16. The sucrose phosphorylase of claim 1, wherein the amino acid sequence has at least 96% sequence identity with SEQ ID NO: 1.

17. The sucrose phosphorylase of claim 1, wherein the amino acid sequence has at least 98% sequence identity with SEQ ID NO: 1.

* * * * *